US009814778B2

(12) United States Patent
Lapitsky et al.

(10) Patent No.: US 9,814,778 B2
(45) Date of Patent: Nov. 14, 2017

(54) IONICALLY CROSSLINKED POLYELECTROLYTES AS UNDERWATER ADHESIVES AS CONTROLLED RELEASE VEHICLES

(71) Applicant: The University of Toledo, Toledo, OH (US)

(72) Inventors: Yakov Lapitsky, Toledo, OH (US); Yan Huang, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 14/639,759

(22) Filed: Mar. 5, 2015

(65) Prior Publication Data

US 2016/0074516 A1 Mar. 17, 2016

Related U.S. Application Data

(60) Provisional application No. 61/948,907, filed on Mar. 6, 2014.

(51) Int. Cl.

| | | |
|---|---|---|
| *A61K 47/32* | (2006.01) | |
| *A61K 9/00* | (2006.01) | |
| *A61K 47/34* | (2017.01) | |
| *A61L 24/00* | (2006.01) | |
| *A61L 24/04* | (2006.01) | |
| *A61L 26/00* | (2006.01) | |
| *C09J 139/02* | (2006.01) | |
| *C09J 139/08* | (2006.01) | |
| *C09J 177/04* | (2006.01) | |
| *C09J 179/02* | (2006.01) | |
| *C08K 3/32* | (2006.01) | |
| *C08G 73/02* | (2006.01) | |

(52) U.S. Cl.
CPC ............ *A61K 47/32* (2013.01); *A61K 9/0024* (2013.01); *A61K 47/34* (2013.01); *A61L 24/0015* (2013.01); *A61L 24/0031* (2013.01); *A61L 24/046* (2013.01); *A61L 26/008* (2013.01); *A61L 26/0019* (2013.01); *A61L 26/0066* (2013.01); *C09J 139/02* (2013.01); *C09J 139/08* (2013.01); *C09J 177/04* (2013.01); *C09J 179/02* (2013.01); *A61L 2400/06* (2013.01); *C08G 73/0206* (2013.01); *C08G 73/0266* (2013.01); *C08K 2003/321* (2013.01)

(58) Field of Classification Search
None
See application file for complete search history.

(56) References Cited

U.S. PATENT DOCUMENTS 5,373,052 A * 12/1994 Fukuda ................ A61K 9/5138
525/54.1
2013/0189313 A1 7/2013 Stewart et al.

FOREIGN PATENT DOCUMENTS

| CA | 2812599 A1 | 5/2012 |
|---|---|---|
| WO | 2012065148 A2 | 5/2012 |

OTHER PUBLICATIONS

Huang et al (Biomacromolecules 13:3868-3876, 2012).*
Huang et al., "Determining the Colloidal Behavior of Ionically Cross-Linked Polyelectrolytes with Isothermal Titration Calorimetry", The Journal of Physical Chemistry B, 2013, vol. 117, pp. 9548-9557.
Murthy et al., "Nanoparticle-Assembled Capsule Synthesis: Formation of Colloidal Polyamine—Salt Intermediates", The Journal of Physical Chemistry B, 2006, vol. 110, pp. 25619-25627.
Shao et al., "A Water-Borne Adhesive Modeled after the Sandcastle Glue of P. californica", Macromolecular Bioscience, 2009, vol. 9, pp. 464-471.
Shao et al., "Biomimetic Underwater Adhesives with Environmentally Triggered Setting Mechanisms", Advanced Materials, 2010, vol. 22, No. 6, pp. 729-733.
Yu et al., "Synthesis of nanoparticle-assembled tin oxide/polymer microcapsules", Chemical Communication, 2006, pp. 1097-1099.
Ajun et al., "Preparation of aspirin and probucol in combination loaded chitosan nanoparticles and in vitro release study", Carbohydrate Polymers, 2009, vol. 75, pp. 566-574.
Li et al., "Rheological properties of chitosan-tripolyphosphate complexes: From suspensions to microgels", Carbohydrate Polymers, 2012, vol. 87, pp. 1670-1677.
Shu et al., "A novel approach to prepare tripolyphosphate/chitosan complex beads for controlled release drug delivery", International Journal of Pharmaceutics, 2000, vol. 201, pp. 51-58.
Mang et al., "Design of Biocompatible Chitosan Microgels for Targeted pH-Mediated Intracellular Release of Cancer Therapeutics", Biomacromolecules, 2006, vol. 7, pp. 1568-1572.

* cited by examiner

*Primary Examiner* — Craig Ricci
(74) *Attorney, Agent, or Firm* — MacMillan, Sobanski & Todd, LLC

(57) ABSTRACT

Underwater adhesive materials, methods of making the same, and methods of using the same are described.

15 Claims, 81 Drawing Sheets

US 9,814,778 B2

IONICALLY CROSSLINKED POLYELECTROLYTES AS UNDERWATER ADHESIVES AS CONTROLLED RELEASE VEHICLES

RELATED APPLICATIONS

This application claims priority to U.S. Provisional Application Ser. No. 61/948,907 filed under 35 U.S.C. §111(b) on Mar. 6, 2014, the disclosure of which is incorporated herein by reference in its entirety.

STATEMENT REGARDING FEDERALLY SPONSORED RESEARCH

This invention was made with government support under Grant Number 1133795 awarded by the National Science Foundation. The government has certain rights in this invention.

BACKGROUND OF THE INVENTION

Underwater adhesion has several potential medical, household, and industrial applications. Underwater adhesives have been prepared by methods that typically rely on in situ polymerization, covalent crosslinking, or the use of highly specialized biological or biomimetic polymers. There has been a focus in the literature on biomimetic materials inspired by sessile marine organisms such as zebra mussels, tubeworms, and barnacles. Currently used strategies include the use of extracted or recombinant proteins, reactive dopamine derivatives, or coacervation and subsequent crosslinking of custom-designed polymers, which mimic the molecular structure and, consequently, the underwater adhesion properties of natural adhesive proteins. Some biomimetic adhesion strategies have included mixing polyelectrolytes with catechol-based crosslinkers, which convert the polymer solutions into adhesive gels. Other strategies involve synthesizing polyelectrolytes with crosslinkable catechol-based sidechain groups, or designing biomimetic polyelectrolyte complexes that undergo coacervation followed by either ionic or covalent crosslinker (which converts the liquid coacervates into adhesive solids).

Despite the current strategies, many challenges have limited the yield and application of biomimetic adhesives. The use of biological and biomimetic adhesion remains somewhat limited by the high cost of natural proteins, inefficient recombinant protein production, complicated syntheses, the use of potentially harmful oxidants to induce crosslinking, and the need for highly-specialized polymer structures. Similarly, older adhesion strategies such as epoxides, acrylic adhesives, and cyanoacrylate gels, suffer from deficiencies such as relying on chemical reactions to set the adhesive, being limited to a specific set of adhesion substrates, forming underwater bonds that are permanent and/or not self-healing upon failure, or requiring in situ polymerization. There is a need in the art for additional and improved underwater adhesives.

SUMMARY OF THE INVENTION

Provided herein is a composition comprising a non-polysaccharide polymer having two or more amine groups, and a multivalent phosphate crosslinker. The composition comprises an ionically crosslinked network that forms a gel-like coacervate at a pH ranging from about 4 to about 10. In certain embodiments, the polymer is substantially linear. In certain embodiments, the polymer is present at a concentration up to about 40 wt %. In certain embodiments, the multivalent phosphate crosslinker is selected from the group consisting of a tetravalent phosphate and a pentavalent phosphate. In certain embodiments, the multivalent phosphate crosslinker is not a single phosphate ion, $PO_4^{3-}$, or salt thereof. In certain embodiments, the multivalent phosphate crosslinker does not have more than 10 repeating units. In certain embodiments, the polymer having two or more amine groups comprises poly(allylamine hydrochloride) (PAH). In certain embodiments, the PAH has a molecular weight ranging from about 5 kDa to about 800 kDa. In certain embodiments, the PAH has a molecular weight ranging from about 1 kDa to about 2,500 kDa. In certain embodiments, the PAH has a molecular weight ranging from about 120 kDa to about 200 kDa. In certain embodiments, the multivalent phosphate crosslinker is selected from the group consisting of pyrophosphate (PPi) and tripolyphosphate (TPP). In certain embodiments, the polymer having two or more amine groups comprises poly(vinylamine). In certain embodiments, the polymer having two or more amine groups is selected from the group consisting of poly(vinylamine), polylysine, polyarginine, polyhistidine, polyethyleneimine, polyaminostyrene, polyvinylpyrrolidone, polymethylvinylamine, polyaniline, and poly(vinylpyridine).

In certain embodiments, the composition has a crosslinker polymer molar ratio ranging from about 0.12:1 to about 0.33:1. In certain embodiments, the composition has a crosslinker polymer molar ratio ranging from about 0.10:1 to about 0.25:1. In certain embodiments, the polymer is present at a concentration ranging from about 0.1 wt % to about 40 wt %. In certain embodiments, the polymer is present at a concentration up to about 10 wt %. In certain embodiments, the polymer is present at a concentration up to about 30 wt %. In certain embodiments, the polymer is present at a concentration up to about 40 wt %.

In certain embodiments, the polymer having one or more amine groups consists essentially of PAH, and the multivalent phosphate crosslinker consists essentially of PPi. In particular embodiments, the composition has a PPi:PAH molar ratio greater than about 0.12:1. In particular embodiments, the composition has a PPi:PAH molar ratio greater than about 0.25:1. In particular embodiments, the composition has a PPi:PAH molar ratio of about 0.33:1. In particular embodiments, the composition has a zeta potential of below +23 mV. In particular embodiments, the composition has a zeta potential of below +15 mV. In particular embodiments, the composition has a zeta potential of below +11 mV.

In certain embodiments, the polymer having two or more amine groups consists essentially of PAH, and the multivalent phosphate crosslinker consists essentially of TPP. In particular embodiments, the composition has a TPP:PAH molar ratio greater than about 0.10:1. In particular embodiments, the composition has a TPP:PAH molar ratio greater than about 0.20:1. In particular embodiments, the composition has a TPP:PAH molar ratio ranging from about 0.02:1 to about 10:1. In particular embodiments, the composition has a TPP:PAH molar ratio ranging from about 0.19:1 to about 0.25:1. In particular embodiments, the composition has a TPP:PAH molar ratio of about 0.20:1. In particular embodiments, the concentration of PAH monomer is above 1.7 mM. In particular embodiments, the concentration of PAH monomer is above 6 mM. In particular embodiments, the composition has a zeta potential of below +20 mV. In particular embodiments, the composition has a negative zeta potential. In particular embodiments, the composition is at a pH of from about 6 to about 8. In particular embodiments, the composition is at a pH of from about 4 to about 10.

In certain embodiments, the composition contains water at a concentration ranging from about 20 wt % to about 50 wt %. In certain embodiments, the composition contains water at a concentration ranging from about 24 wt % to about 38 wt %. In certain embodiments, the composition contains water at a concentration ranging from about 25 wt % to about 30 wt %. In certain embodiments, the composition has a storage modulus of greater than about 400 kPa. In certain embodiments, the composition exhibits a self-healing capability when torn. In certain embodiments, the composition has a tensile adhesion strength of greater than about 350 kPa.

In certain embodiments, the composition is capable of adhering to hydrophobic surfaces. In certain embodiments, the composition is capable of adhering to hydrophilic surfaces. In certain embodiments, the composition is capable of adhering to human skin. In certain embodiments, the composition is a soft gel. In certain embodiments, the composition has an underwater adhesion strength of greater than $10^5$ Pa. In certain embodiments, the composition further comprises an active payload (such as a drug) for long-term release.

Further provided herein is a method of making an adhesive material comprising the steps of mixing a polyamine with a multivalent phosphate crosslinker to obtain a mixture, allowing the mixture to coagulate over a period of time to form a gel-like complex and a supernatant, and separating the gel from the supernatant to obtain an adhesive material. In certain embodiments, the period of time is about 3 days. In certain embodiments, the period of time is less than an hour. In certain embodiments, the multivalent phosphate crosslinker consists essentially of a PPi solution with a concentration ranging from about 5.4 mM to about 54.1 mM. In certain embodiments, the multivalent phosphate crosslinker consists essentially of a TPP solution with a concentration ranging from about 4.4 mM to about 43.5 mM. In certain embodiments, the polyamine consists essentially of a PAH solution with a concentration ranging from about 1.7 mM to about 17.1 mM. In certain embodiments, the multivalent phosphate crosslinker has a concentration of about 7.5 wt %. In certain embodiments, the polyamine has a concentration of about 10 wt %. In certain embodiments, the method further comprises stirring the mixture. In certain embodiments, the method further comprises adjusting the pH to dissolve the adhesive material.

Further provided herein is a method of treating a wound comprising the steps of applying a composition described herein to a wound of a subject in need thereof, allowing the composition to set in the wound for a period of time, and contacting the composition with an agent having a pH of greater than 10 to dissolve the composition.

Further provided herein is a method for controllably releasing a drug (or other active ingredient) comprising the steps of encapsulating a drug in a composition described herein, and applying the composition to a target in need thereof.

Further provided herein is a method for controllably releasing a small molecule, the method comprising the steps of: adding a small molecule to either (i) a first solution comprising a non-polysaccharide polymer having two or more amine groups, or (ii) a second solution comprising a multivalent phosphate crosslinker; mixing the first solution with the second solution, at a pH ranging from about 4 to about 10, to form an adhesive gel; and applying the adhesive gel to a target location, where the small molecule is released from the adhesive gel over a period of time. In certain embodiments, the method further comprises adjusting the pH of the target location to an acidic or basic pH in order to dissolve the adhesive gel.

Further provided herein is a method of delivering an adhesive to a target location comprising the steps of mixing a polyamine with a multivalent phosphate crosslinker in acidic or basic solution to obtain a mixture, injecting the mixture to a target location, and adjusting the pH of the mixture to ambient pH to form an adhesive gel-like complex in the target location. In certain embodiments, the method further comprises adjusting the pH to an acidic or basic pH to dissolve the adhesive gel. In certain embodiments, the method further comprises removing supernatant solution from the target location.

Further provided herein is a method of delivering an adhesive to a target location comprising the steps of mixing a polyamine with a multivalent phosphate crosslinker in a solution to obtain a mixture, injecting the mixture to a target location, and adjusting the ionic strength of the solution to form an adhesive gel-like complex in the target location. In certain embodiments, the method further comprises adjusting the pH to an acidic or basic pH to dissolve the adhesive gel. In certain embodiments, the method further comprises removing supernatant solution from the target location.

Further provided herein is a method of delivering an adhesive to a target location comprising the steps of injecting a polyamine to a target location, and injecting a multivalent phosphate crosslinker to the target location to form an adhesive gel. In certain embodiments, the method further comprises removing supernatant solution from the target location.

Further provided herein is a kit for preparing an adhesive gel comprising a first container housing a polymer having two or more amine groups, and a second container housing a multivalent phosphate crosslinker. In certain embodiments, the kit further comprises a syringe.

Further provided herein is a kit for preparing an adhesive gel comprising a first container housing a dispersion comprising a polymer having two or more amine groups and a multivalent phosphate crosslinker, and a second container housing a pH modifier. In certain embodiments, the kit further comprises a syringe.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

DETAILED DESCRIPTION OF THE INVENTION

Figure 1A:
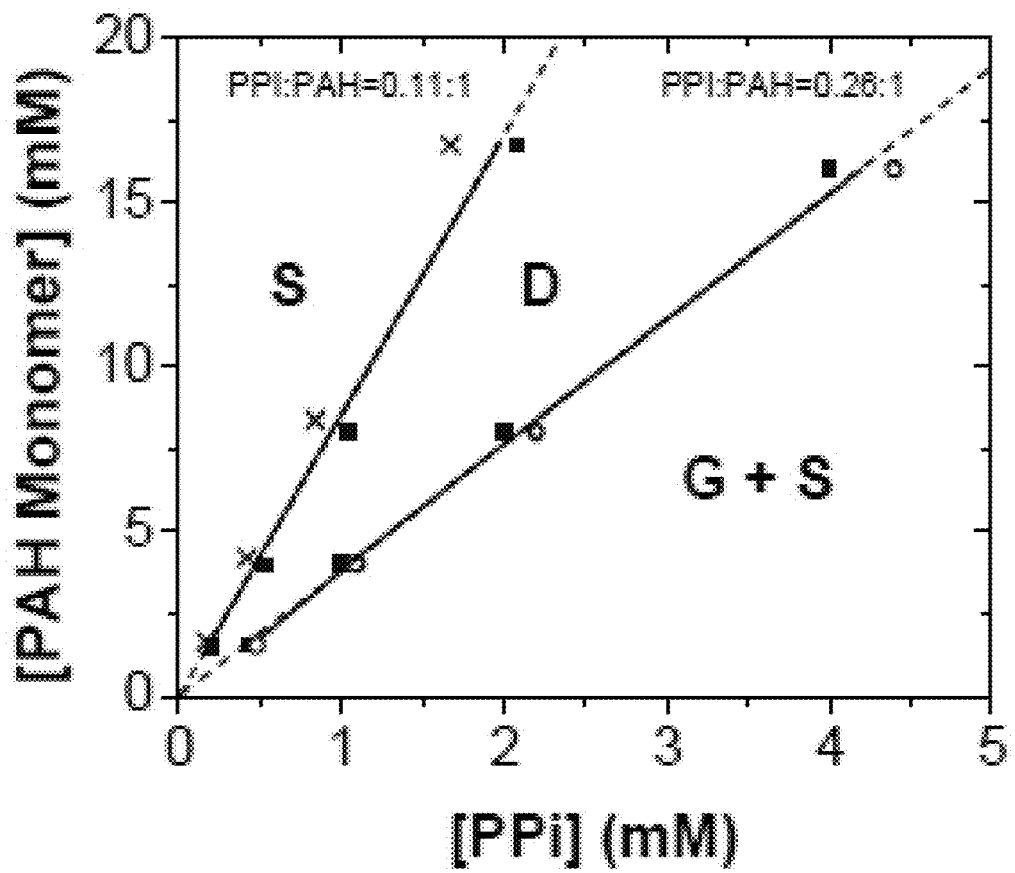
FIGS. 1A-1B: Phase maps of PAH/PPi (FIG. 1A) and PAH/TPP (FIG. 1B) mixtures at pH 7.0 showing compositions where clear molecular solutions (S), translucent colloidal dispersions (D), and macroscopic adhesive gels (G) form. The solid lines are phase boundaries, while the dotted lines represent counterion:monomer molar ratios of 0.1:1, 0.2:1, and 0.3:1. The points near the solid lines show the last data point before, and the first data point after, each state transition. The visual appearance of each aggregation state is illustrated in the panel at the bottom.
Figure 1A:
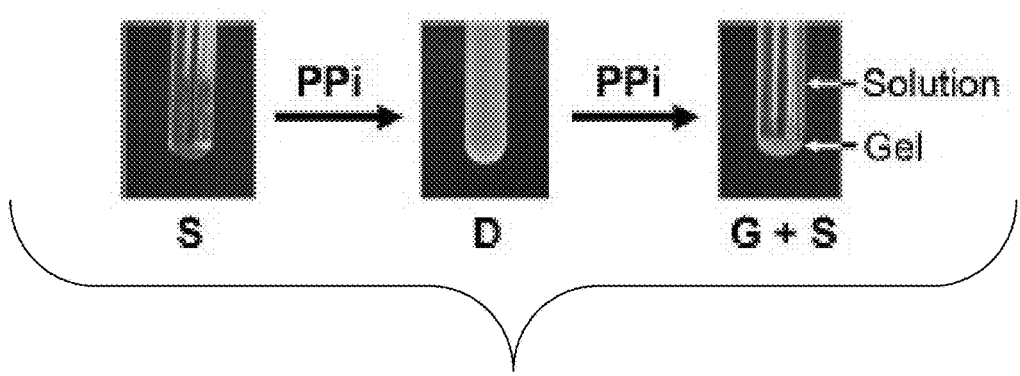

Throughout this disclosure, various publications, patents and published patent specifications are referenced by an identifying citation. The disclosures of these publications, patents and published patent specifications are hereby incorporated by reference into the present disclosure in their entirety to more fully describe the state of the art to which this invention pertains.

Definitions

For convenience, various terms used herein are defined prior to further description of the various embodiments of the present disclosure.

The term "self-healing" as used herein refers to the ability of a material to repair damage caused by mechanical stress or usage without external stimuli like heat, solvents, or plasticizers.

The term "polyphosphate" refers to a compound composed of phosphate units linked by phosphoanhydride bonds.

The term "polyamine" refers to a compound having two or more amine groups. As used herein, the term "polyamine" includes polymers having monomer units with one amine group in each monomer.

The term "polysaccharide" refers to a polymeric carbohydrate.

The term "gel" as used herein includes gels, gel-like complexes, gel-like adhesives, and gel-like coacervates.

General Description

Described herein are stiff gel-like complexes, also referred to as adhesive gels, that adhere to dissimilar substrates underwater, prepared from mixtures of readily-available polyelectrolytes and multivalent counterions. Specifically, the adhesive gels of the present disclosure are prepared by the ionotropic gelation of polyamines with phosphate-bearing multivalent anions. The adhesive gels form spontaneously and are soft materials that are adhesive in both wet and dry environments. Because the adhesive gels demonstrate a rheology in the presence of salt that is not conventionally associated with a gel, the term "gel-like coacervate" is sometimes used herein to refer to the adhesive gels. Thus, it is understood that the present disclosure is not limited by use of the term "gel."

In certain embodiments, the gel-like complexes deliver underwater adhesion strengths that are comparable to those of zebra mussels and barnacle adhesives, exhibit self-healing functionality, and form through spontaneous self-assembly. In certain embodiments, the gel-like complexes exhibit very high storage moduli ($G'_\infty$~400 kPa), self-heal when torn, and adhere to both hydrophilic and hydrophobic substrates under water, with short-term tensile adhesion strengths of 350-450 kPa. Surprisingly, these gel-like complexes adhere to both hydrophilic and hydrophobic substrates under water with tensile adhesive strength considerably greater than that of Scotch Permanent Double Sided Tape (up to ~400 kPa vs. ~85 kPa when used as a pressure-sensitive adhesives). In certain embodiments, the gel-like complexes deliver underwater adhesion strengths that exceed $10^5$ Pa. Furthermore, the gel-like complexes can be dissolved on demand by changing the ambient pH, which controls the ionization state of the polyelectrolyte and ionic crosslinker. These properties enable the gel-like complexes to provide a simple, cost-effective, and scalable platform for underwater adhesion.

Figure 8A:
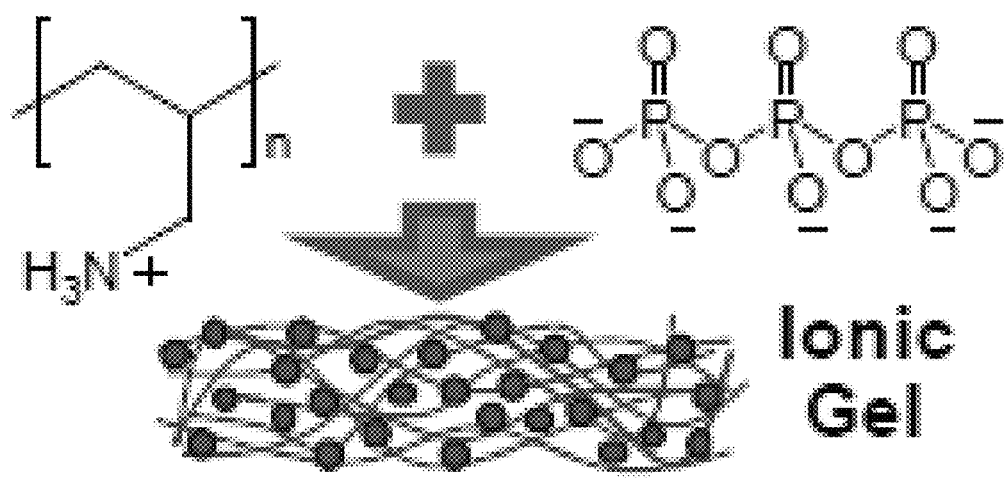
FIG. 8A: Exemplary illustration of an adhesive gel formed from a mixture of PAH and TPP.

When multivalent ions are mixed with oppositely charged polyelectrolytes in aqueous solutions, the multivalent ions can crosslink the polyeletrolyte chains into a variety of self-assembled, three-dimensional ionic networks. These range from colloidal particles to macroscopic coacervates and gels. The gel-like complexes of the present disclosure are prepared from mixing a polycation with a strongly-binding multivalent anion. More specifically, the gel-like complexes include a non-polysaccharide polymer backbone having two or more amine groups, and a multivalent phosphate crosslinker. These mixtures can self-assemble into remarkably stiff gels (or gel-like coacervates) with adhesive and self-healing properties. The two oppositely charged species undergo associative phase separation (e.g., through ionic crosslinking) to form a dense coacervate phase (rich in both the polymer and multivalent ion) and a dilute supernatant phase. In particular embodiments, the polycation that makes up the polymer backbone with amine groups is poly(allylamine hydrochloride) (PAH), and the phosphate crosslinker that makes up the multivalent anion is either pyrophosphate (PPi) or tripolyphosphate (TPP). An illustration of a non-limiting example of such a mixture between PAH and TPP is shown in FIG. 8A. These mixtures exhibit strong ionic bonding and can self-assemble into remarkably stiff gels with adhesive and self-healing properties. The adhesive gels can deliver short-term underwater adhesion strengths that exceed $10^5$ Pa, and can be dissolved on demand by altering the ambient pH.

Figure 8B:
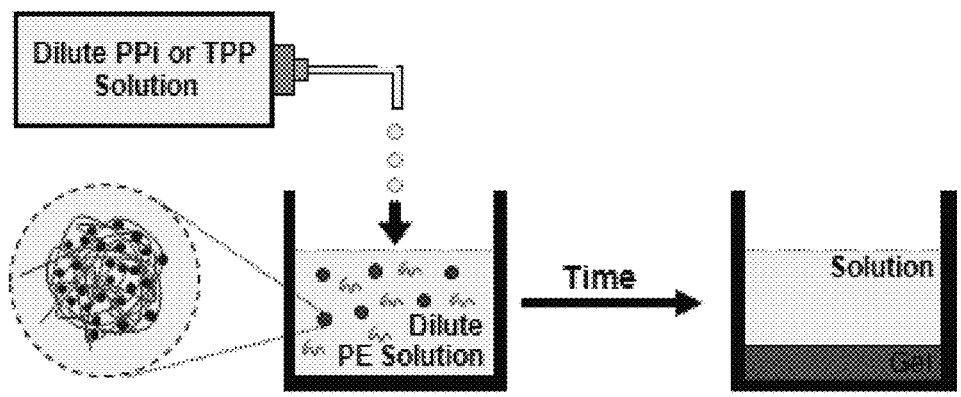
FIG. 8B: Exemplary illustration of the preparation of an adhesive formed from a mixture of PAH and either PPi or TPP.

The adhesive gels are prepared from simple methods involving the mixing of a polycation and phosphate crosslinker. An illustration of a non-limiting example of the process for preparing an adhesive gel from a mixture of PAH and either TPP or PPi is shown in FIG. 8B. In certain embodiments, the crosslinker is added dropwise to a dilute polycation solution. The cationic amine groups are then ionically crosslinked into gel-like complexes. A method of making the adhesive gels can further involve separating the gel-like complexes from supernatant solution.

Figure 6A:
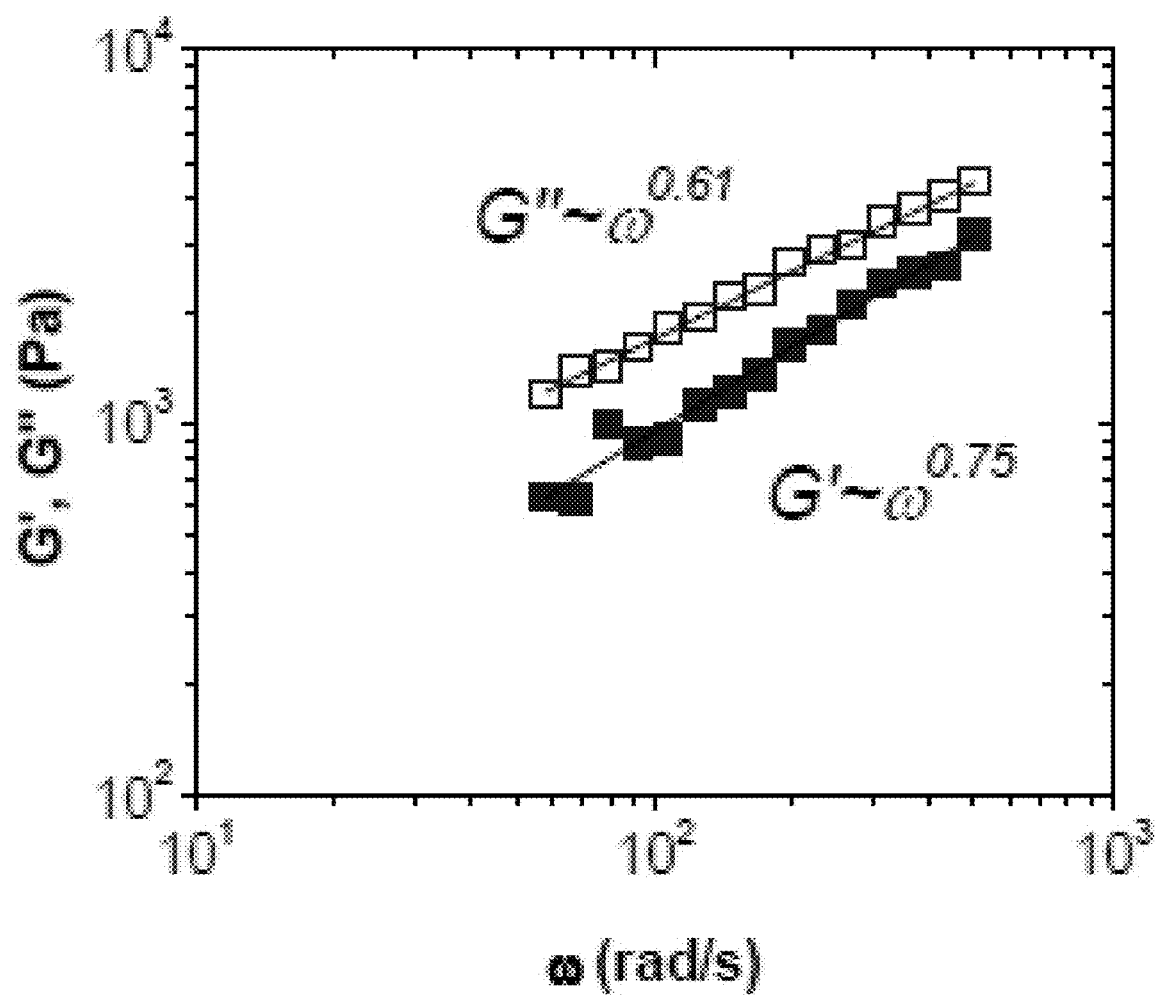
FIGS. 6A-6B: Frequency sweep data comparing the G' (■) and G" (□) of the PAH/citrate (FIG. 6A) and PAH/phosphate (FIG. 6B) complexes.
Figure 6B:
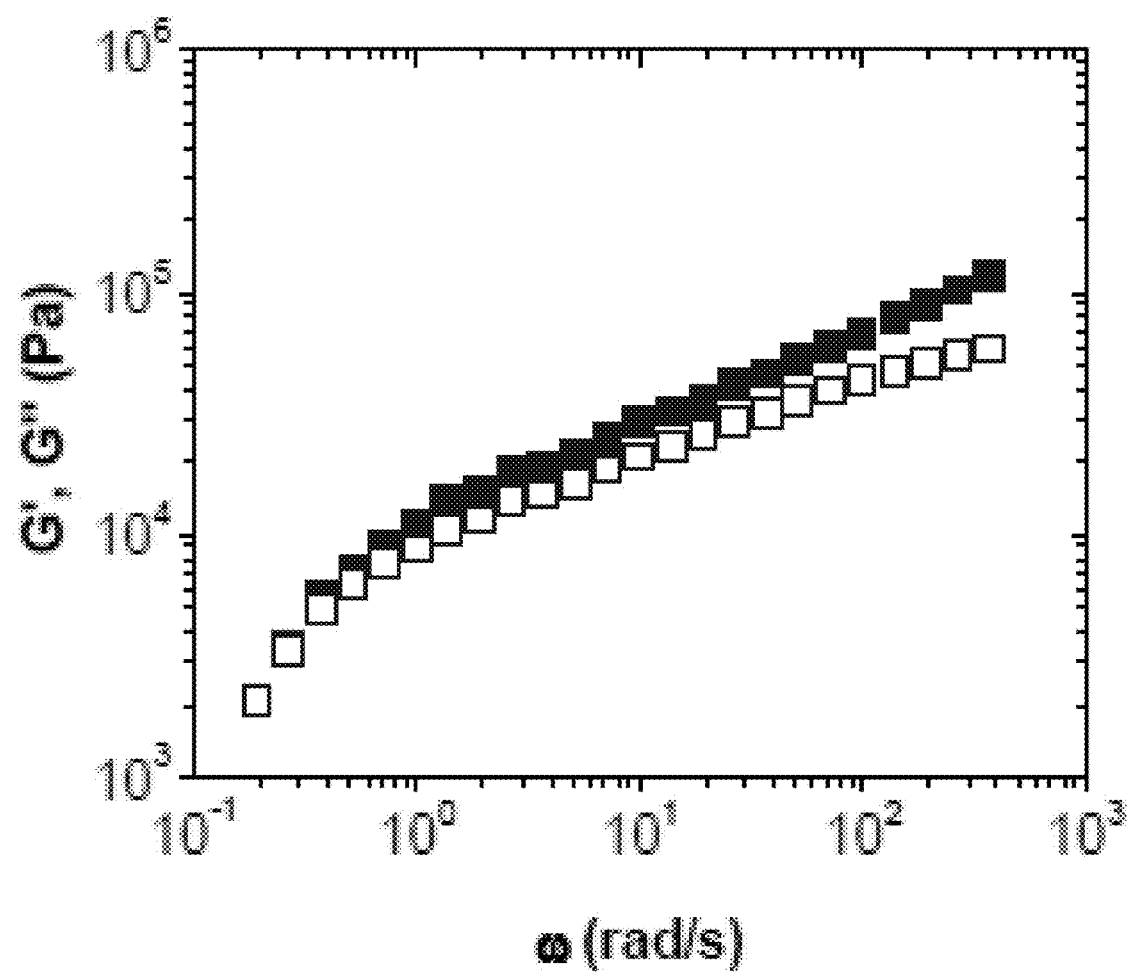

The rheological and adhesive properties of these phosphate-crosslinked polyamine gels are distinct from those of other ionically-crosslinked or polyelectrolyte structures. Calcium alginate and chitosan/TPP gels, for example, are not easily moldable and (unlike the gels described herein) are not usually adhesive. Conversely, the macroscopic complexes that form through the crosslinking of PAH with succinate, citrate, or ethylenediaminetetraacetic acid (EDTA) ions are viscous liquids. The viscous liquid-like rheology of PAH/citrate and PAH/phosphate complexes are shown in FIGS. 6A-6B. Despite their viscosity, these complexes have low cohesive strength and, like the alginate gels, make poor adhesives. Notably, the G' values of both PAH/citrate and PAH/phosphate complexes were significantly lower than those of PAH/PPi and PAH/TPP gels, as well as significantly more sensitive to the oscillation frequency, which further reflects weaker PAH/citrate and PAH/phosphate binding.

The adhesive gels of the present disclosure demonstrate that underwater adhesion can be achieved through the ionic crosslinking of common synthetic polyelectrolytes, which are widely available and have simple molecular structures. For example, PAH is a commercially-available polyelectrolyte that is being explored for drug and gene delivery, as well as cell encapsulation. PAH is a weak polycation with an effective $pK_a$ of 8.5. The molecular structure of PAH, in its hydrochloride salt form, is shown below as Formula I:

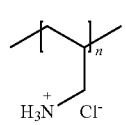

Formula I where n is any integer. PAH is prepared by the polymerization of allylamine, $C_3H_5NH_2$.

Likewise, both PPi and TPP are biocompatible tetra- and pentavalent polyprotic acids that are used as food additives and generally recognized as safe by the U.S. Food and Drug Administration. PPi and TPP are commercially available and inexpensive. The molecular structure of PPi, in its sodium salt form, is shown below as Formula II:

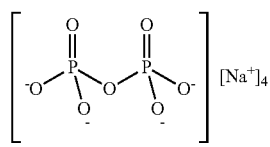

Formula II

The molecular structure of TPP, in its sodium salt form, is shown below as Formula III:

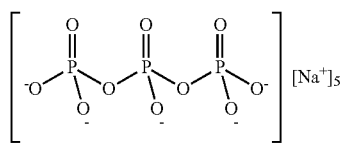

Formula III

While PPi and TPP mixtures with PAH are described for exemplary purposes, PPi and TPP mixtures with poly(vinylamine) indicate that similar adhesive materials can be prepared from a broader range of polyelectrolytes and ionic crosslinkers. Therefore, the skilled practitioner will understand that the present disclosure is by no means limited to PAH/PPi and PAH/TPP mixtures, but rather encompasses a wide variety of mixtures between a polyamine and a phosphate-bearing multivalent anion. In general, the adhesive gels of the present disclosure are compositions that include a polymer having two or more amine groups, where the polymer is a non-polysaccharide (as opposed to having sugar ring monomers), and a multivalent phosphate crosslinker. In some embodiments, the polymer backbone is substantially linear. In other embodiments, the polymer backbone is made of a branched polymer, such as, but not limited to, a branched polyethyleneimine. It is to be understood that the amine groups can be pendant groups or in the polymer backbone itself. Polymers other than PAH which are suitable in their salt forms for use as the polymer backbone include, but are not limited to: poly(vinylamine), polylysine, polyarginine, polyhistidine, and polyethyleneimine. Many other polyamines can be utilized in the polymer backbone. However, while not wishing to be bound by theory, it is believed that the polymer should have more than two amine groups. Phosphate crosslinkers other than PPi and TPP which are suitable for use as a multivalent phosphate crosslinker include any multivalent anions containing multiple phosphorus atoms, such as polyphosphates, pyrophosphates, trimetaphosphates, tripolyphosphates, or hexametaphosphates. Some non-limiting examples of salt forms of these phosphates include, but are not limited to: sodium hexametaphosphate (SMHP), sodium polyphosphate, tetrasodium pyrophosphate, and tetrapotassium pyrophosphate.

In the examples discussed herein, mixtures of PAH/PPi and PAH/TPP were prepared and analyzed via dynamic and electrophoretic light scattering, rheology, and adhesion tests. These mixtures showed that the adhesive gels of the present disclosure have many advantages. Their preparation is simple, inexpensive, and scalable. Because they form via self-assembly, their use requires no chemical crosslinking and minimizes the risk of harmful side reactions. They are extremely stiff, with plateau storage moduli ($G_\infty'$-values) near $4\times10^5$ Pa, which helps immobilize the bonded surfaces. (The high storage moduli of the adhesive gels is indicative of a very high crosslink density.) The adhesive gels adhere well to both hydrophilic and hydrophobic substrates. They are able to self-heal when torn. They are capable of the encapsulation and long-term release of active molecules. Also, they can be redissolved on demand by changing the ambient solution conditions.

The formation of adhesive PAH/PPi and PAH/TPP complexes depends on the cross-linking ion:PAH monomer ratios, where PAH remains solubilized at very low ion:monomer molar ratios and forms ionically cross-linked complexes when higher ion:monomer ratios are used. These complexes first form stable colloidal dispersions and, at even higher multivalent ion concentrations (where their electrostatic repulsion is diminished), coagulate into macroscopic adhesives.

The adhesive gels described herein are sensitive to pH and ionic strength. Neutral pH is preferred for making the adhesive gels. However, the optimal pH level is determined by the identity of the polymer molecule used. For example, above a pH of about 10 or 10.5, the PAH-based gels no longer formed. Without wishing to be bound by theory, it is believed this is because a high charge density is important for forming the gel. Because of this, the adhesion of the gels is controllable. Because the ionization states of PAH and phosphates are pH-sensitive, the adhesive gels can be rapidly dissolved on demand by changing the pH. In certain embodiments, the adhesive gels are easily removed by raising the pH to about 12, which deprotonates the PAH amines and dissolves the ionotropic gels. In certain embodiments, at pH 11 or 12, the adhesive gels simply dissolve. Similarly, the adhesive gels dissolve when placed in concentrated acid, which reduces the ionization of the multivalent phosphate crosslinker. This stimulus sensitivity further distinguishes these ionotropic adhesive gels from covalently crosslinked adhesives. Also, in certain embodiments, the phosphate crosslinker is leached out of the complex over a long period of time, on the order of several months, causing the complex to dissolve, providing further methods of controllably reversing adhesion.

Because the polymer-counterion binding is reversible, the gels also exhibit self-healing properties. In certain embodiments, when the gels are torn or broken, they are capable of recovering their entire storage moduli within 10-30 minutes. This property is significantly advantageous for many industrial, household, and medical applications.

Dilute mixtures of the polymer (such as PAH) and crosslinker (such as TPP or PPi) starting materials can be used, or, alternatively, much higher concentrations of the starting materials can be used to form more adhesive gel. However, the coagulation rates are concentration-dependent. Also, increased concentrations may decrease the adhesion of the adhesive gel due to an increased salt concentration resulting from the counterions of the starting materials. The salt concentration also affects the self-healing of the adhesive gels. In the presence of salt, the relaxation becomes faster, so self-healing is also faster. Additionally, when the polymer binds, it releases a proton, which changes the pH upon complexation. Thus, the concentrations of the initial polymer and crosslinker starting materials can be selected based on the desired characteristics of the resulting adhesive gels, and various properties of the adhesive gels can be tailored by the choice of starting material concentration.

Ionotropic gelation of polyamines with phosphate-bearing multivalent anions, as described herein, yields remarkably stiff, self-healing, and adhesive gels, which can adhere to dissimilar substrates under water. The elastic moduli of these gels (G' ~$4 \times 10^5$ Pa) are significantly higher than those typically obtained from gels formed through spontaneous self-assembly, and their adhesion strength is comparable to some of the natural underwater adhesives, such as those produced by zebra mussels and barnacles. The adhesive gels are prepared from inexpensive and readily-available ingredients, are easily scalable, and are useful in a wide variety of applications including, but not limited to, wound healing, bone repair, drug and gene delivery, antibacterial coatings, sealants, materials synthesis, surgical adhesives, and water treatment. The adhesive gels adhere to a wide variety of surfaces that includes human skin, Teflon®, glass, acrylic, PMMA, paper, and metal, and the gels likely adhere to a wide variety of other surfaces such as, but not limited to, wood, plastics, ceramics, concrete, brick, stone, marble, granite, and clay.

In certain embodiments, the adhesive gels described herein are highly sensitive to both pH and ionic strength. Because PPi and TPP are polyprotic acids whose charges increase with pH, the complexes form more readily (i.e., at lower ion:PAH monomer ratios) from neutral or slightly basic parent PAH, PPi, and TPP solutions (at pH 7.0 or 8.0) than under acidic conditions. When the parent solution pH exceeds the effective p$K_a$ of PAH (i.e., pH 8.5), however, the PAH becomes less charged, though the ionic complexes still continue to form upon mixing until a pH of about 10. Conversely, the ionic strength has little impact on the onset of PAH/PPi and PAH/TPP complex formation, although the coagulation of these complexes into macroscopic gel-like adhesives occurs over a broader range of compositions at higher monovalent salt concentrations.

The ionic networks have the longest relaxation times when prepared from PAH, PPi, and TPP solutions at a pH of near 7.0 and at low ionic strengths. Hence, the adhesive gels' adhesion is strongest and most durable when prepared under these conditions. These relaxation times and adhesion strengths/longevities decrease slightly when the preparation pH is reduced to 6.0, but diminish sharply when the preparation pH is increased to 8.0 (where the PAH linear charge density is reduced). Once formed, the ionic networks prepared from solutions at pH 7.0 maintain their long relaxation times when the ambient pH is between roughly 6.5 and 9, but become fluid-like at higher and lower pH-levels. Similarly, the ionic networks become more fluid-like and deliver weaker adhesion at higher ionic strengths, with the TPP-based complexes exhibiting greater salt stability than the PPi-based complexes.

The adhesive gels' sensitivity to changes in pH and ionic strength can be utilized to trigger their deposition to surfaces in response to external stimuli, which enables their use as injectable adhesives. The adhesive gels also have very low solute permeabilities, and can therefore serve as adhesive scaffolds for either pH-triggered or sustained release. In certain embodiments, the sustained release of small molecules from the gel lasts for multiple weeks. In certain embodiments, the sustained release of active payload molecules lasts for many months or even years. In certain embodiments, the active payload molecules are small molecules having a molecular weight of up to about 1,000 Daltons.

While elevated ionic strengths and high/low pH levels weaken the adhesion of the PAH/PPi and PAH/TPP complexes, the short-term tensile adhesion strengths still exceed $10^5$ Pa under many conditions. Furthermore, the salt and pH sensitivity of these mixtures can be exploited for injectable underwater adhesives or to dissolve the adhesives on demand. This versatility, combined with the inexpensive ingredients, results in the adhesive gels described herein being a useful and scalable platform for underwater adhesion, especially for applications requiring temporary or reversible attachment.

Among many other uses, the adhesive gels can be used as pressure-sensitive adhesives, or injectable formulations for medical applications such as wound closure. As a pressure-sensitive adhesive, a gel can be placed between two surfaces, whereupon a squeezing force between the two surfaces will cause the surfaces to adhere. For injection applications, the adhesive gels can either be pre-mixed into a colloidal dispersion, loaded into a syringe, and injected in dispersion form, or can be injected as a two-part mixture (of, for instance, polymer and crosslinker) that forms the colloidal dispersion after injection. Alternatively, an injectable composition could be prepared by mixing the polymer backbone (such as PAH) with the phosphate crosslinker (such as PPi or TPP) in an environment that prevents the adhesive gel from forming, such as a high or low pH. This mixture could then be injected into or onto a desired target location, and the pH could then be adjusted to ambient or near-ambient levels, thereby causing the adhesive gel to spontaneously form in or on the target location.

Any of a variety of suitable carriers, excipients, or adjuvants can be used to prepare an injectable formulation. By way of non-limiting examples, injectable dispersions may be prepared in glycerol, liquid polyethylene glycols, and mixtures thereof, or in oils. Under ordinary conditions of storage and use, these preparations can contain a preservative to prevent the growth of microorganisms. In some cases, the form should be sterile and should be fluid to the extent that easy injectability exists. It should be stable under the conditions of manufacture and storage and can be preserved against the contaminating action of microorganisms, such as bacteria and fungi. A carrier for an injectable formulation can be a solvent or dispersion medium containing, for example, water, ethanol, a polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In some cases, it is preferable to include isotonic agents, such as, but not limited to, sugars or sodium chloride. Prolonged absorption of the injectable compositions can be brought about by the use of agents delaying absorption such as, for example, aluminum monostearate, or gelatin. For parenteral administration in an aqueous solution, for example, the formulation can be suitably buffered if necessary and the liquid diluent can be first rendered isotonic with sufficient saline or glucose.

The adhesive gels are particularly useful for medical applications such as wound treatment. By way of a non-limiting example, the adhesive gels can be utilized as a surgical adhesive in wet environments. This is especially advantageous for military personnel. Because the adhesive gels have very low solute permeabilities, the adhesive gels are also useful as adhesive scaffolds for drugs or drug-like molecules. This is due to the tight network formed in the stiff gels. There is a scaling relationship between $G'_\infty$ and the ionic crosslink concentration (i.e., $G'_\infty \sim k_B T c_x$), corresponding to a hydrodynamic mesh size ($\zeta_H \sim c^{1/3}_x$) of approximately 1 nm, which indicates that the adhesive gels are an effective barrier for controlled release.

The adhesive gels offer a simple and effective method of controlled release. A payload can be loaded into these complexes by simply adding it to the polymer or crosslinker solution. Then, upon mixing these solutions (to form the adhesive gel) the payload becomes incorporated into the ionic network during the crosslinking process. After incorporation, the payload can be slowly released, with the release rate being dependent on the crosslinking density, the payload/polymer interaction, and the size of the payload molecule. Thus, the adhesive gels can be used as bioadhesive drug carriers or adhesive devices for other underwater controlled release applications. Long (multiple-month) release timescales can be achieved while releasing small molecule payloads using the gel-like coacervates. Without wishing to be bound by theory, it is believed that multiple-month release results from a densely crosslinked network acting as a remarkably effective barrier to diffusion, and not simply payload/polymer binding.

The encapsulation of active ingredients can be achieved by (1) incorporation during the gel formation process, where the active payload spontaneously binds to the polymer during its gelation, (2) blending the active payloads into the preformed adhesive gel, (3) simply allowing the payload to diffuse into the adhesive gel, or (4) pre-mixing the payload in a polymer solution (such as a concentrated 10 wt % PAH solution), then adding the premixed polymer/payload solution to a crosslinker solution (such as PPi or TPP solution) to form the ionic network. As demonstrated by the examples herein, the payload can be incorporated even when it is essentially non-binding. Suitable payloads for controlled release by the adhesive gels include, but are not limited to: antimicrobial agents, antibiotic agents, antiviral agents, antifungal agents, antiseptic agents, anti-inflammatory agents, and combinations thereof. In a similar fashion, the adhesive gels can also be used in household products to release fragrances, antibacterial agents, or cleaning agents. By way of a non-limiting examples, the adhesive gels could be utilized as toilet-bowl cleaners, where the gels are adhered to a toilet bowl and controllably release cleaning agents. As another non-limiting example, the adhesive gels can be adhered to medical implants and controllably release antibacterial agents. As another non-limiting example, the adhesive gels can be adhered to catheters and controllably release agents to prevent the formation of biofilm. As another non-limiting example, the adhesive gels can be used in a buccal patch that adheres to the inside of an animal's mouth and controllably release drugs. The release of drugs or other payload molecules from the adhesive gels can be pH-triggered or sustained release, which can last for multiple weeks. A pH-triggered release of molecules can be effected by altering the pH above about 10 or below about 4, so as to dissolve the ionically crosslinked adhesive gels and form dispersions or solutions that release the payload molecules that were blended with, incorporated into, or diffused into the adhesive gels.

Following adhesion to a surface, the non-adhered surface of an adhesive gel described herein can be coated with a polymer or other substance so as to make the non-adhered surface non-adhesive. In this manner, the adhesive gels can be utilized for applications where a one-sided adhesive is desirable. As one non-limiting example, the adhesive gels can be adhered to the hull of a boat and be used to prevent the adhesion of barnacles to the boat hull by being non-adhesive on the side not adhered to the boat hull.

Embodiments of the present disclosure further include methods of determining coverage or denial of health insurance reimbursement and/or payment for treatments of disease or injury comprising using the adhesive gels described herein. In certain embodiments, the treatment comprises the use of an adhesive gel made from a polyamine and a multivalent phosphate crosslinker, and a provider of health insurance denies coverage or reimbursement for the treatment.

Kits

The adhesive gels and methods described herein can be embodied as parts of a kit or kits. A non-limiting example of such a kit comprises the ingredients for preparing an adhesive gel, namely a polyamine and a multivalent phosphate crosslinker, in separate containers, where the containers may or may not be present in a combined configuration. Many other kits are possible, such as kits comprising a pre-mixed dispersion of polyamine and multivalent phosphate crosslinker in acidic or basic pH in one container and a pH modifier in another container. In certain embodiments, the kits further comprise a syringe. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

Example I

Materials

Millipore Direct-Q 3 deionized water (18.2 MΩ·m) was used in all preparations. PAH (nominal molecular weight≈120-200 kDa) and PVAm (nominal molecular weight≈25 kDa) were purchased from Polysciences, Inc. (Warrington, Pa.). PPi and TPP (both sodium salts) were obtained from Sigma-Aldrich (St. Louis, Mo.). Hydrochloric acid (HCl) and sodium hydroxide (NaOH) were purchased from Fisher Scientific (Fair Lawn, N.J.) and VWR (West Chester, Pa.), respectively. The glass, PMMA, and Teflon® plates used for adhesion tests were cut from Fisherfinest premium microscope slides (Fisher Scientific), and OPTIX 0.093"-thick clear acrylic sheet, and a 0.25"-thick sheet of polytetrafluoroethylene, respectively. All materials were used as received.

Phase Studies

PAH/PPi and PAH/TPP mixtures were prepared by mixing PAH and multivalent counterion stock solutions, whose pH was adjusted to 7.0 using NaOH and HCl. The parent PAH solutions ranged between 0.016 wt % and 0.16 wt % (1.7-17.1 mM) in concentration, and were mixed with different volumes (40-400 µL) of PPi and TPP solutions, where the parent PPi solution concentrations varied between 0.16 and 1.6 wt % (5.4-54.1 mM), and the parent TPP solution concentrations varied between 0.16 wt % and 1.6 wt % (4.4-43.5 mM). The cuvettes were then shaken for approximately 2 seconds and allowed to equilibrate for one month. During equilibration, DLS (Zetasizer Nano ZS; Malvern, UK) was used to detect the formation and coagulation of colloidal dispersions. A sudden increase in the light scattering intensity indicated the formation of colloidal dispersions. Similarly, a drastic increase in the colloid hydrodynamic diameter and polydispersity (and visible macroscopic precipitation) indicated the coagulation of colloidal complexes into adhesive gels. These DLS measurements were performed using non-invasive back-scattering (NIBS) detection at the 173° scattering angle.

Zeta Potential Measurements

The evaluation in the apparent ζ-potential with the addition of PPi and TPP to PAH mixtures was tracked via electrophoretic light scattering using the Zetasizer Nano ZS instrument (where the ζ-potentials were estimated from the electrophoretic mobilities via the Smoluchowski equation). Here, 160 µL aliquots of either 0.37 wt % PPi or 0.40 wt % TPP were sequentially added to 10 mL of 0.04 wt % PAH solution while stiffing the mixtures at 800 rpm with cylindrical magnetic stir bars (10 mm×5 mm). The ζ-potential was measured after each addition, following 10 minutes of equilibration. Each titration was repeated thrice.

Rheology Measurements

Dynamic rheology was performed at room temperature using a Rheometric Scientific RDA III (Piscataway, N.J.) strain-controlled rheometer equipped with 25 mm parallel plates. The gel samples were prepared by slowly adding 26 mL of 3.9 wt % PPi solution or 15 mL of 5.7 wt % TPP solution to 1000 mL of 0.1 wt % PAH. The receiving PAH solutions were stirred at 300 rpm with cylindrical magnetic stir bars (5 cm×1 cm). The ionically-crosslinked complexes were allowed to coagulate for 3 days, whereupon the gels were scraped from the bottom of the beaker. The gels were then loaded into the rheometer, compressed to a 0.5 mm gap thickness, and allowed to relax between the plates until the normal force was below 100 g. The excess gel was removed using a spatula and water was applied to the exposed, outer edges of the gel to prevent drying. After performing strain amplitude sweeps to determine the linear viscoelasticity region, frequency sweeps were performed in triplicate at angular velocities raging 0.1-500 rad/s at a 1.0% strain amplitude. Additionally, the self-healing properties of the gels were tested by first breaking the gels using 0.1-200% strain sweeps (oscillation frequency=1 rad/s), and then tracking the recovery in G' at a 0.4% strain amplitude, at which the gel network was stable, at the same oscillation frequency. All rheological measurements were performed in triplicate.

Adhesion Tests

PAH/PPi and PAH/TPP gel samples for adhesion tests were prepared by slowly adding either 66 mL of 4.2 wt % PPi solution or 43 mL of 5.6 wt % TPP solution to 1000 mL of 0.3 wt % PAH (while magnetically stiffing at 300 rpm). The complexes were then allowed to coagulate for 3 days, whereupon the adhesive gels were scraped from the bottom of the beaker and used to adhere two 2.5 cm×2.5 cm substrate surfaces (glass, PMMA, and Teflon®). All substrate surfaces were super-glued onto custom-made Plexiglass brackets (using Loctite® Glass Glue for the glass substrate and Gorilla® Super Glue for the PMMA and Teflon® substrates), which allowed them to be clamped into the stress-strain analyzer. To adhere the plates, a 0.5-1.0 g piece of gel (a more precise application was difficult because the gel adhered to the spatula) was placed between the two plates and compressed for 3 hours using 24 kPa of pressure, which uniformly spread the gel over the entire adhesion area (in a 0.33-0.43 mm thick layer). After trimming the excess gel that was squeezed out, the adhered plates remained submerged in deionized water for 15-30 minutes, until a tensile bond test was performed using an Instron 4400R Universal Testing Machine (UTM; Norwood, Mass.). The adhered plates were then clamped into the grips of the UTM and separated at a cross-head speed of 0.85 mm/s while measuring both the force and displacement.

Results

Figure 12A:
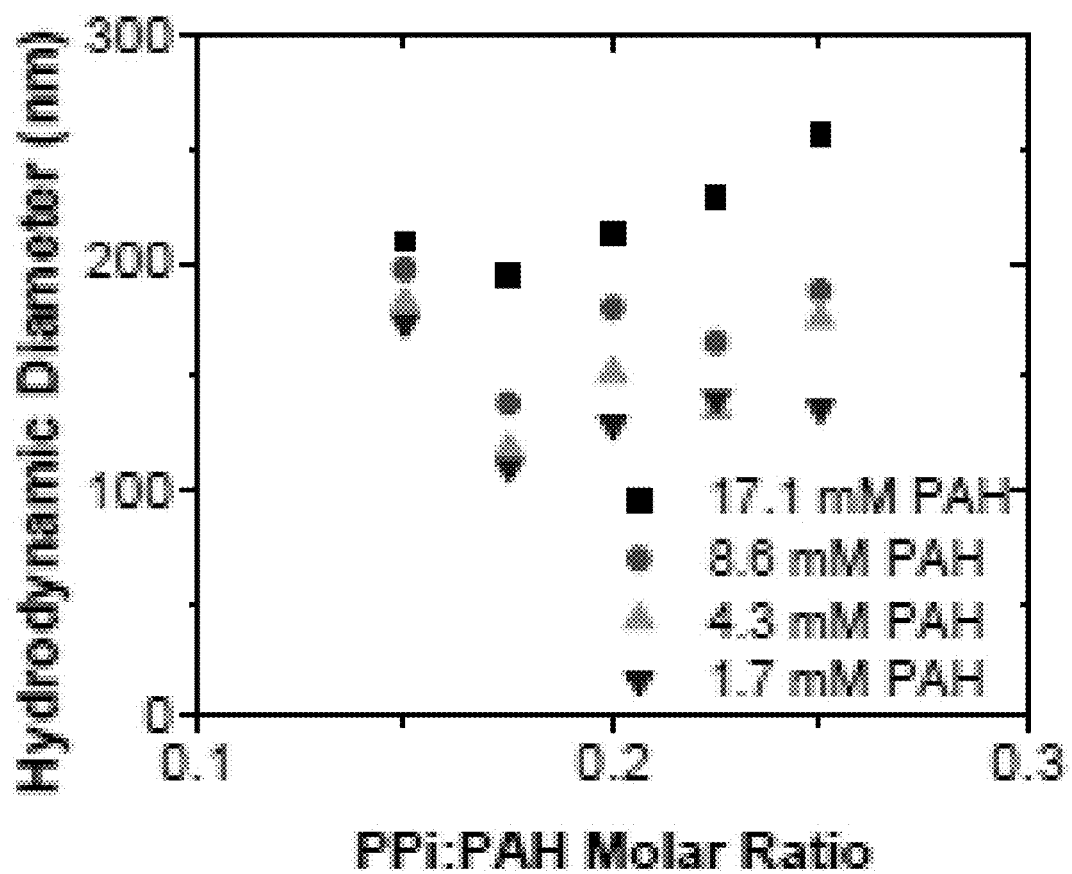
FIGS. 12A-12D: Plots comparing the z-average hydrodynamic diameters (FIGS. 12A-12B) and PDI-values (FIGS. 12C-12D) of the PAH/PPi and PAH/TPP colloidal complexes (plotted as a function of the ion:monomer molar ratio) at various PAH monomer concentrations.
Figure 12B:
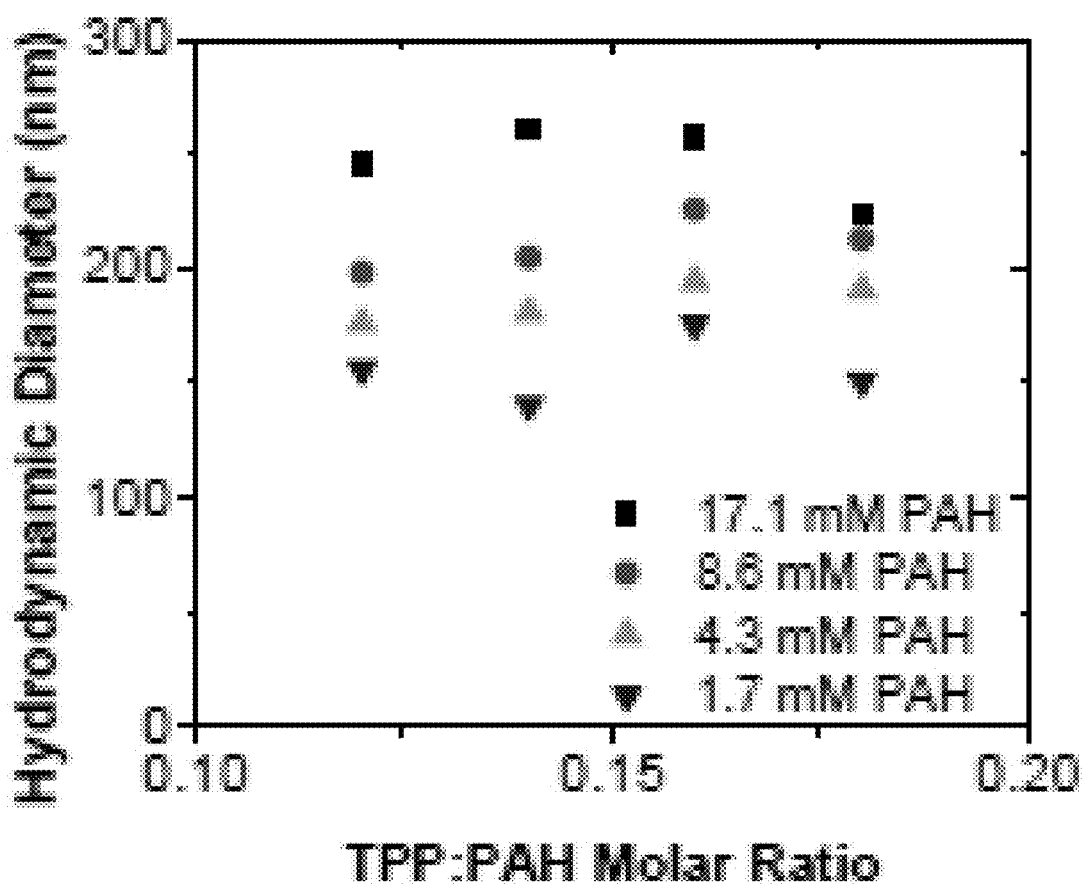
Figure 12C:
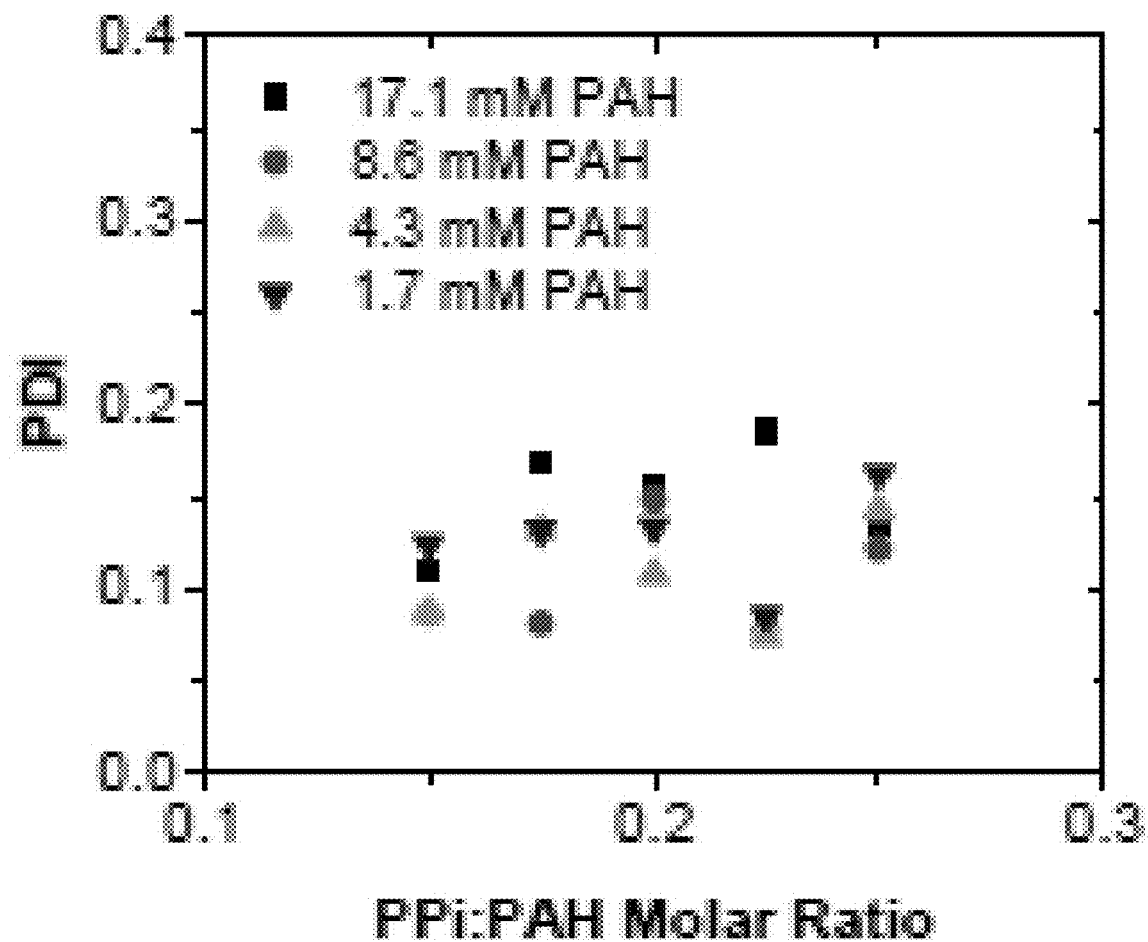
Figure 12D:
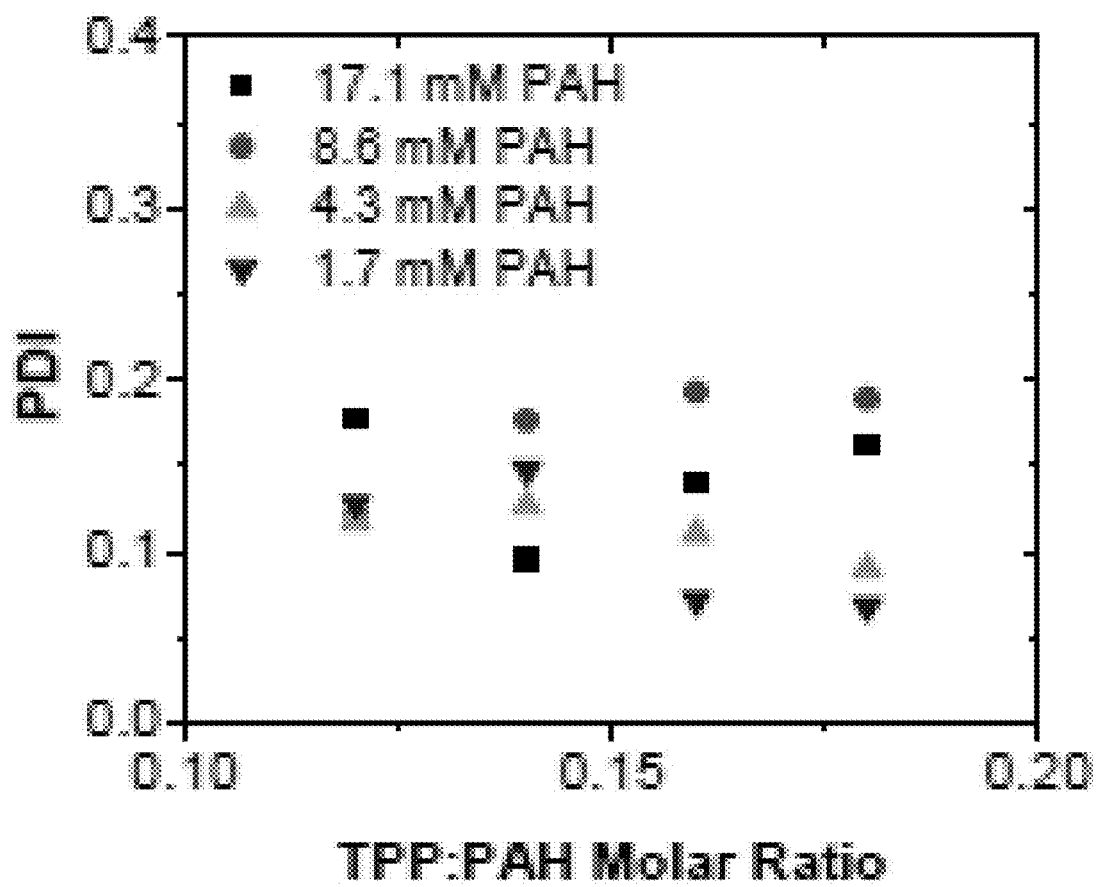

To characterize the properties of the gels, the phase behavior, rheology, and adhesion properties of the PAH/PPi and PAH/TPP mixtures were examined. When PAH was mixed with PPi or TPP at pH 7.0, its phase behavior (recorded after 1 month of equilibration) depended on the PAH multivalent ion:PAH monomer ratio. At PPi:PAH molar ratios below 0.13:1, the PAH/PPi mixtures formed clear solutions ("S Region" in FIG. 1A). Above that point, PPi crosslinked the PAH and formed colloidal complexes ("D Region" in FIG. 1A). The DLS analysis of these dispersions revealed the stably-dispersed colloidal complexes have narrow size distributions (PDI≈0.1-0.2) and z-average hydrodynamic diameters ranging between roughly 100 and 250 nm. (See FIGS. 12A-12D.) These diameters increased with the PAH concentration and remained stable with time. (FIGS. 12A-12B.) The complexes had fairly narrow size distributions, with polydispersity indices (PDIs) ranging between roughly 0.1 and 0.2. (FIGS. 12C-12D.)

Figure 1C:
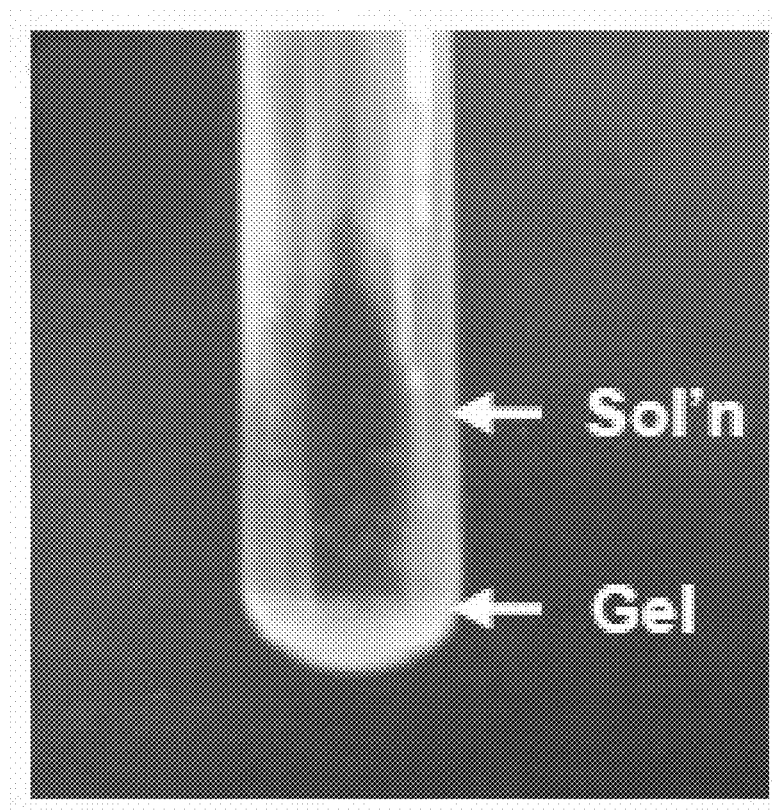
FIGS. 1C-1F: Photographs of the adhesive gels.
Figure 1D:
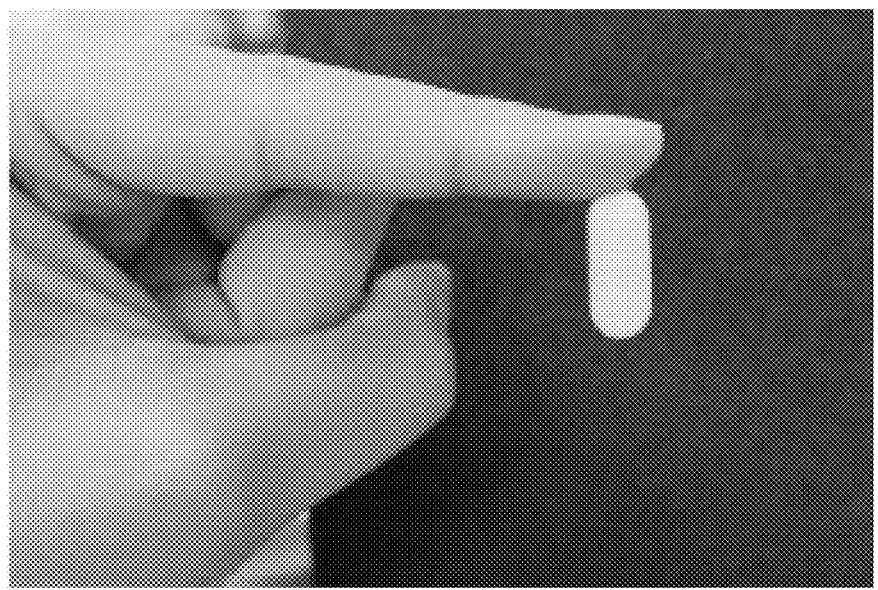
Figure 1E:
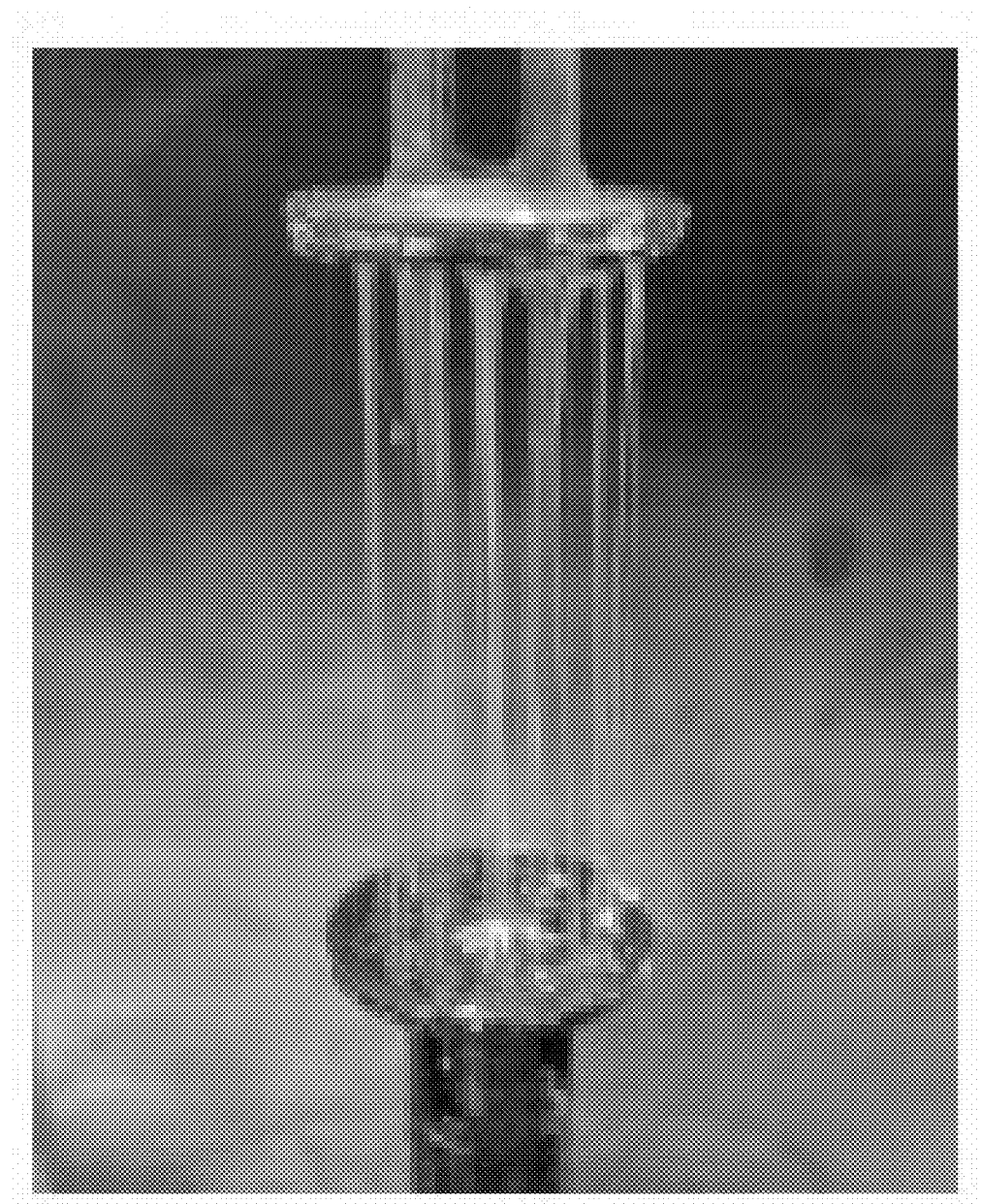
Figure 2A:
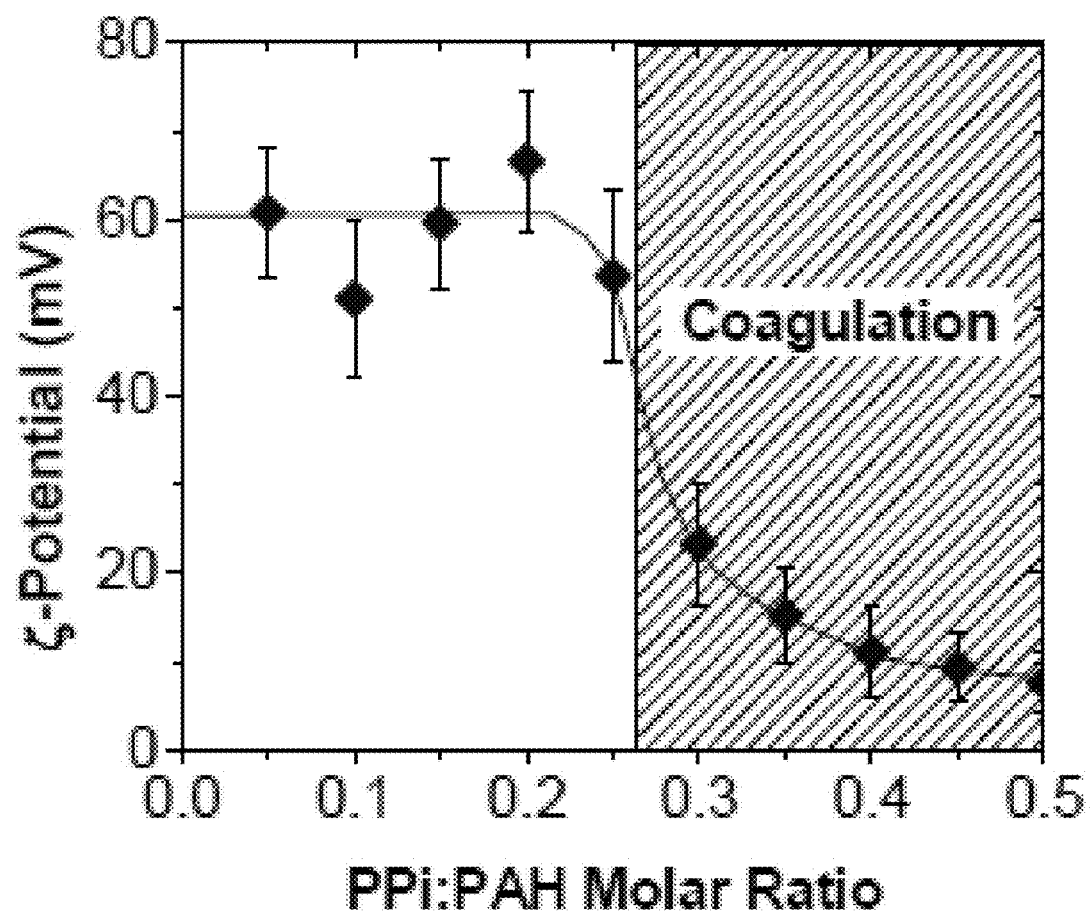
FIGS. 2A-2B: The evolution in PAH/PPi complex (FIG. 2A) and PAH/TPP complex (FIG. 2B) ζ-potentials plotted versus the ion:monomer molar ratio. The error bars are standard deviations, and the line is a guide to the eye. The shaded region indicates the composition where the colloidal complexes coagulate into macroscopic gels.

The stably-dispersed complexes maintained highly positive ζ-potentials (+50 mV to +70 mV; FIG. 2.) As the PPi:PAH molar ratio exceeded 0.25:1, however, a dramatic reduction in the ζ-potentials occurred, to +23 mV at the 0.30:1 PPi:PAH ratio and then +15 mV at the 0.35:1 PPi: PAH ratio, whereupon the ζ-potentials remained below +11 mV. At this point, the dispersions became destabilized and coagulated into macroscopic, sticky gel-like coacervates. (See FIG. 1C and "G+S Region" in FIG. 1A.) The macroscopic gel-like coacervates occupied a small fraction of the sample volume, and were in equilibrium with dilute supernatant solutions. These gels were highly adhesive and bound to dissimilar substrates, such as glass, metal, human skin, and Teflon® (as shown in FIG. 1D, where a Teflon®-coated magnetic stir bar was adhered to a fingertip with the gel, and in FIG. 1E, where the same gel adhered to the metallic rheometer plates).

Figure 1B:
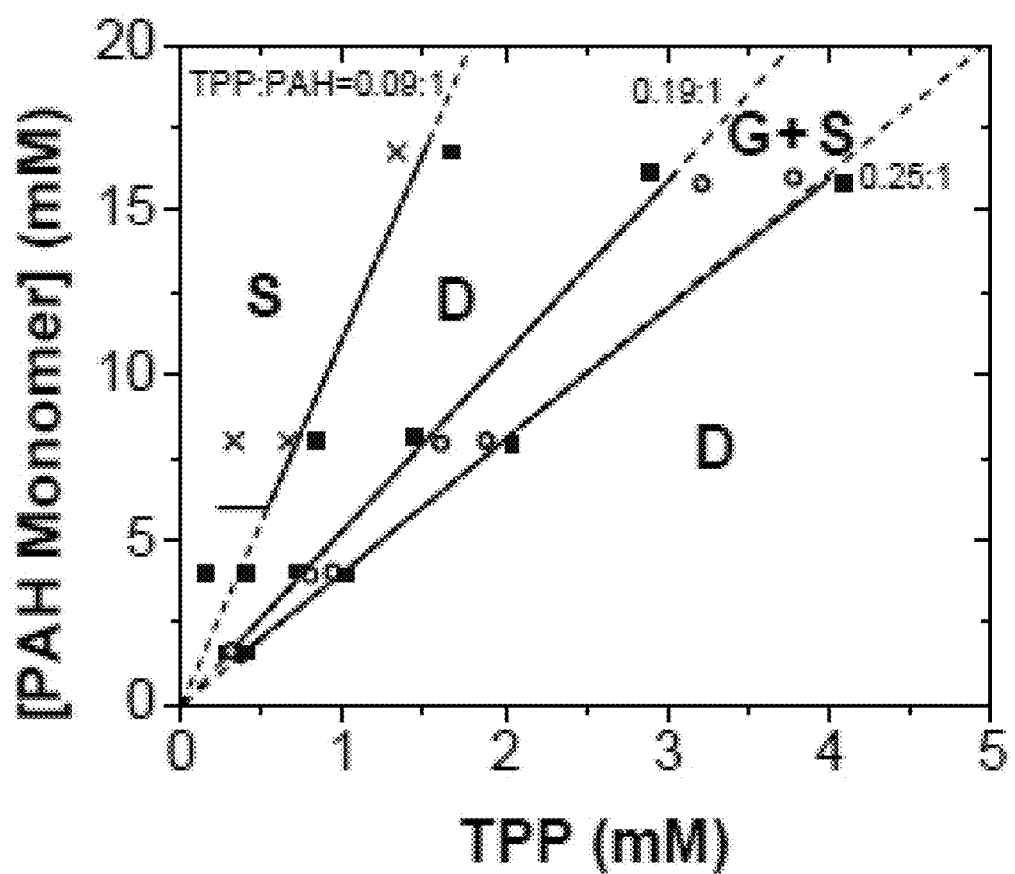
Figure 2B:
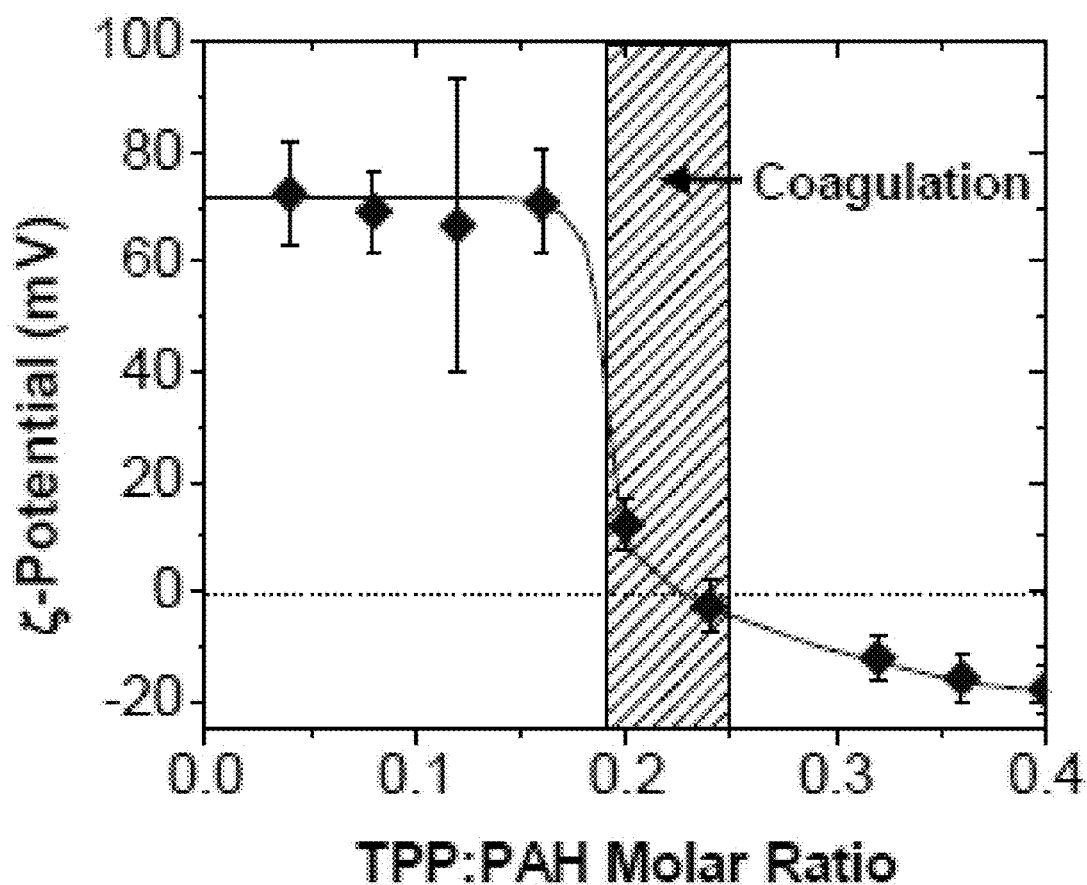
Figure 13:
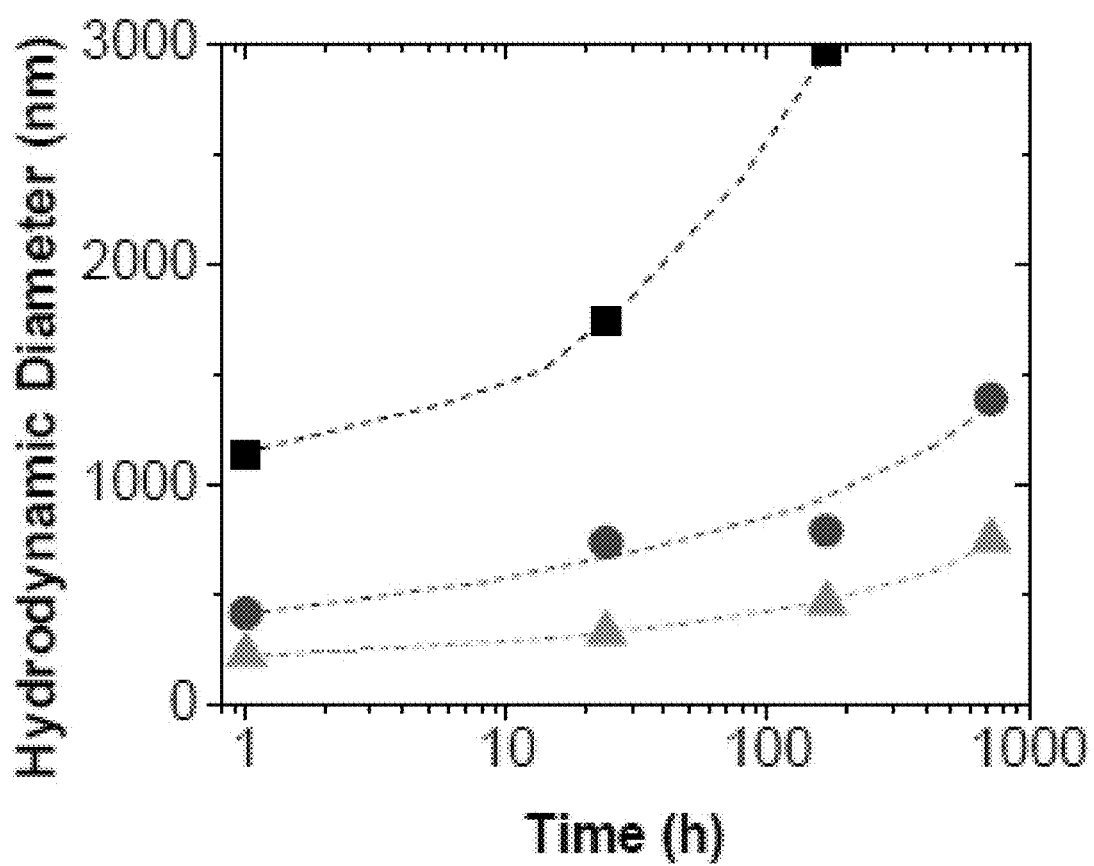
FIG. 13: Temporal size evolution of PAH/TPP complexes formed at 0.26:1 (■), 0.32:1 (●), and 0.4:1 (▲) TPP:PAH molar ratios. The lines are guides to the eye.

Similar to the PAH/PPi complexes, the PAH mixtures with pentavalent TPP underwent a progression from clear solutions to colloidal dispersions and adhesive macroscopic gel-like coacervates with an increasing TPP:PAH ratio (see FIG. 1B). Their complexation, however, exhibited two qualitative differences. First, unlike the PAH/PPi system, where stable colloidal complexes began forming only above the 0.11:1 PPi:PAH molar ratio, the onset of stable complex formation in the PAH/TPP system was sensitive to the PAH concentration; at higher PAH monomer concentrations (i.e., above 6±2 mM), stable colloidal complexes only formed above the 0.09:1 TPP:PAH molar ratio (FIG. 1B), while at lower concentrations, colloidal complexes form at TPP:PAH ratios as low as 0.02:1. Second, although at higher TPP concentrations (above the 0.19:1 TPP:PAH molar ratio) the PAH/TPP complexes coagulated into macroscopic gel-like coacervates (see the "G+S" region in FIG. 1B), no macroscopic gel-like coacervates formed during the month-long experiment where the TPP:PAH molar ratio exceeded 0.25:1 (FIG. 1B). Instead, the PAH/TPP mixtures formed colloidal dispersions with negative ζ-potentials, ranging between −10 mV and −20 mV (FIG. 2B). Over the month-long equilibration time, these negatively charged complexes slowly grew in size (see FIG. 13), indicating that the dispersions had lower colloidal stabilities than those formed at low ion:monomer molar ratios, and were only kinetically stable.

At the mixture compositions where macroscopic gels formed, the rates at which the PAH/PPi and PAH/TPP dispersions coagulated into gels were sensitive to the PAH concentration, ion:monomer molar ratio and stiffing speed. At low PAH concentrations (e.g., 0.016 wt %), the coagulation was slow and occurred over multiple days. Conversely, at higher PAH concentrations, such as those used to prepare samples for the rheology and adhesion tests (i.e., 0.10-0.30 wt %), most of the gel phase formed within minutes. This rapid gel formation, however, was followed by a second, slower stage, where the remaining colloidal complexes (whose concentration was now quite low) required 2-3 days to fully coagulate. Similarly, the coagulation rates were accelerated by stirring and the use of ion:monomer ratios where the ζ-potentials were near zero.

Once formed, both the PAH/PPi and PAH/TPP gel-like adhesives contained only 25-30 wt % water. This water content indicated very dense network structures and (within the limits of the "S+G" region in FIGS. 1A-1B) was insensitive to the PAH and ionic crosslinker concentrations. Thus, the gel-like coacervate phase composition remained roughly constant with the overall polymer and crosslinker concentration, and, because virtually all of the PAH was in the gel-like coacervate phase, the amount of adhesive formed scaled linearly with the concentration of the parent PAH solution. Furthermore, the final adhesive gel properties were insensitive to the mixing procedure used in their preparation. This insensitivity to the mixing method and ability to form the adhesive gels rapidly (i.e., at the higher PAH concentrations) indicate that the adhesive gel preparation process can easily be scaled up.

Gel formation was not analyzed in terms of the ion: monomer charge ratios due to the uncertainty of the ionization states of PPi and TPP. While the $pK_a$'s of PPi ($pK_{a,2}$=2.3, $pK_{a,3}$=6.6, and $pK_{a,4}$=9.3) and TPP ($pK_{a,3}$=2.8, $pK_{a,4}$=6.5, and $pK_{a,5}$=9.2), and effective $pK_a$ of PAH, are known in solution, the acid-base equilibria invariably shift towards the ionized states when the PPi and TPP bind to the PAH. FIGS. 1A-1B indicate that the onset of gel formation occurred at near-stoichiometric charge ratios. Without wishing to be bound by theory, it is believed that PAH, PPi, and TPP are fully ionized at pH 7. However, as seen from FIGS. 10A-10B, the gel-like complexes can form over a broader range of charge ratios depending on the ionic strength and possibly pH.

The gel-like properties of the macroscopic complexes (specifically, those formed using 0.33:1 PPi:PAH and 0.20:1 TPP:PAH molar ratios) were confirmed by dynamic rheology. Both the PAH/PPi and PAH/TPP complexes (FIGS. 2A-2B) had almost identical and frequency-independent storage moduli (G') that were consistently higher than the loss moduli (G") for the entire frequency (ω) range tested, thus confirming gel-like properties. The complexes had storage moduli and loss moduli that were quite high ($G'_\infty$~4× $10^5$ Pa; see FIGS. 3A-3B) compared to the majority of other physical (non-covalently crosslinked) gels, whose G' values are typically on the order of $10^3$-$10^4$ Pa. These high G'-values reflect the very dense ionic crosslinking, mediated by the high linear charge density of PAH and strong binding of PPi and TPP. These high values exceeded those obtained through the ionic crosslinking of PAH with weaker-binding citrate and phosphate ions. Likewise, these G'-values significantly exceeded those obtained from $Ca^{2+}$ and $Mg^{2+}$ crosslinked complex coacervates used in the biomimetic underwater adhesion strategies (whose G'-values are typically below $10^4$ Pa).

Figure 3A:
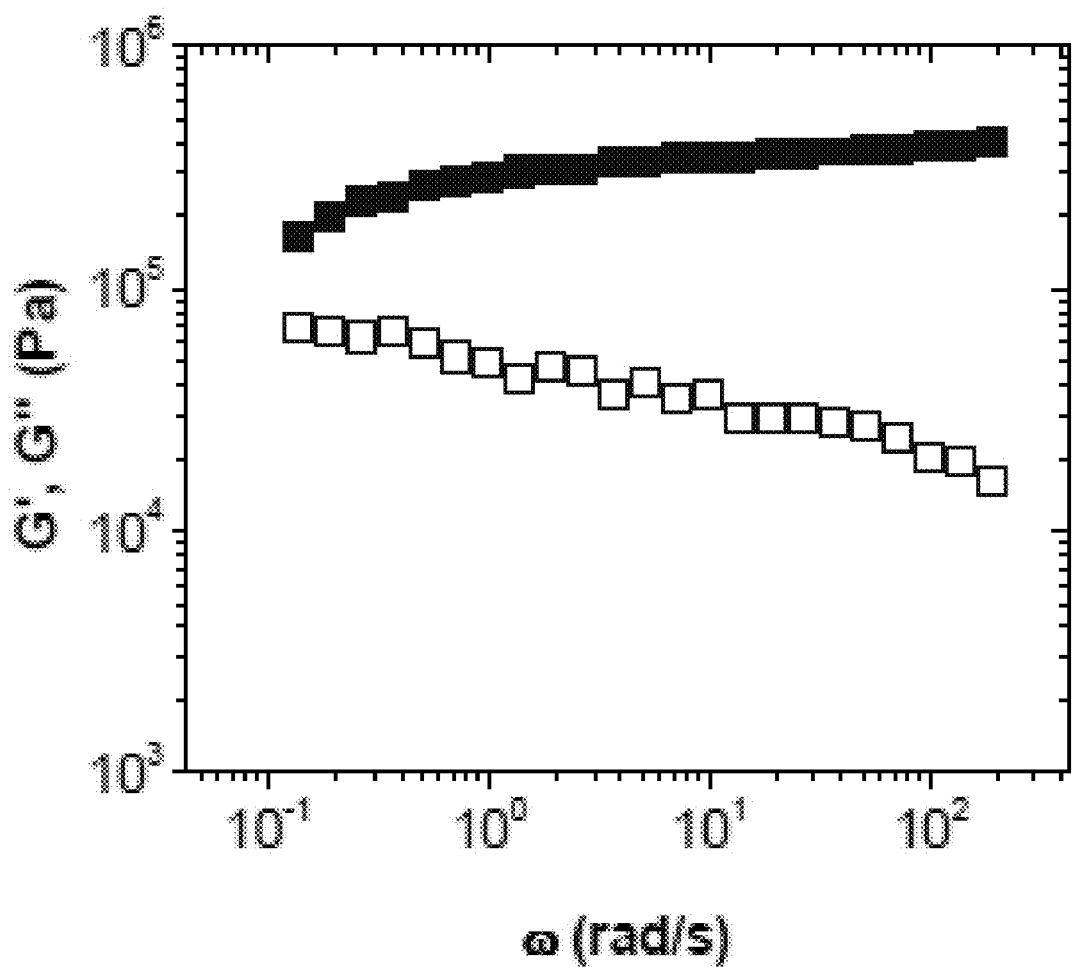
FIGS. 3A-3B: Frequency sweep data comparing the G' (■) and G" (□) of the PAH/PPi (FIG. 3A) and PAH/TPP (FIG. 3B) gels.
Figure 3B:
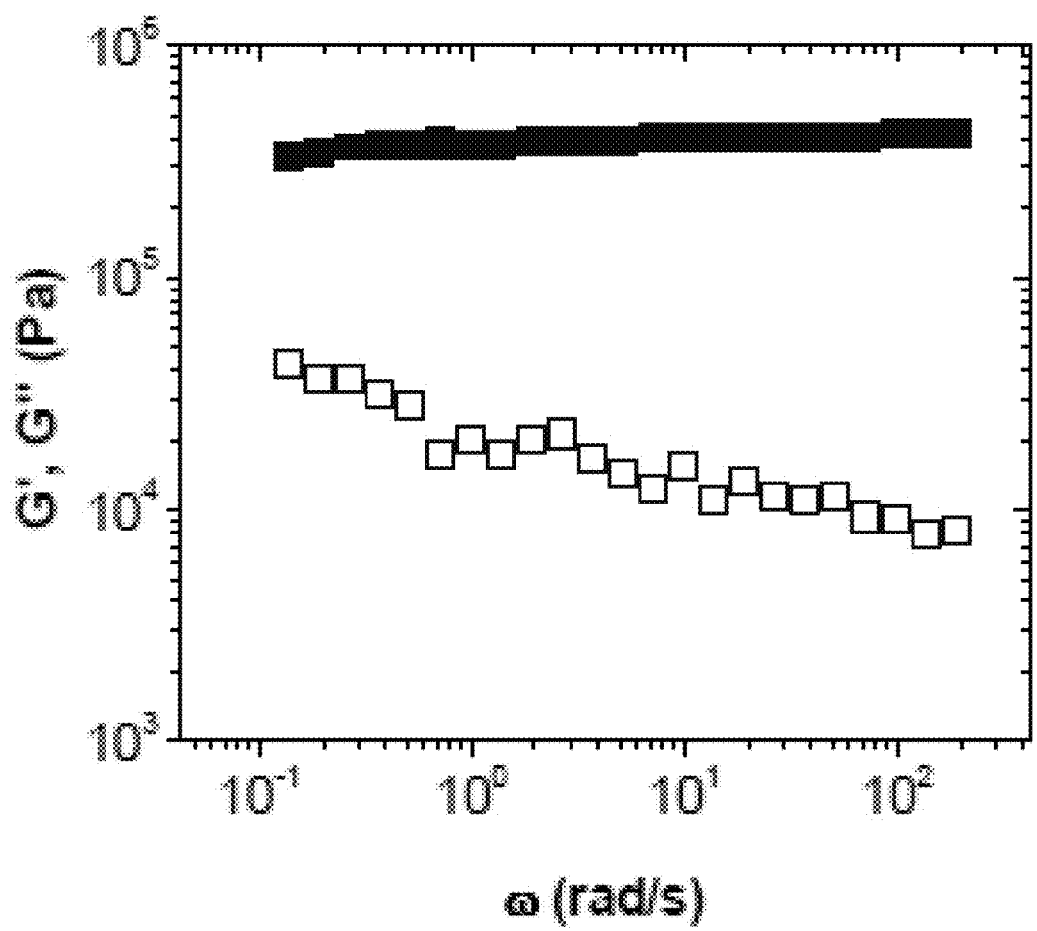
Figure 4A:
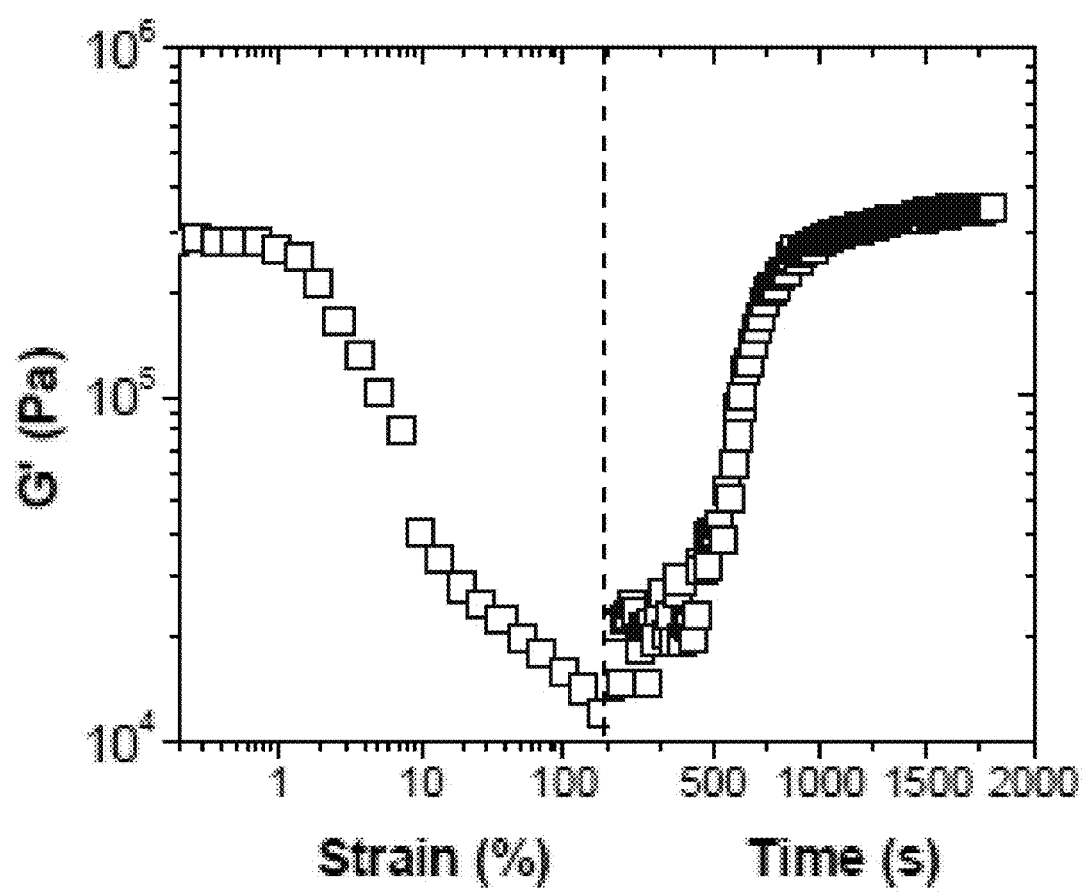
FIGS. 4A-4B: Representative dynamic rheology data illustrating the self-healing properties of the PAH/PPi (FIG. 4A) and PAH/TPP (FIG. 4B) gels.
Figure 4B:
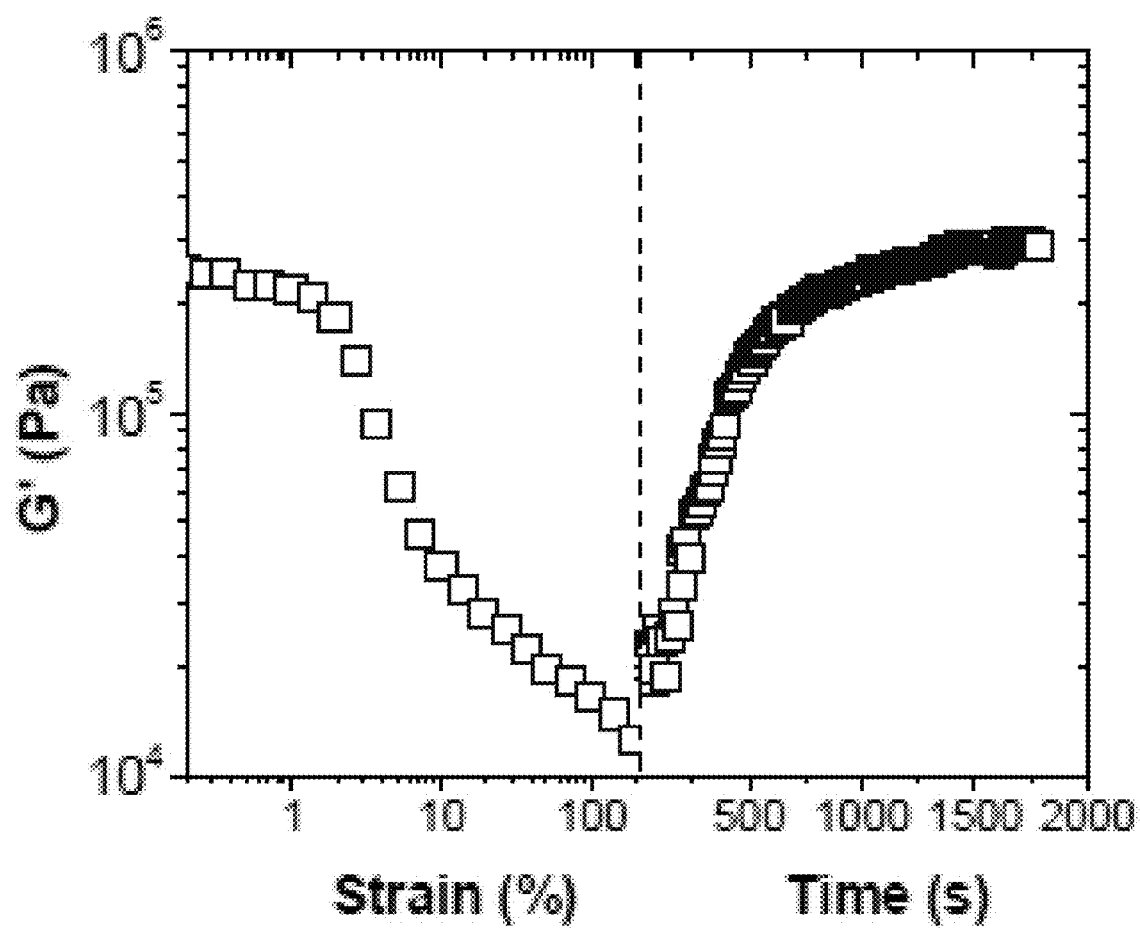

As seen in FIGS. 3A-3B, the G' and G" approach one another at lower oscillation frequencies, indicating that the G'/G" crossover would eventually occur at lower ω values. This indicates that, like other physical gels, these complexes undergo plastic deformation when stress is applied over long timescales (i.e., reflecting the reversibility of the ionic crosslinks) This reversibility allows the PAH/PPi and PAH/TPP networks to self-heal when torn, a property that was confirmed by dynamic rheology using a two-step procedure. Briefly, the gels were first broken by applying a 200% strain through a strain amplitude sweep, thereby breaking their network and causing their G' values to drop precipitously (FIGS. 4A-4B). The healing of the gel was then monitored over time by continuing to oscillate the gels at low (0.4%) strain amplitude, which was in the linear viscoelasticity region and did not disrupt the ionic network. As seen in FIGS. 4A-4B, all of the PAH/PPi and PAH/TPP samples recovered their original G' values within 10-30 minutes, although there was some variation in the recovery kinetics between the individual tests. The PAH/TPP networks healed slightly faster than the PAH/PPi networks.

Figure 1F:
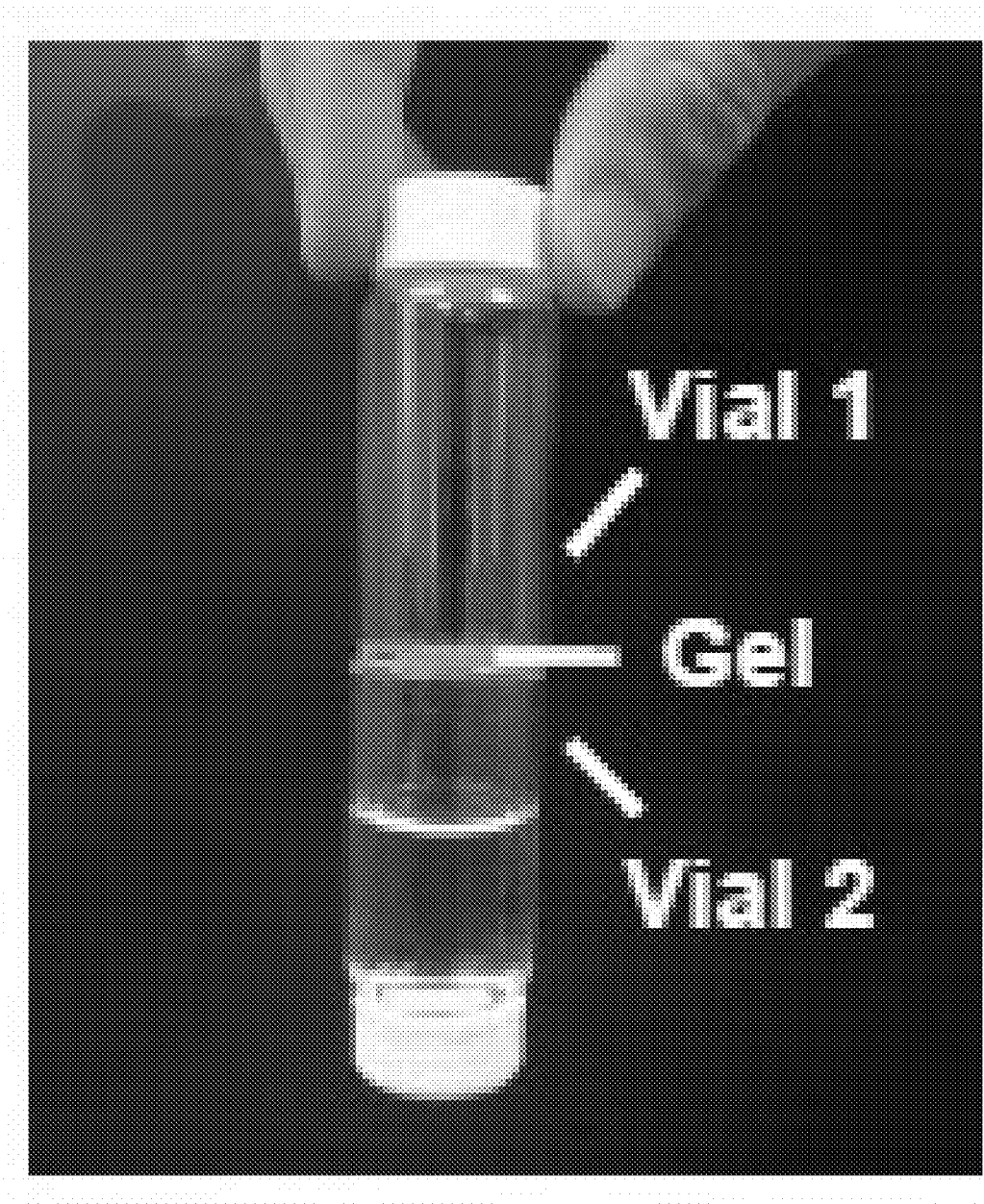

In addition to being self-healing, the gels were moldable, ductile, and adhesive (see FIGS. 1D-1F), even under water, which allows the ionically crosslinked polyamines to serve to pressure-sensitive underwater adhesives. Tensile-load tests were performed to quantify the ability of PAH/PPi and PAH/TPP gels to bond various dissimilar substrates. The adhesive gels were compressed between two flat plates made of either: (1) hydrophilic glass, (2) moderately hydrophobic poly(methyl methacrylate) (PMMA), or (3) very hydrophobic Teflon®. The adhesive application was performed under deionized water and a compressive pressure of 24 kPa for 3 hours. To prevent drying, the adhered plates were not removed from water until the adhesion strength was tested. The plates were then pulled apart at a rate of 0.85 mm/s while recording the force and displacement.

Figure 5A:
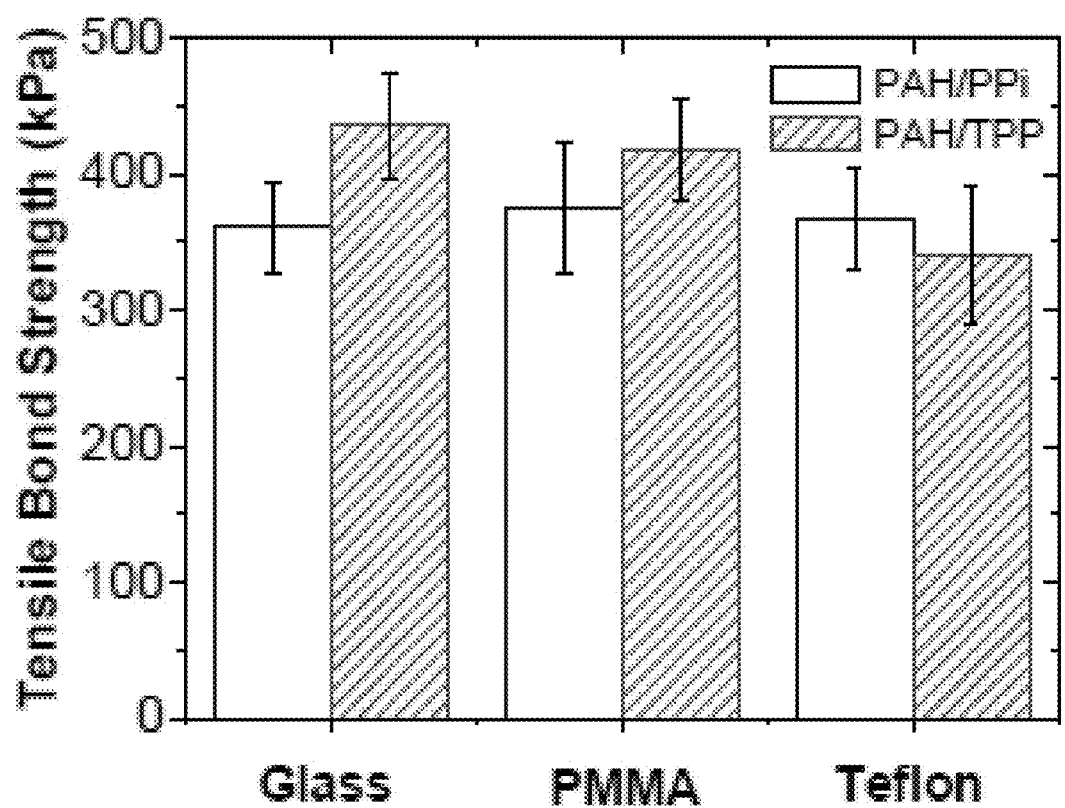
FIGS. 5A-5B: Average tensile bond strengths of PAH/PPi and PAH/TPP gels bonded to glass, PMMA, and Teflon® adhesion substrates (FIG. 5A), and the percentage of their initial bond strength retained plotted as a function of the adhesion/debonding cycle number obtained using glass substrates (FIG. 5B). The error bars show the standard deviations (n=6).

The adhesion strength achieved with the gels was insensitive to the substrate type and hydrophibicity, as seen in FIG. 5A. The PAH/PPi gels had very similar average tensile bond strengths regardless of the substrate being used (361 kPa for glass, 374 kPa for PMMA, and 366 kPa for Teflon®; see FIG. 5A). Likewise, the PAH/TPP gels provided only slightly higher tensile-bond strengths when adhered to glass (435 kPa) and PMMA (417 kPa) than when adhered to Teflon® (341 kPa). The tensile-bond strengths of these gels are roughly comparable to, if not better than, those of mussel and barnacle adhesion.

Despite the similarities in adhesion strengths, the modes of failure were substrate-dependent. When the PMMA and Teflon® substrates were used, the bonds failed at the gel/substrate interface. Conversely, when the glass substrate was used, the failure was cohesive. Therefore, without wishing to be bound by theory, although the gels yield stronger interfacial adhesion strengths when bonded to glass (relative to the PMMA and Teflon® substrates), the tensile bond strengths that the gels provide increase modestly because of their limited cohesive strengths.

Figure 5B:
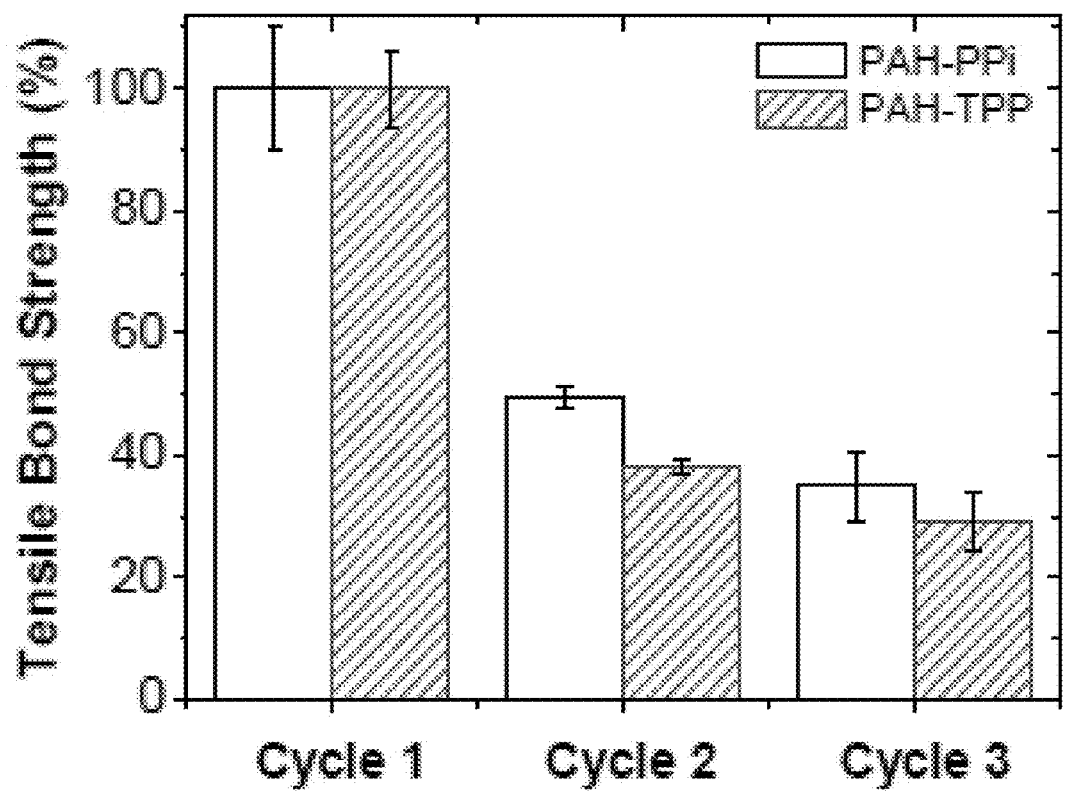

Additionally, while the reversibility of ionically crosslinked networks limits their ability to withstand sustained stress, the ability of the PAH/PPi and PAH/TPP gels to self-heal (shown in FIGS. 4A-4B) also allows them to partially regenerate their bonds if the bonds fail. This reversibility was quantified by separating glass plates adhered with the gels, then recompressing the plates again (using the same underwater procedure as in their initial adhesion), and then remeasuring their bond strength. As shown in FIG. 5B, after the initial gel failure and recompression, the gels recovered 30-40% of their original bond strength in the third adhesion/debonding cycle. This moderate reduction in tensile bond strength upon recompression reflects the introduction of defects into the network when the adhesive gels are reattached.

Figure 10A:
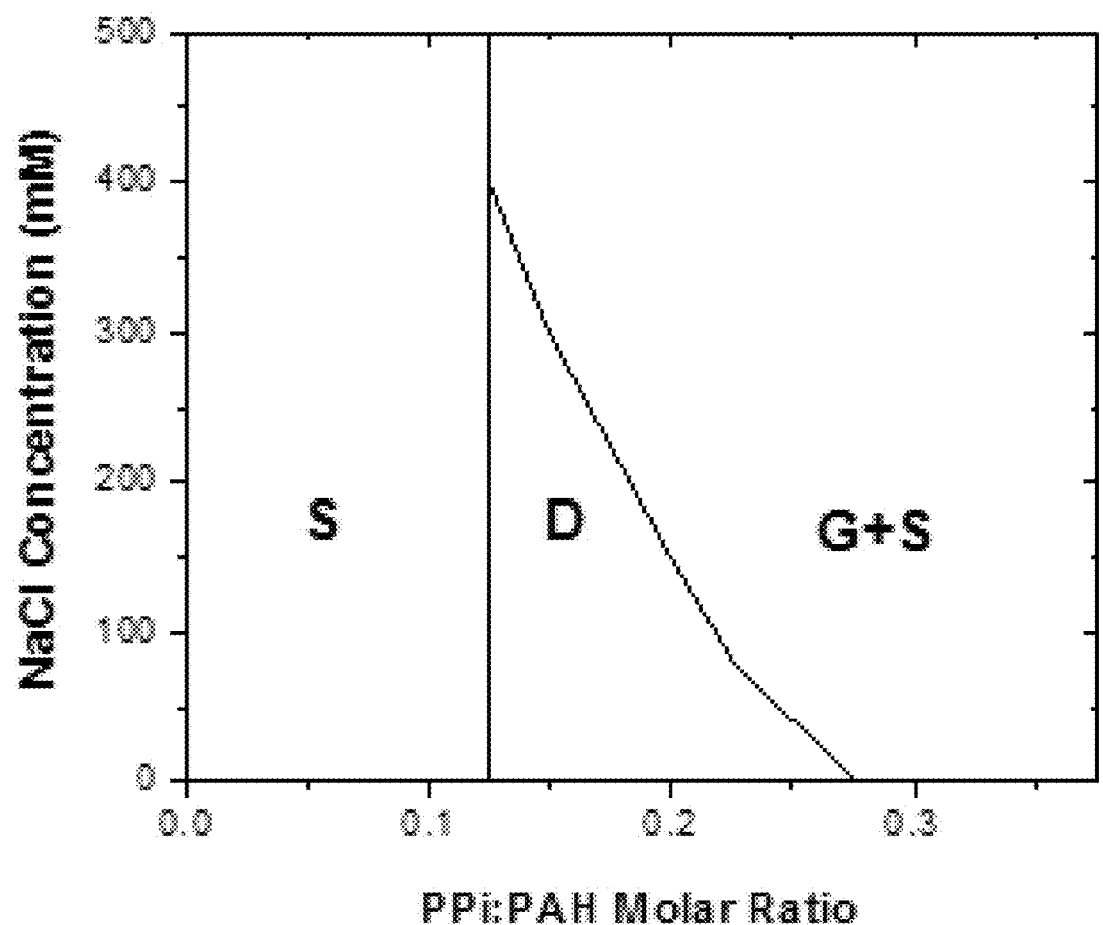
FIGS. 10A-10B: State diagrams at pH 7 showing the effect of NaCl concentration on PAH/PPi (FIG. 10A) and PAH/TPP (FIG. 10B).
Figure 10B:
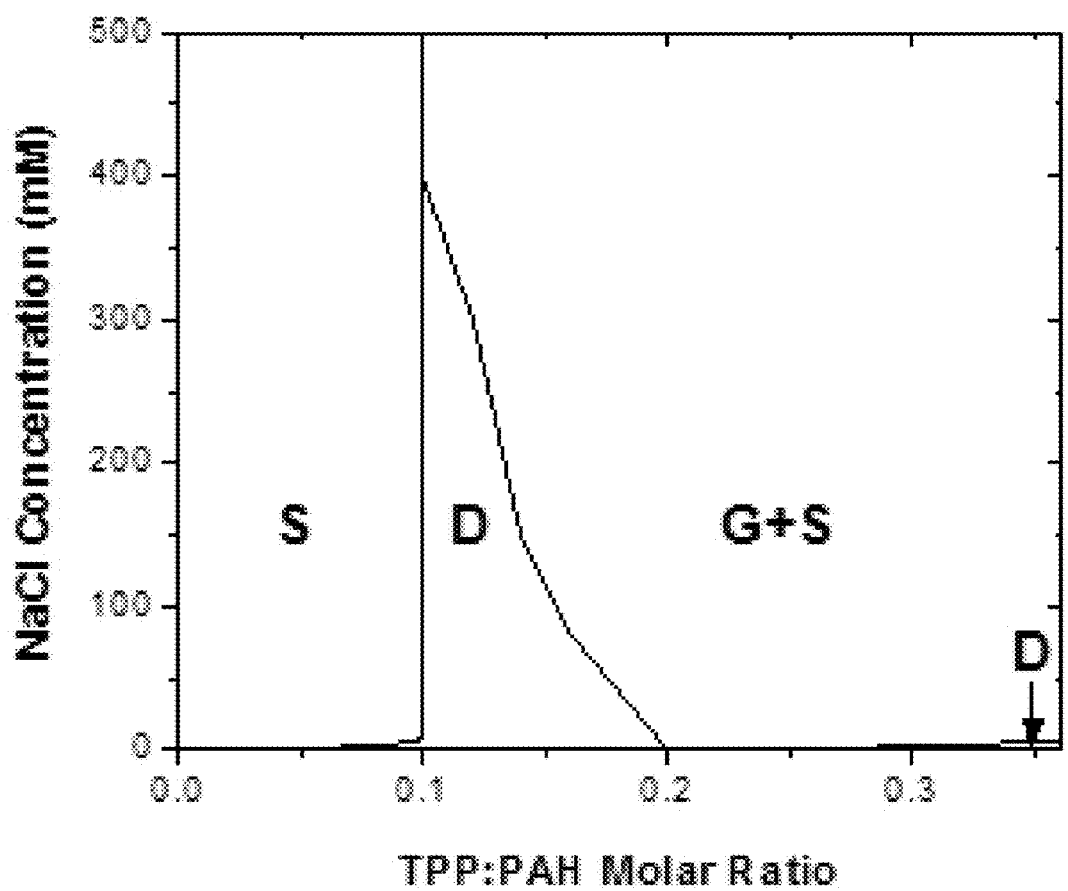
Figure 11A:
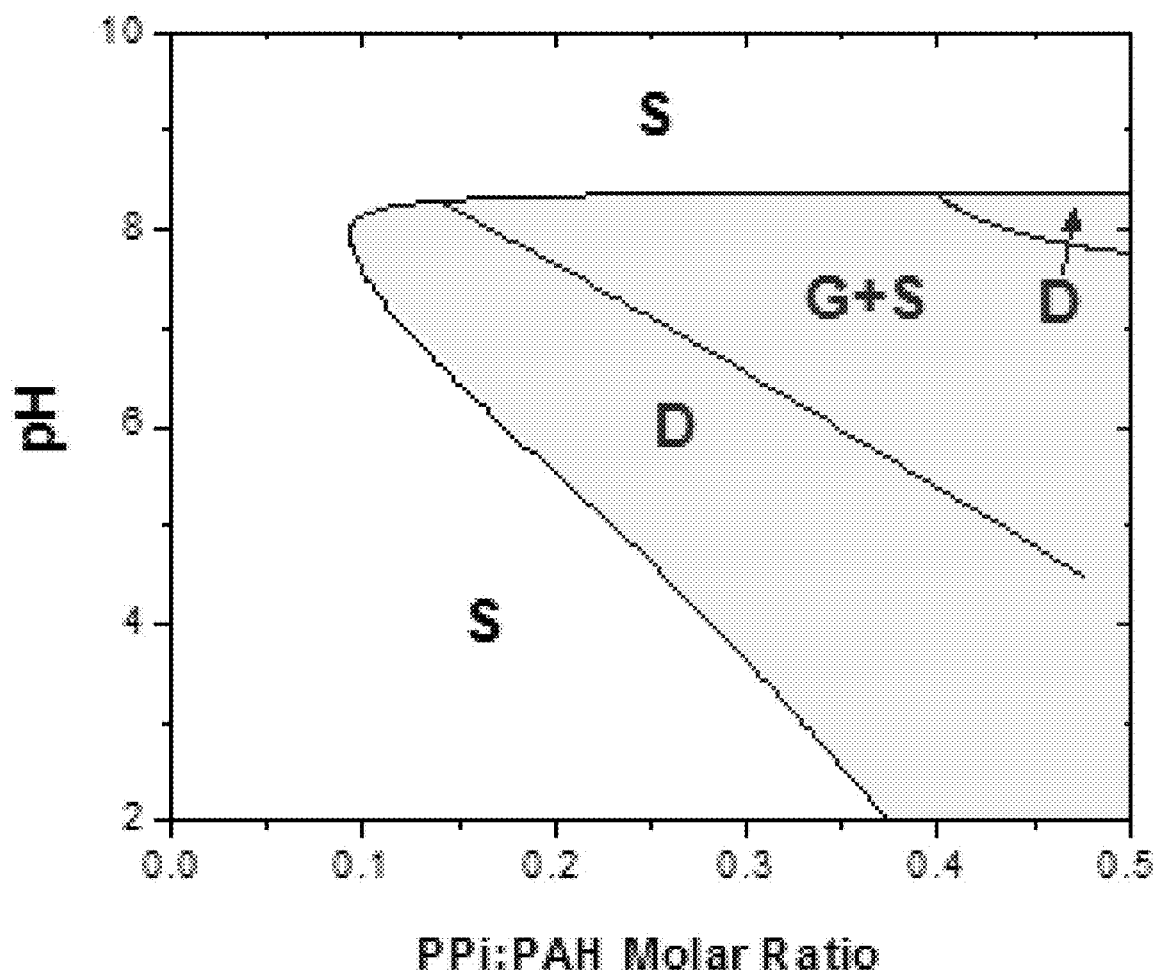
FIGS. 11A-11B: State diagrams showing the effect of pH on PAH/PPi (FIG. 11A) and PAH/TPP (FIG. 11B).
Figure 11B:
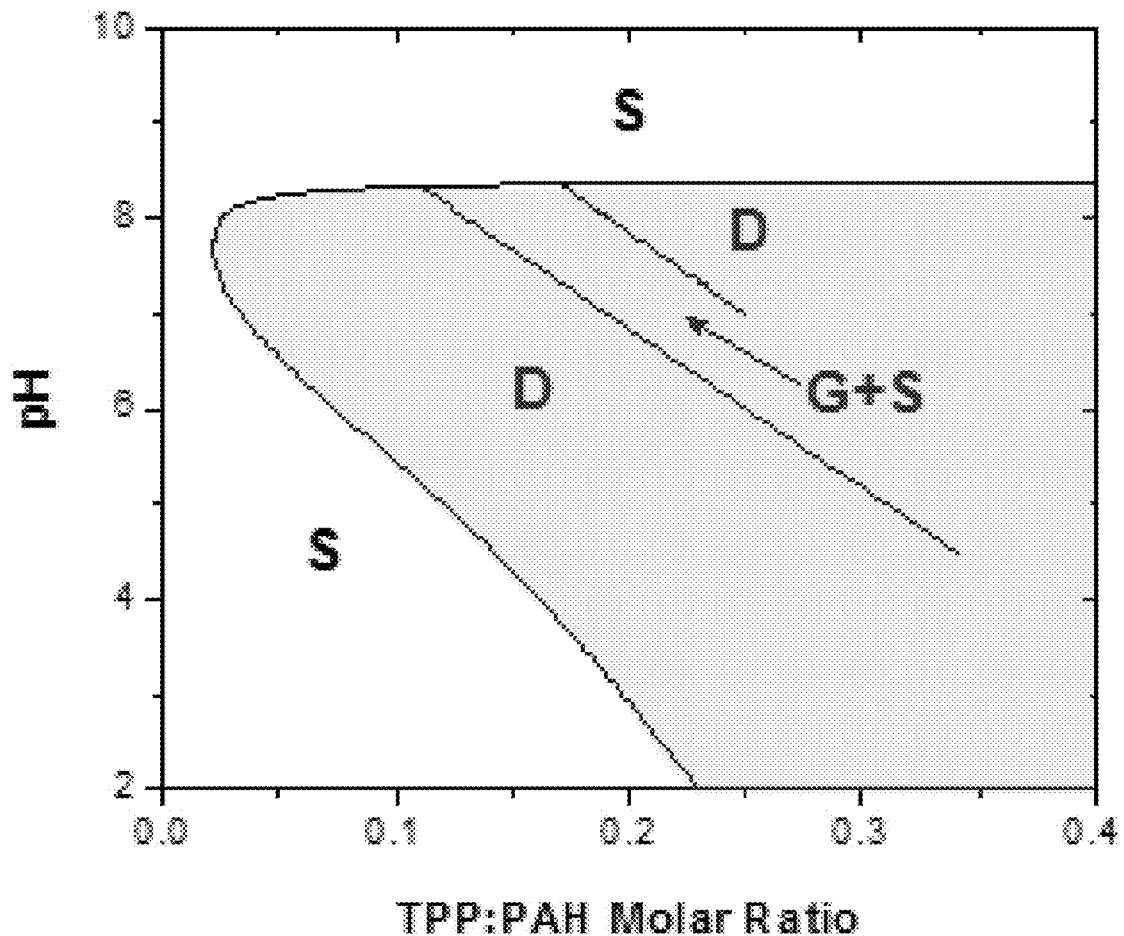

The adhesive gels were easily dissolved on demand by changing the pH because the ionization states of PAH, PPi, and TPP are pH-dependent. The adhesive gels were easily removed from laboratory equipment by raising the pH to 12, which quickly deprotonated the PAH amine groups and dissolved the ionic networks. Likewise, by protonating the PPi and TPP ions, the adhesive gels can be dissolved at low pH conditions. The effect of changing pH on the adhesive gels is shown in FIGS. 11A-11B. Complex formation was sensitive to pH, and occurred most readily near pH 7-8, due to the high ion and PAH charge. As seen in FIGS. 11A-11B, the complexes did not form at a pH greater than 8.5. This stimulus sensitivity is useful in situations where underwater adhesion needs to be reversed, and further distinguishes these ionotropic adhesive gels from covalently crosslinked gels. Furthermore, the PAH/PPi and PAH/TPP complexes did not dissolve in high ionic strength solutions, such as those containing 500 mM NaCl, although the ionic strength did affect their rheology. FIGS. 10A-10B show that the colloidal stability can be tuned with NaCl, which has little impact on the complex formation phase boundary but causes the dispersions to coagulate.

Payload Uptake and Release

Isothermal titration calorimetry (ITC) was used to characterize the binding of model payloads (Fast Green FCF and Rhodamine B dyes) to the PAH/PPi or PAH/TPP complexes (MicroCal VP-ITC, GE Healthcare, U.S.A). Colloidal PAH/PPi complexes were formed by adding 29.0 µl of 3.93 wt % PPi to 10.0 ml of 0.016 wt % PAH, and PAH/TPP complexes were formed by adding 19.0 µl of 5.84 wt % TPP to 10.0 ml of 0.016 wt % PAH. The Fast Green FCF and Rhodamine B solutions were then prepared at concentrations of 0.43 and 0.80 wt %, respectively. All solutions were adjusted to pH 7 using HCl and NaOH. ITC experiments were run by placing the PAH/PPi or PAH/TPP complex solutions in the sample cell, and loading the dye solution into the injector. The dye solutions were then titrated using twenty 15-µL injections, with 20 min equilibration intervals between each injection. The contents of the sample cell were stirred at 307 rpm with the impeller-shaped injector tip. The instrument software was used to integrate the raw ITC data obtained from these titrations. The heat of dilution, which was obtained by titrating the dye solutions into DI water, was then subtracted from the integrated data to obtain the final thermograms. To ensure reproducibility, each ITC test was repeated twice.

The dye-loaded coacervates were prepared by adding either 0.93 ml of 7.5 wt % PPi solution or 0.80 ml of 7.5 wt % TPP solution to 0.75 ml of 10.0 wt % PAH in a microcentrifuge tube (inner diameter: 1.0 cm) with all solutions containing one of the dyes (Fast Green FCF or Rhodamine B) at a concentration of 0.5, 1.0, or 4.0 mg/ml. All solutions were adjusted to pH 7 using HCl and NaOH prior to mixing. The mixtures were than centrifuged at 15,000 rpm for 90 min using an Ependorf centrifuge. This resulted in a gel-like plug at the bottom of the microcentrifuge tube approximately 7-8 mm thick with an aqueous supernatant above it. The loading capacity (LC) and loading efficiency (LE) for each loading procedure was calculated by subtracting the mass of dye in the supernatant from the total mass of dye originally in the solutions in the microcentrifuge tubes. The total dye mass in the supernatant was determined by measuring the supernatant mass in each tube and determining the supernatant dye concentration using UV-Vis spectroscopy (Varian Cary 50 Spectrophotometer) and the absorbance at a wavelength of 614 nm ($\epsilon=9.57\times 10^3$ m2/mol) and 555 nm ($\epsilon=9.82\times 10^3$ m2/mol) for Fast Green FCF and Rhodamine B, respectively. The LC and LE were then calculated using the following equations:

$$LC = \frac{V_t C_i - V_s C_f}{V_c} \times 100\% \quad \text{Equation 1}$$

$$LE = \frac{V_s C_f}{V_t C_i} \times 100\% \quad \text{Equation 2}$$

where Ci is the dye concentration in the parent PAH and PPi/TPP solutions, Cf is the final dye concentration in the supernatant, Vt is the solution total volume of solution initially added to the microcentrifuge tube, Vs is the supernatant volume recovered after centrifugation, and Vc is the total volume of coacervate after centrifugation.

Similarly, the LEs of the dye-loaded complexes was measured at a constant initial dye concentration of 1 mg/ml while the PAH concentration was varied. The dye-loaded complex samples were prepared as outlined above; however, the PAH concentration was varied (between 2.5 and 10.0 wt %). The concentrations of the counterion solutions were also varied (between 1.9 and 7.5 wt %) to keep the counterion: PAH molar ratio constant (0.33 PPi:PAH and 0.20 TPP:PAH). The LC- and LE-values were then determined using Equations 1 and 2.

The adhesive PAH/PPi and PAH/TPP complexes were prepared using the procedure described above, with and without dye. The initial mass of the complexes was measured by removing the supernatant from the microcentrifuge tube, measuring the mass of the microcentrifuge tube containing the adhesive complex, and then subtracting the mass of the microcentrifuge tube. The complexes were stored in 1 ml of 1×PBS with the PBS solution replaced daily, and weighed weekly using the same procedure used to determine their initial mass.

To characterize the release rates from PAH/PPi and PAH/TPP complexes, dye-loaded complexes were prepared using the procedure outlined above at an original Fast Green FCF or Rhodamine B concentration of 1.0 or 4.0 mg/ml (release measurements on complexes loaded with 0.5 mg/ml Fast Green FCF or Rhodamine B were not run). The supernatant was removed from the microcentrifuge tube, and the inside of the tube was rinsed with DI water to ensure all excess supernatant was removed. The release medium, 1 ml of 1×PBS, was then added to the microcentrifuge tube. During the release evaluations, the contents of the microcentrifuge tube was mixed at 400 rpm in an Ependorf Thermomixer at 37° C. The old PBS solution was replaced with fresh PBS daily. UV-Vis spectroscopy was used to determine the amount of dye released within this one day interval. The concentration of dye in the PBS was determined using the absorbance of the solution as described above. These release studies were run until the amount of dye released in one day became so low that a discernable peak in the UV-Vis spectrum could not be obtained. The weight of the adhesives was also tracked during the release process using the procedure described above. Each release experiment was repeated thrice to ensure reproducibility. An additional release study was run (using the same complex/dye compositions) with tap water at room temperature as the release medium.

Figure 7A:
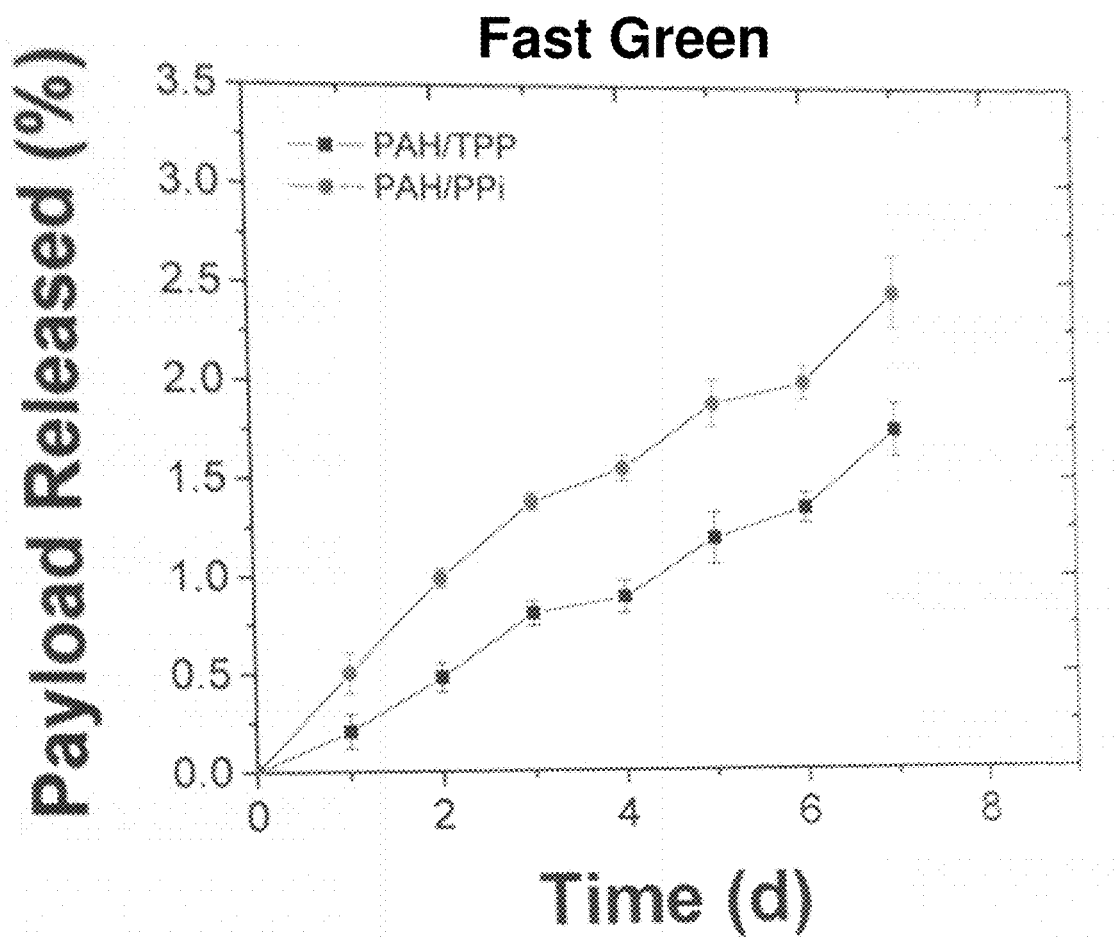
FIGS. 7A-7B: Sustained release over time demonstrated with Fast Green FCF (FIG. 7A) and Rhodamine B (FIG. 7B) dyes.
Figure 7B:
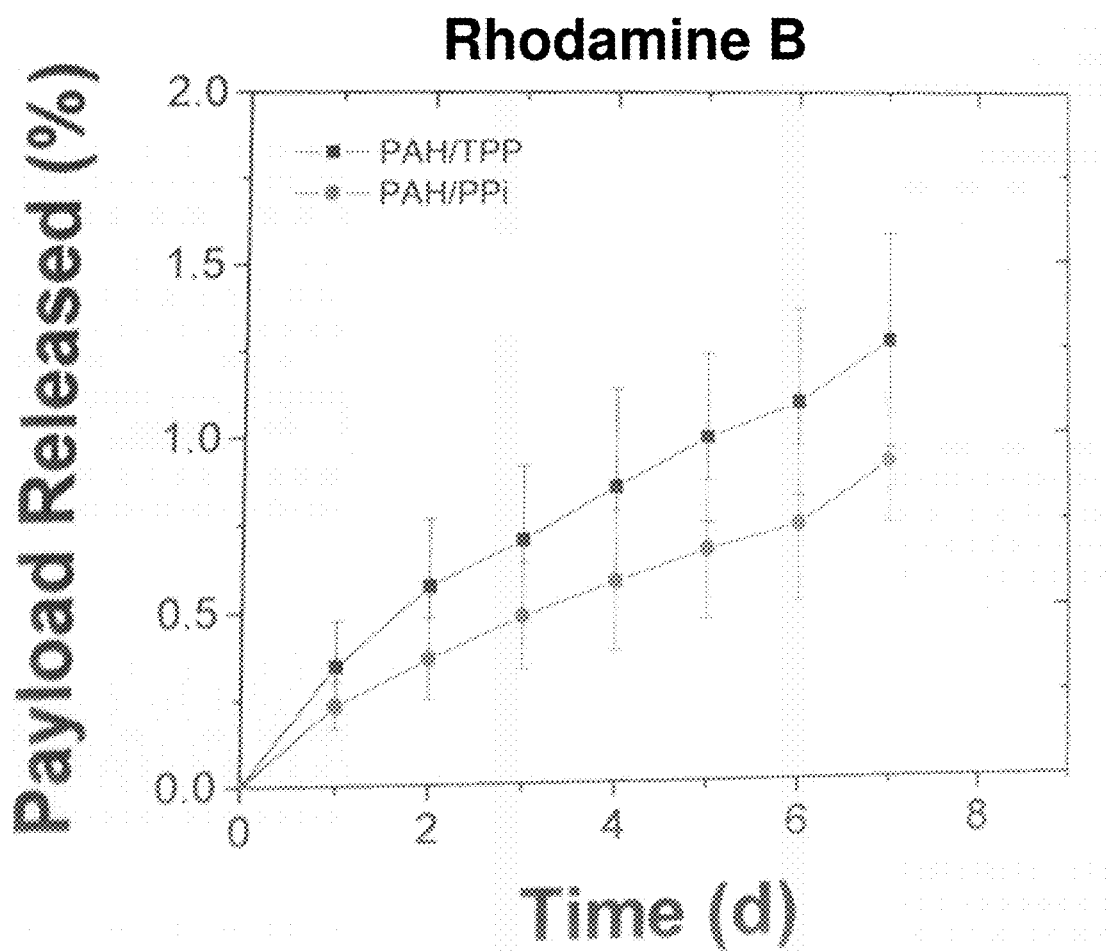

The long-term sustained release properties of the gels were examined using the small molecule dyes Fast Green FCF and Rhodamine B. As shown in FIGS. 7A-7B, only 1-2% of the payload was released in the first week, thus demonstrating the capability of the gels to take up and controllably release a payload over a long period of time.

Figure 24:
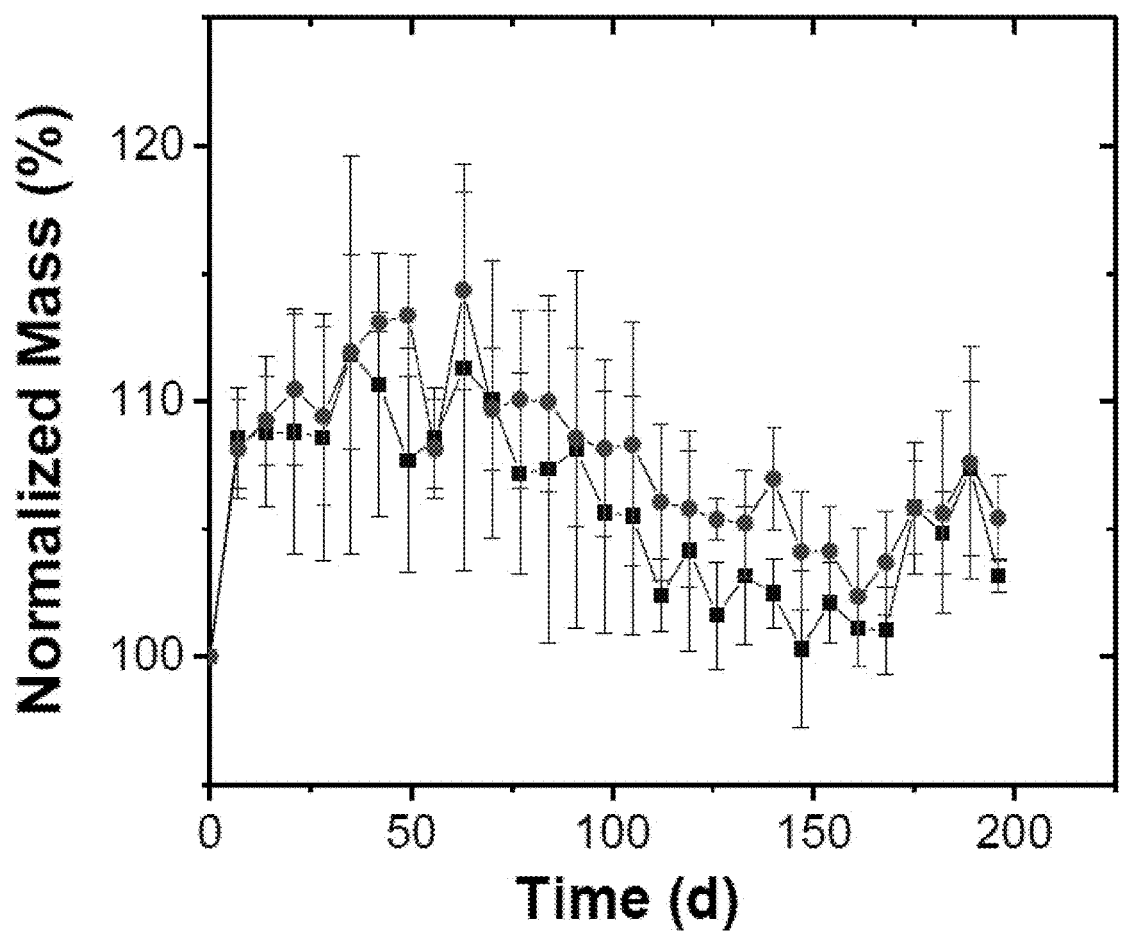
FIG. 24: The mass of the (■) PAH/PPi and (●) PAH/TPP adhesives, expressed as a percentage of their original mass and plotted as a function of time. The lines are guides to the eye. The error bars are standard deviations (n=3).

The degradation of the adhesive PAH/PPi and PAH/TPP adhesive coacervates in 1× phosphate buffered saline (PBS) at 37° C. (conditions mimicking those seen in the human body) was tracked for multiple months (see FIG. 24). The masses of the adhesive networks increased sharply to roughly 110% of their initial values after the first week (likely due to swelling). However, after this initial increase, the mass of PAH/PPi and PAH/TPP coacervates stayed roughly constant, exhibiting almost no change over 200 days. (FIG. 24.) This stable coacervate weight indicates that these coacervates degrade very slowly under physiological conditions.

Figure 25A:
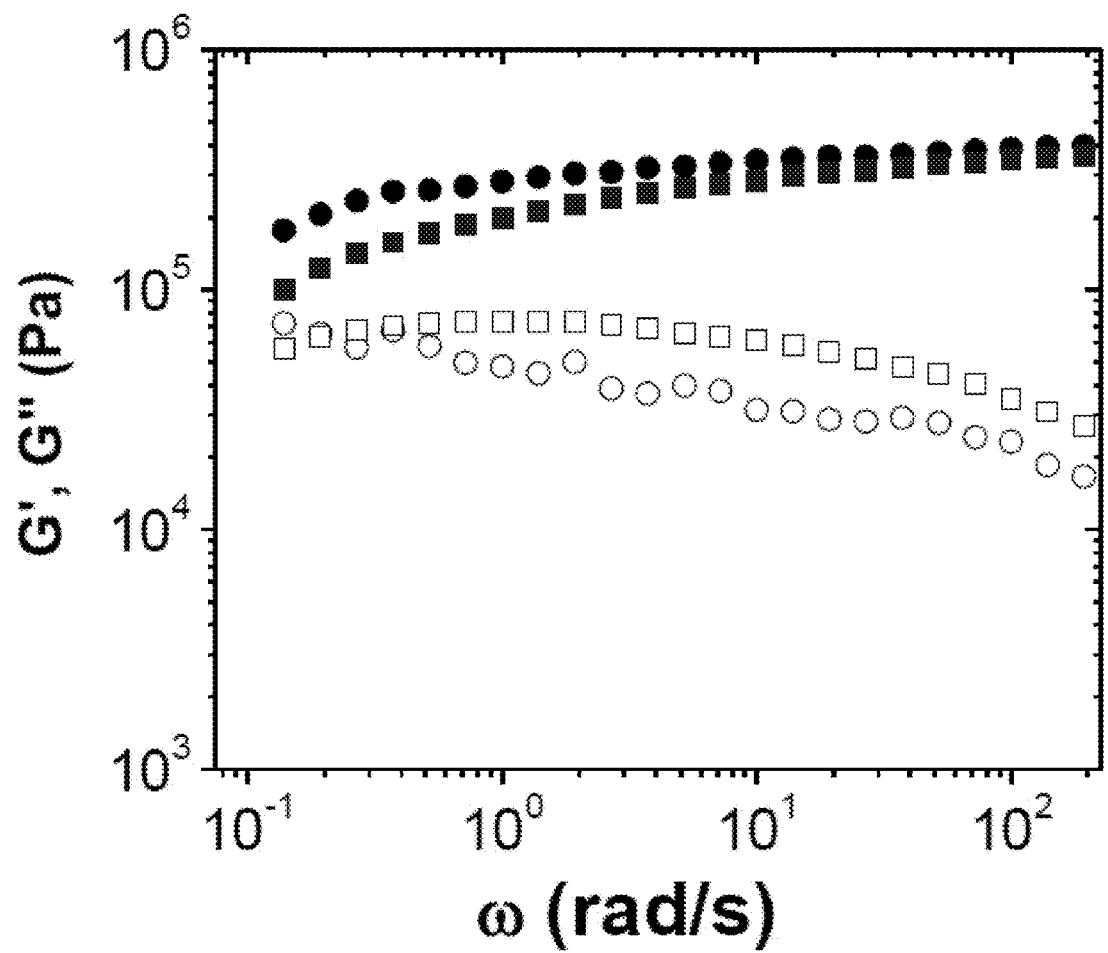
FIGS. 25A-25B: G' (closed symbols) and G" (open symbols) for PAH/PPi (FIG. 25A) and PAH/TPP (FIG. 25B) complexes tested (●, ○) immediately after preparation in DI water and (■, □) after being stored in PBS for 2 weeks.
Figure 25B:
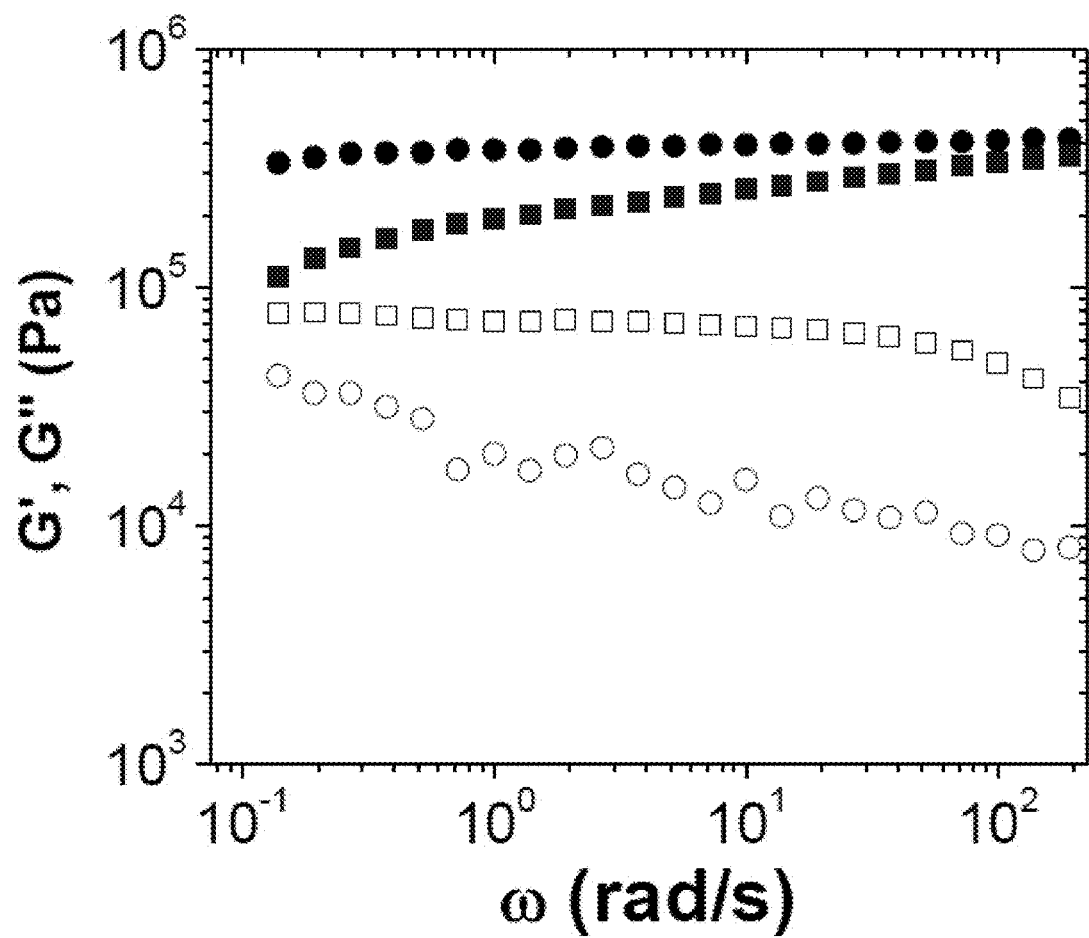
Figure 26A:
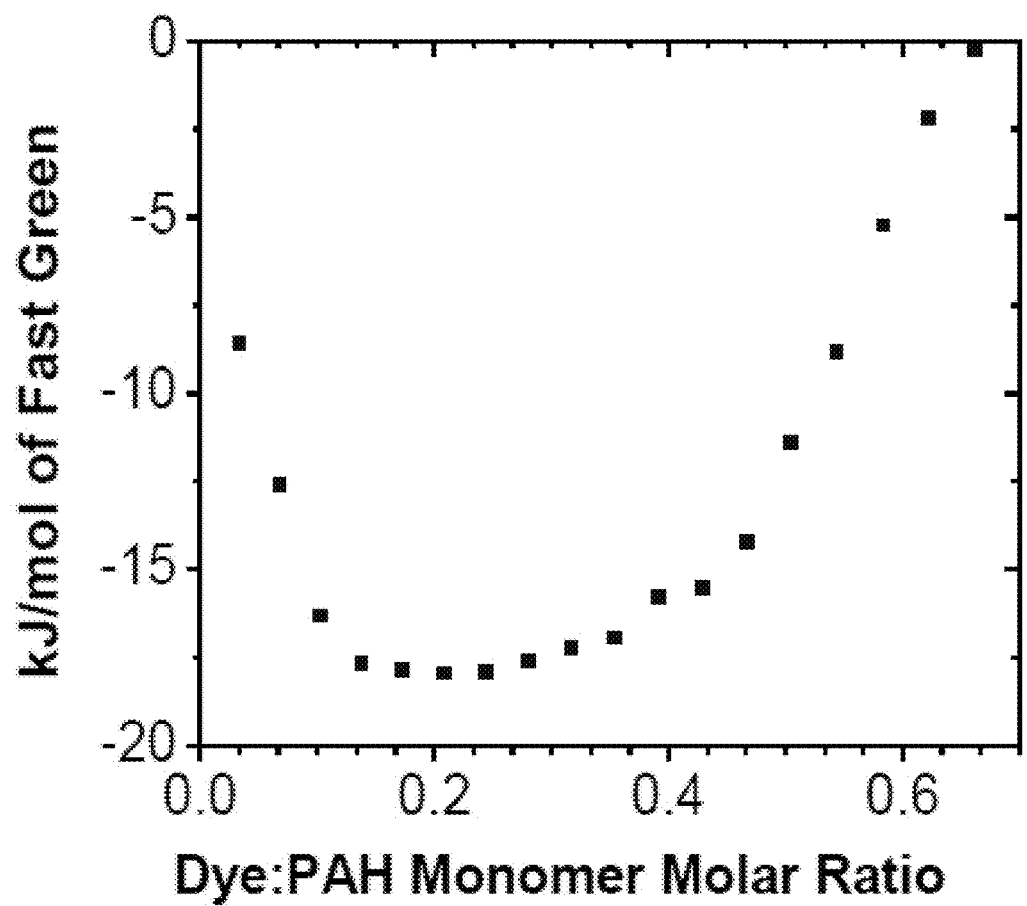
FIGS. 26A-26D: ITC data for Fast Green titrated into the PAH/PPi (FIG. 26A) and PAH/TPP (FIG. 26B) dispersions, and Rhodamine B titrated into the PAH/PPi (FIG. 26C) and PAH/TPP (FIG. 26D) dispersions.
Figure 26B:
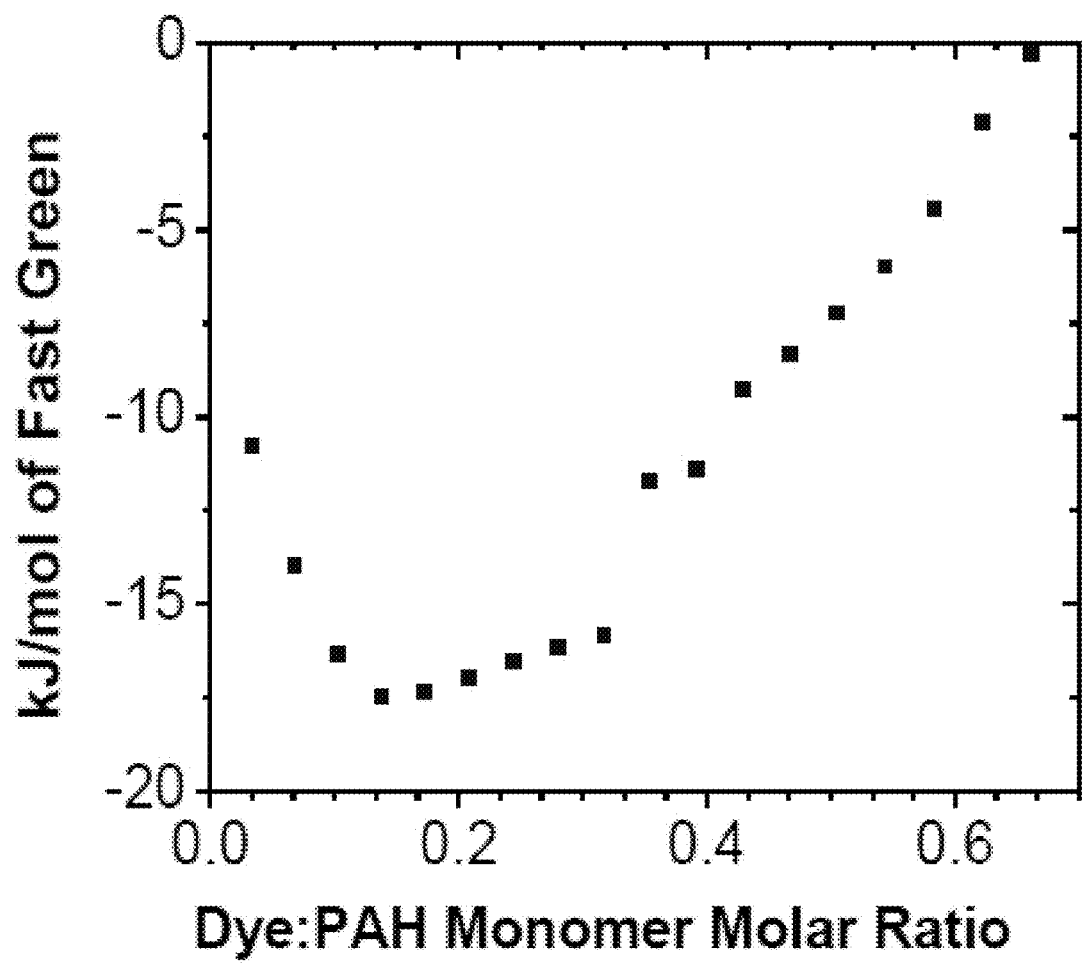
Figure 26C:
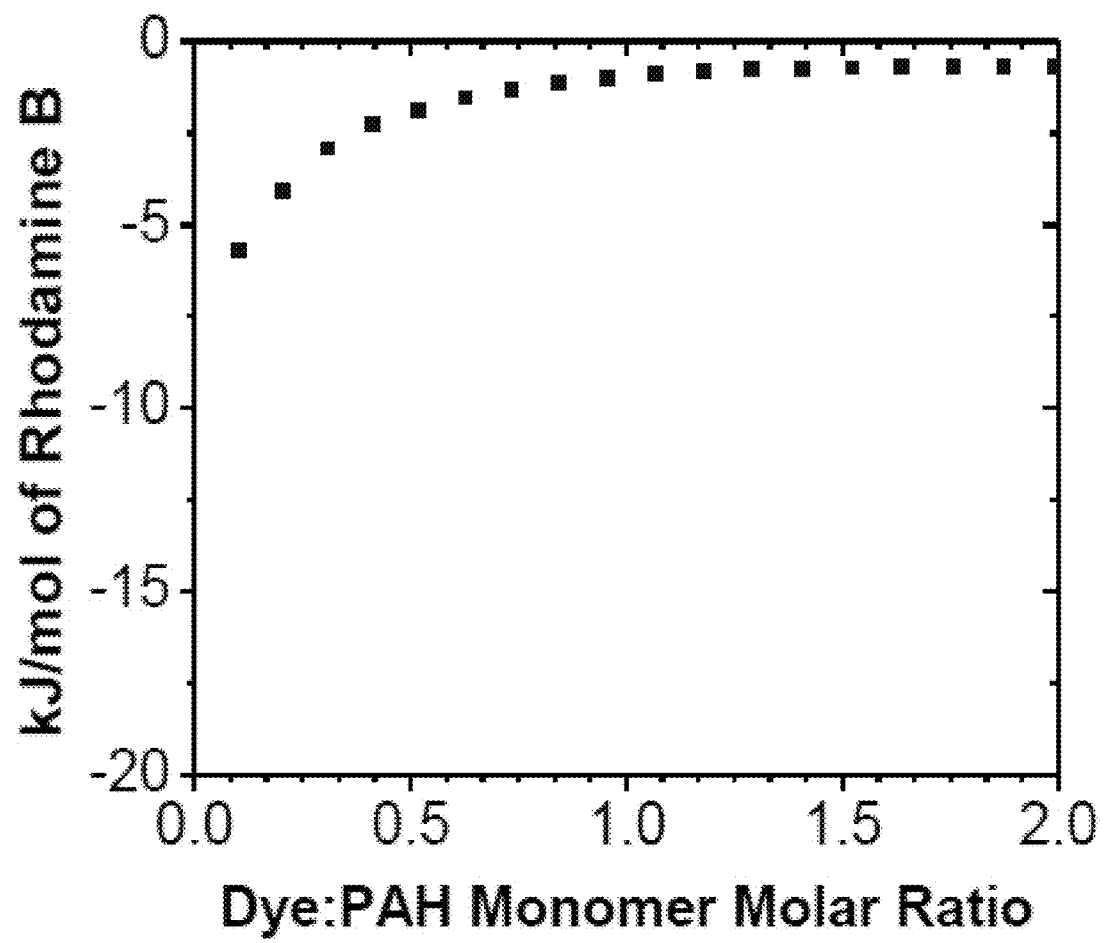
Figure 26D:
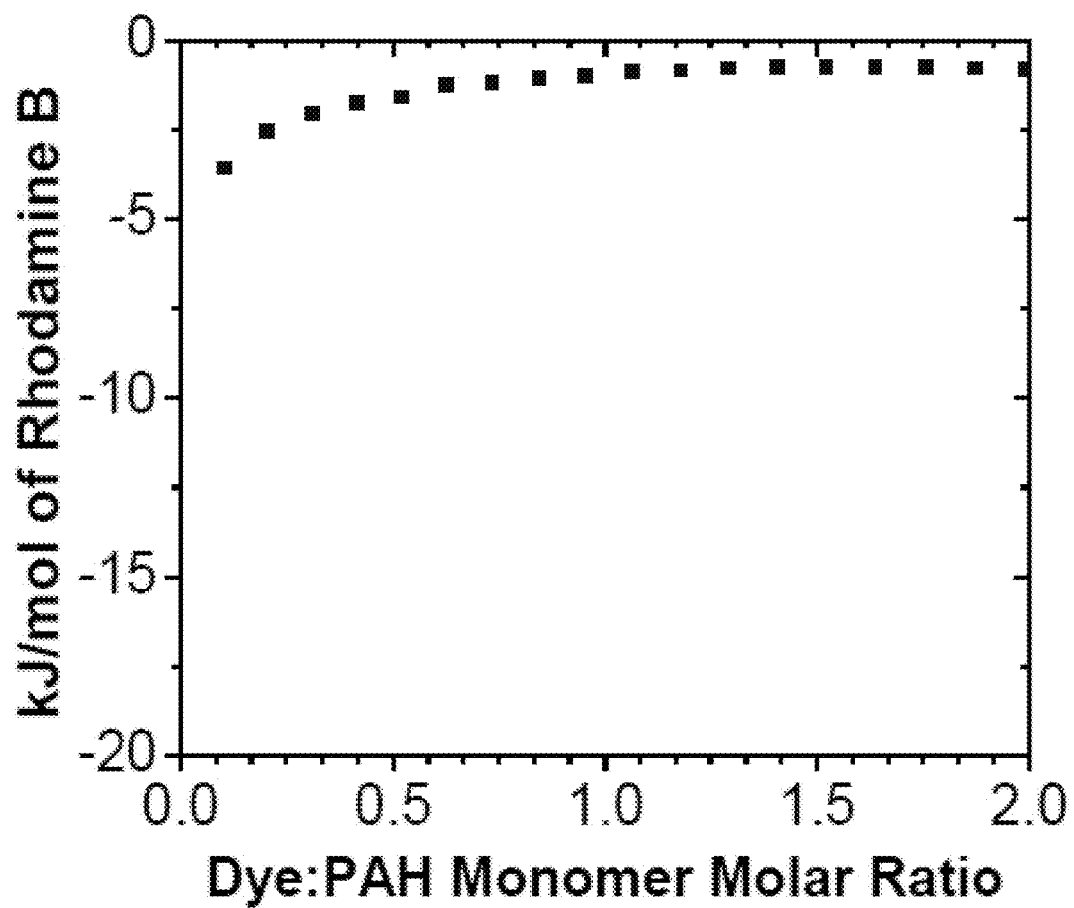

Similarly, to further demonstrate the stability of these adhesive coacervates, the dynamic rheology of the PAH/PPi and PAH/TPP complexes was probed before and after being stored in 1×PBS (i.e., at physiological pH and ionic strength) for 2 weeks. As mentioned above, increasing the ionic strength causes a reduction in the network stiffness and relaxation time. Testing the rheology of the adhesives after 2 weeks of storage in PBS revealed only minor changes in the dynamic rheology of these complexes, with a reduction in the G'-value only occurring at low $\omega$ (indicating a reduction in relaxation time) and the $G_\infty'$-values of these complexes remaining roughly constant (see FIGS. 25A-25B). This means that these adhesive networks retain their high crosslink density even at elevated ionic strengths similar to those seen in the human body. Notably, the rheology of the adhesives after 2 weeks of storage in PBS was very similar to that measured after 3 days of storage. This indicates that, after an immediate, ionic strength-induced reduction in relaxation time, the rheology of the adhesive gels remained fairly stable.

The cationic nature of the PAH and anionic nature of the PPi and TPP presents a situation in which a binding interaction could exist between the charged payload molecules and the ionically crosslinked network of the adhesive. Fast Green FCF and Rhodamine B are anionic and cationic, respectively. ITC was used to probe the binding of these dye molecules to the ionically crosslinked networks. In ITC the heat required to maintain a sample cell (which contains a binding substrate solution) at a constant temperature upon the addition of a binding ligand solution is measured, with endothermic or exothermic peaks in the ITC raw data indicating binding. The Fast Green FCF or Rhodamine B solutions were titrated into a PAH/PPi or PAH/TPP dispersion (prepared at a near stoichiometric PAH:crosslinker charge ratio). The thermograms obtained are shown in FIGS. 26A-26D, and indicate the binding enthalpy per mole of dye injected as a function of the dye:PAH molar ratio inside the sample cell. The plots obtained from the Fast Green FCF titrations are characteristic of a system with strong cooperative binding, with the exothermic binding signals (and consequently the binding strength) increasing with the dye:PAH molar ratio up to a ratio near 0.2:1. However, the plots from the Rhodamine B titrations exhibited much weaker exothermic signals, which continuously decreased as the dye:PAH molar ratio increased, meaning that Rhodamine B binds only very weakly and non-cooperatively with the network The preparation of the dye loaded PAH/PPi and PAH/TPP coacervates was simple. The PAH was mixed with one of the multivalent anions using PAH and multivalent anion solutions containing either Fast Green FCF or Rhodamine B. This caused dye molecules to become entrapped in the PAH/PPi and PAH/TPP networks during crosslinking. The loading capacities (LCs) and loading efficiencies (LEs) were dependent on the dye type and the initial dye concentration in the parent PAH, PPi, and TPP solutions (see Table 1).

TABLE 1

Loading efficiencies and capacities at different initial dye concentrations.

| | PAH/PPi | | PAH/TPP | |
|---|---|---|---|---|
| | Loading Efficiency (%) | Loading Capacity (mg/ml) | Loading Efficiency (%) | Loading Capacity (mg/ml) |
| Fast Green (0.5 mg/ml) | 56.48 ± 3.04 | 3.16 ± 0.17 | 64.01 ± 1.45 | 3.31 ± 0.07 |
| Fast Green (1 mg/ml) | 63.03 ± 1.37 | 7.04 ± 0.15 | 72.94 ± 3.09 | 7.54 ± 0.32 |
| Fast Green (4 mg/ml) | 68.54 ± 2.09 | 30.62 ± 0.93 | 74.74 ± 3.47 | 30.89 ± 1.43 |
| Rhodamine B (0.5 mg/ml) | 9.83 ± 2.79 | 0.55 ± 0.16 | 8.71 ± 2.10 | 0.45 ± 0.11 |
| Rhodamine B (1 mg/ml) | 6.38 ± 0.79 | 0.71 ± 0.09 | 6.27 ± 1.04 | 0.65 ± 0.11 |
| Rhodamine B (4 mg/ml) | 7.76 ± 2.77 | 3.46 ± 1.24 | 6.62 ± 1.41 | 2.74 ± 0.58 |

The LCs and LEs of Fast Green FCF were much higher than those of Rhodamine B. Without wishing to be bound by theory, it is believed this stemmed from the strong binding of Fast Green FCF to the PAH/PPi and PAH/TPP networks. Similarly, the relatively low LC and LE of Rhodamine B likely reflected its very weak binding to the PAH/PPi and PAH/TPP networks. Moreover, the Fast Green FCF LE-values increased with the dye concentration, while the Rhodamine B LE-values remained roughly constant. This increase in the Fast Green FCF LEs at higher dye concentrations was consistent with the cooperative binding between Fast Green FCF and the coacervates revealed by ITC (see FIGS. 26A-26B).

Figure 27:
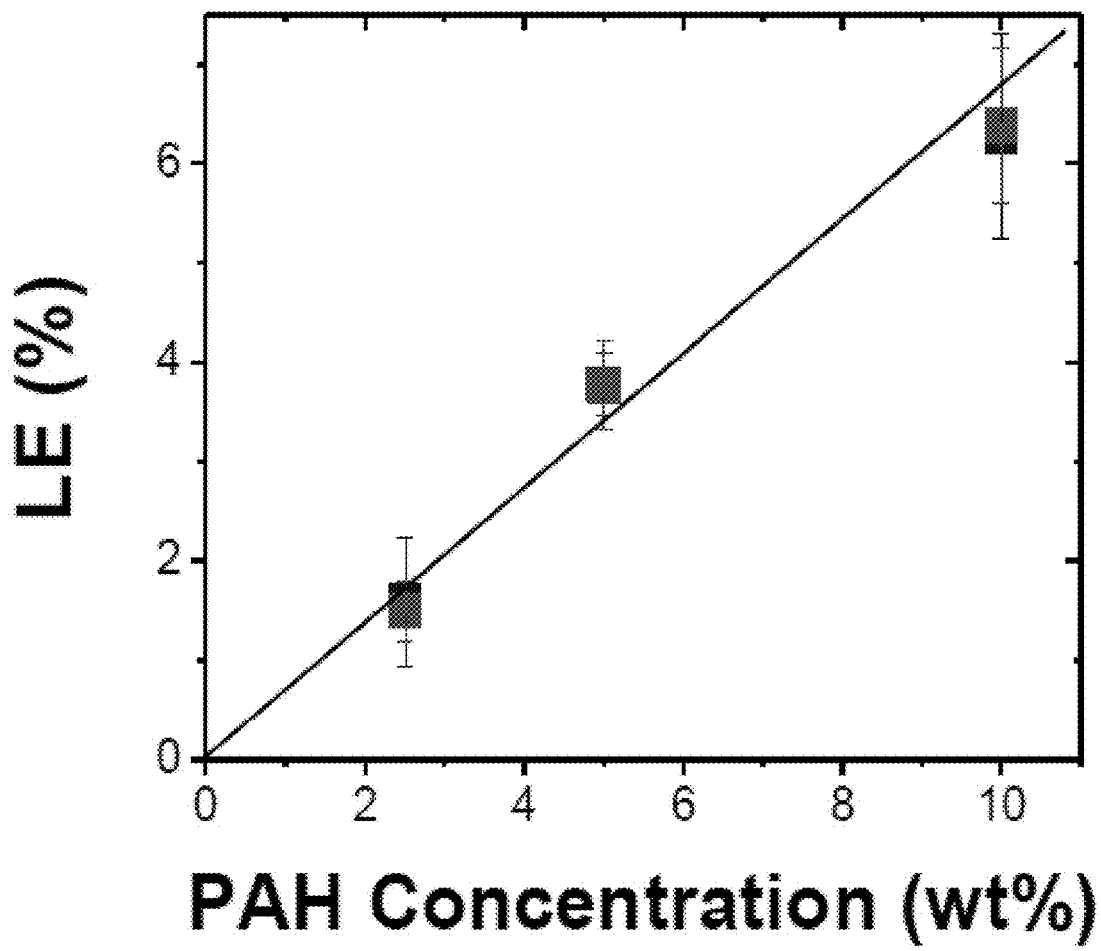
FIG. 27: The LEs of the Rhodamine B-loaded (■) PAH/PPi and (●) PAH/TPP adhesives plotted versus the PAH concentration. The line is a guide to the eye. The error bars are standard deviations (n=3).

The LEs for each dye type were also measured at a constant initial dye concentration (1 mg/ml) while varying the PAH concentration used during the encapsulation procedure (see Table 2). The LEs of the Rhodamine B-loaded adhesives increased linearly with PAH concentration (see FIG. 27). As the PAH concentration decreased, a lesser adhesive volume formed. Thus, less of the Rhodamine B could be enmeshed by the networks resulting in lower LEs. In contrast, the LEs of the Fast Green FCF-loaded adhesives remained fairly constant with the PAH concentration (Table 2). This was because a decrease in PAH concentration (as Fast Green FCF concentration remained constant) increased the dye:PAH molar ratio, which due to the cooperative nature of the Fast Green FCF/network binding, increased the fractional coverage of the PAH binding sites. Accordingly, the LE remained roughly constant even at a lower PAH concentration. Furthermore, in the case of the Fast Green FCF-loaded adhesives, the gel-like plugs at the bottoms of the microcentrifuge tubes did not form when 2.5 wt % PAH was used during the encapsulation procedure. Instead, the PAH/ionic crosslinker/dye complexes formed a flaky precipitate, which evenly coated the insides of the centrifuge tubes even after centrifugation. Without wishing to be bound by theory, it is believed this was because at this composition the Fast Green FCF:PAH ratio became so high that the Fast Green FCF bound to the PAH began to displace the PPi and TPP anions, which drastically changed the properties of the complexes.

TABLE 2

Loading efficiencies at different PAH concentrations used during complex formation.

| | PAH/PPi Loading Efficiency (%) | PAH/TPP Loading Efficiency (%) |
|---|---|---|
| Fast Green (2.5% PAH) | N/A | N/A |
| Fast Green (5% PAH) | 61.69 ± 1.13 | 72.40 ± 0.53 |
| Fast Green (10% PAH) | 63.03 ± 1.37 | 72.94 ± 3.09 |
| Rhodamine B (2.5% PAH) | 1.49 ± 0.30 | 1.59 ± 0.65 |
| Rhodamine B (5% PAH) | 3.76 ± 0.45 | 3.78 ± 0.32 |
| Rnodamme B (10% PAH) | 6.38 ± 0.79 | 6.27 ± 1.04 |

To characterize the controlled released properties of adhesive PAH/PPi and PAH/TPP coacervates, 1 ml of 1×PBS was added to microcentrifuge tubes containing approximately 0.2 ml of the dye-loaded adhesives, whereupon the samples were continuously mixed at 37° C. The released dye concentration in the PBS was determined using UV-Vis spectroscopy, with the PBS being replaced daily. This procedure was repeated until discernable UV-Vis peaks could no longer be obtained from the PBS samples in order to obtain release profiles.

Figure 28A:
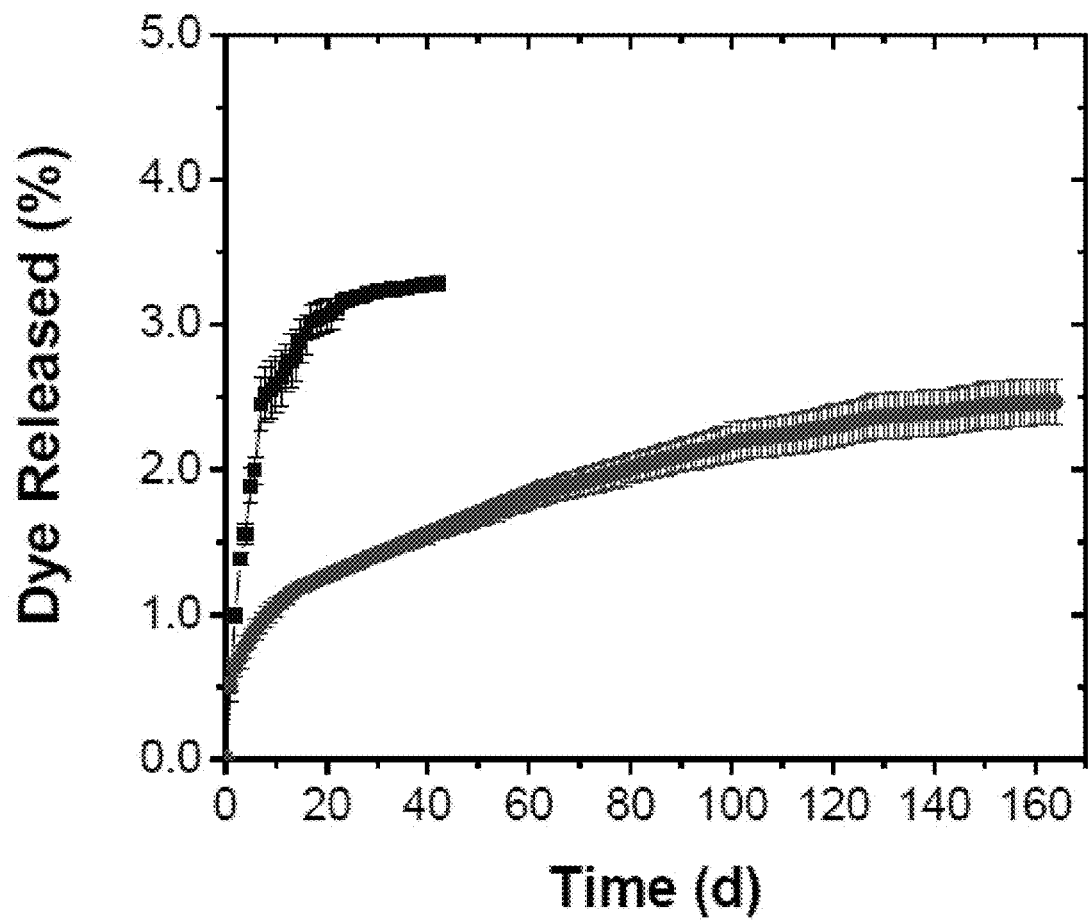
FIGS. 28A-28D: Release profiles obtained from PAH/PPi (FIGS. 28A, 28C) and PAH/TPP (FIGS. 28B, 28D) complexes loaded with (■) 1 mg/ml and (●) 4 mg/ml Fast Green dye plotted as (a, b) percent of dye released (FIGS. 28A-28B) and total mass of releases dye (FIGS. 28C-28D). The lines are guides to the eye. The error bars are standard deviations (n=3).
Figure 28B:
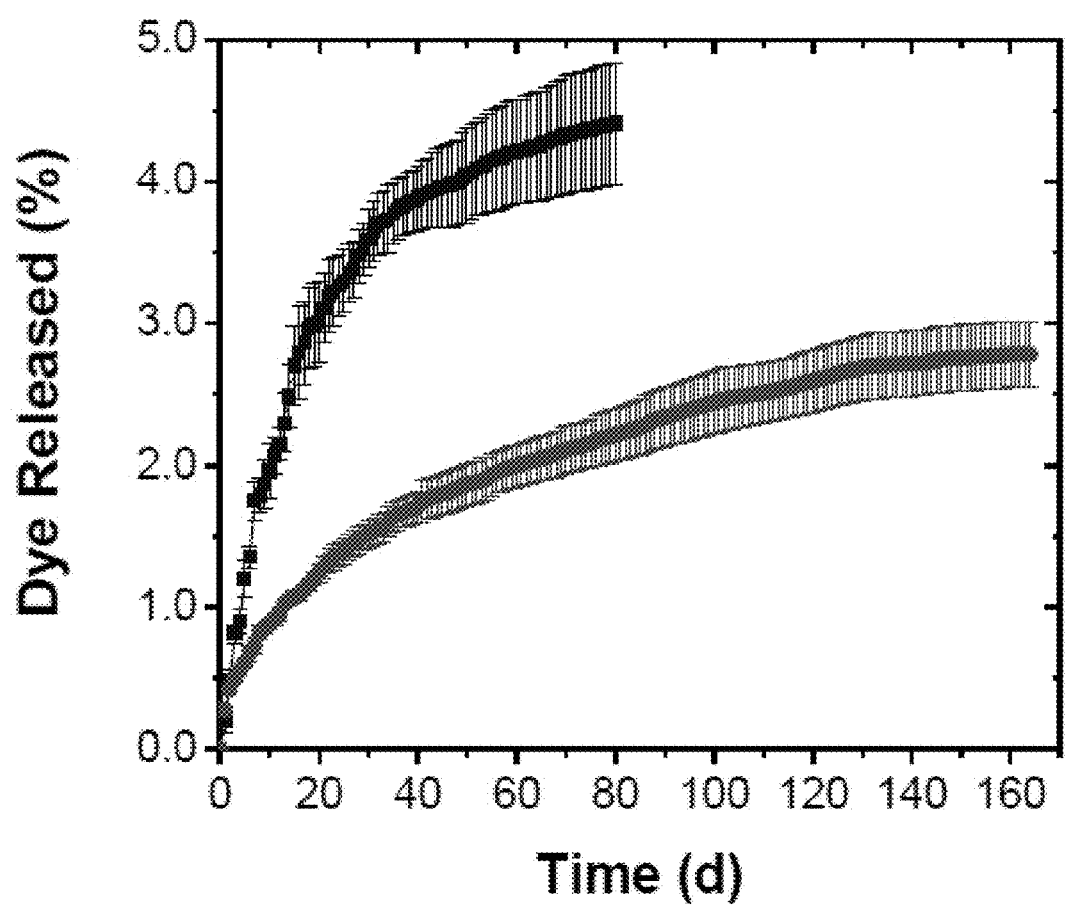
Figure 28C:
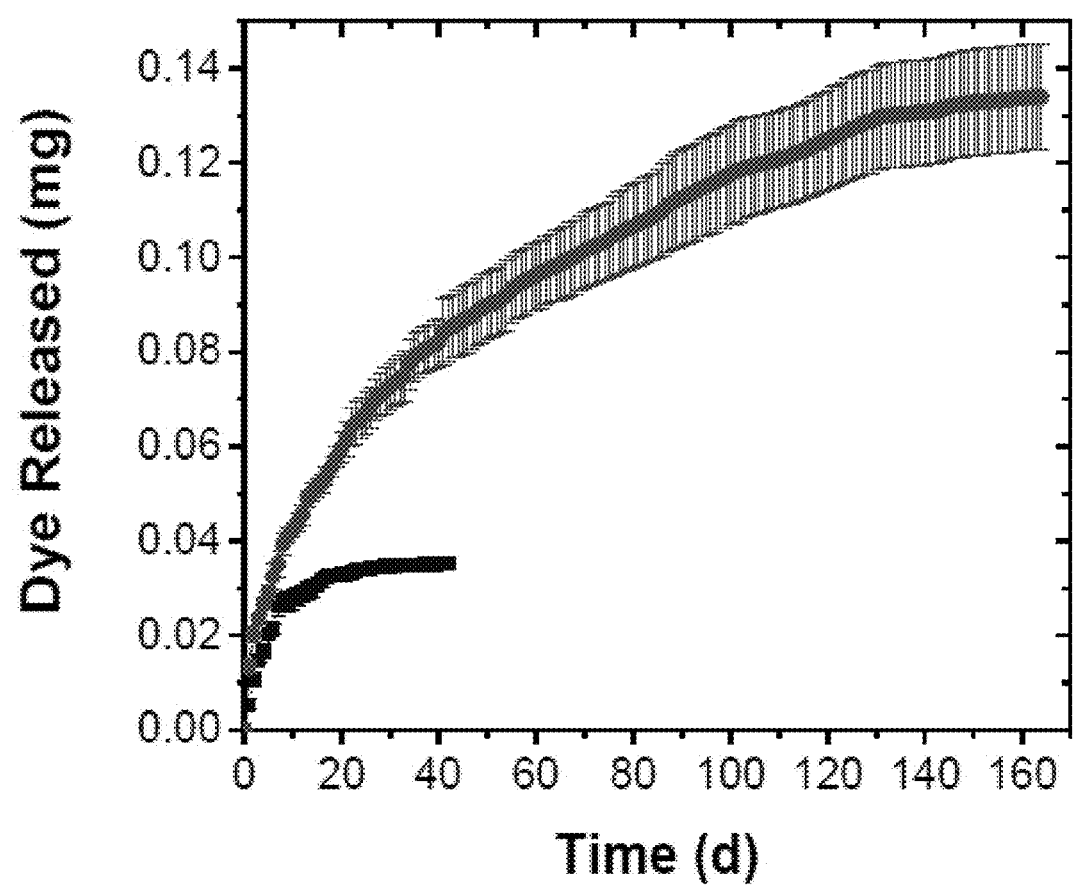
Figure 28D:
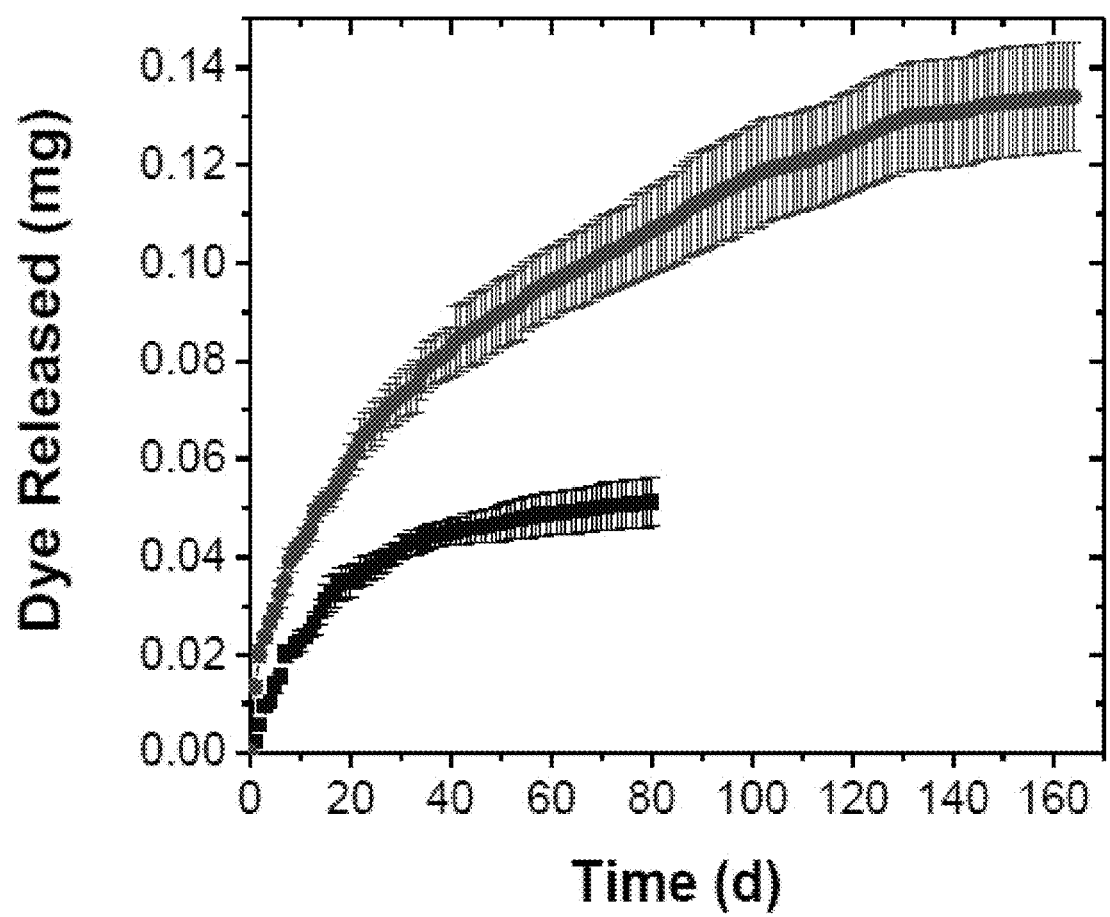
Figure 29A:
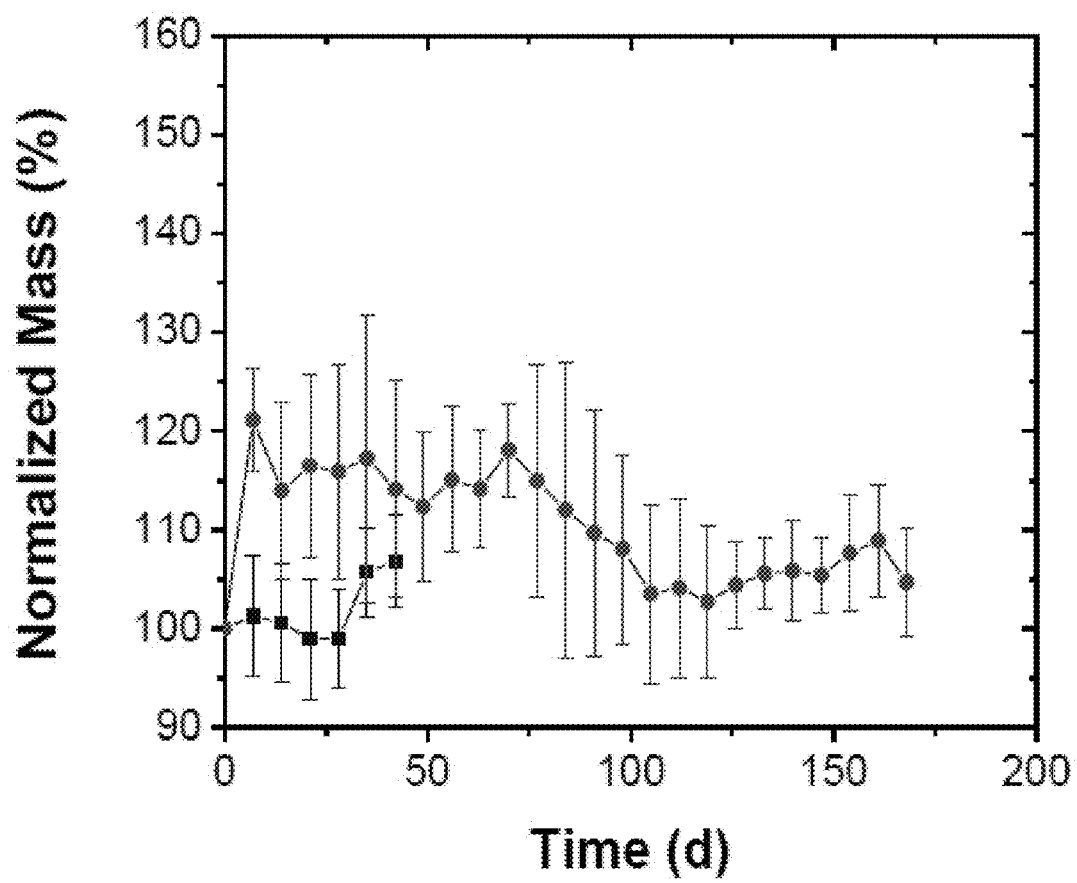
FIGS. 29A-29B: The mass of the Fast Green FCF-loaded PAH/PPi (FIG. 29A) and PAH/TPP (FIG. 29B) adhesives at initial Fast Green FCF concentrations of (■) 1 mg/ml and (●) 4 mg/ml, expressed as a percentage of their original mass and plotted as a function of time. The lines are guides to the eye. The error bars are standard deviations (n=3).
Figure 29B:
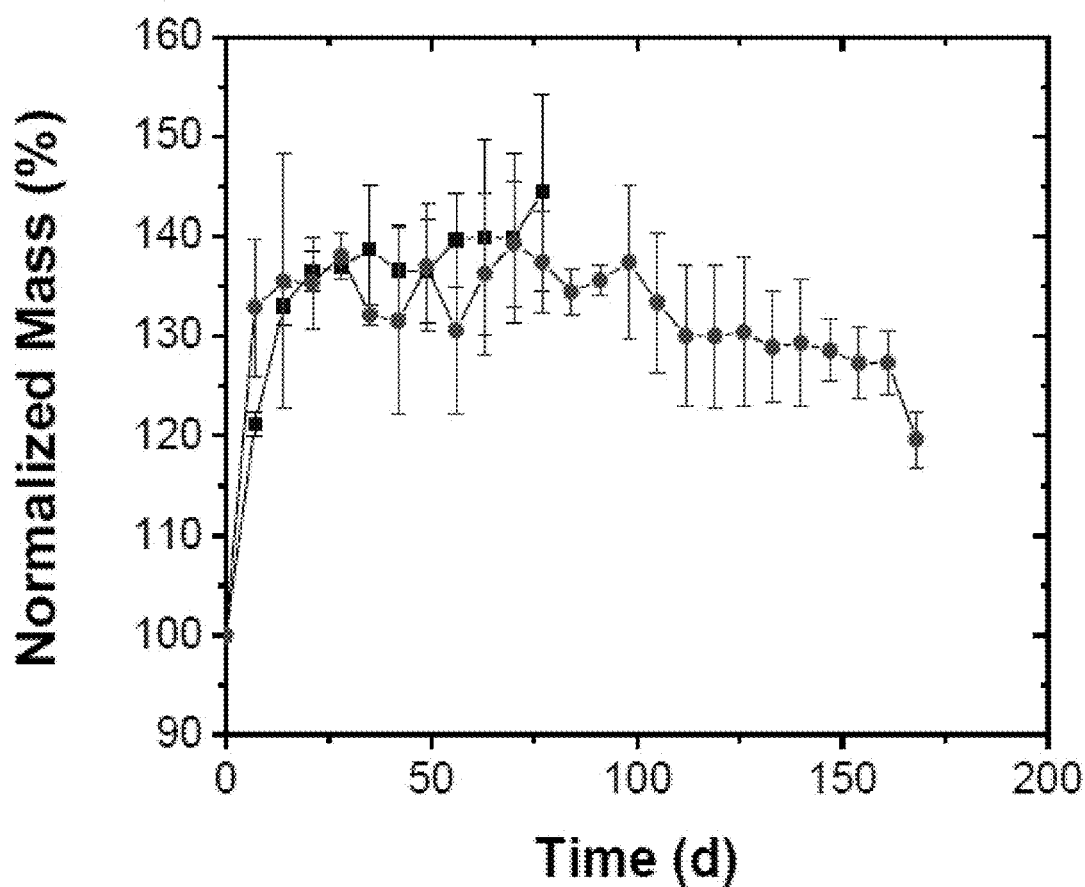

The complexes loaded with Fast Green FCF were capable of releasing a very small fraction (<5%) of their payload over a time span of up to 164 days, after which the release became too slow to obtain a discernable UV-Vis peak. The adhesives prepared at a Fast Green FCF concentration of 4.0 mg/ml released a lower percentage of dye and over longer timescales than those prepared at 1.0 mg/ml dye concentration (see FIGS. 28A-28B). As mentioned previously, Fast Green FCF binds cooperatively to the ionic network. Thus, when the initial Fast Green FCF concentration is increased from 1.0 mg/ml to 4.0 mg/ml, its stronger binding to the network prolongs its release. Yet, due to their higher LC-values (Table 1), the adhesives prepared at a Fast Green FCF concentration of 4.0 mg/ml released a higher total mass of dye than those prepared at the 1.0 mg/ml dye concentration (see FIGS. 28C-28D). This increase in the total rate of release indicates that the release rates can be easily tuned by varying the payload concentration used during the encapsulation procedure. Furthermore, the greater mass of dye being released allowed the dye release from the samples prepared at a Fast Green FCF concentration of 4.0 mg/ml to be tracked longer than those prepared at 1.0 mg/ml dye concentration. Because less dye was released from the adhesives prepared at a Fast Green FCF concentration of 1.0 mg/ml, it was difficult to obtain a discernable UV-Vis peak beyond 42 days for the PAH/PPi complexes and 80 days for the PAH/TPP complexes. Moreover, the mass of these dye-loaded coacervates was tracked during each release experiment (see FIGS. 29A-29B). After some initial swelling the mass of PAH/PPi and PAH/TPP coacervates decreased only very slightly over the entire release experiment (up to 164 days). This indicates that these Fast Green FCF-loaded coacervates degrade very slowly under physiological conditions.

Figure 30A:
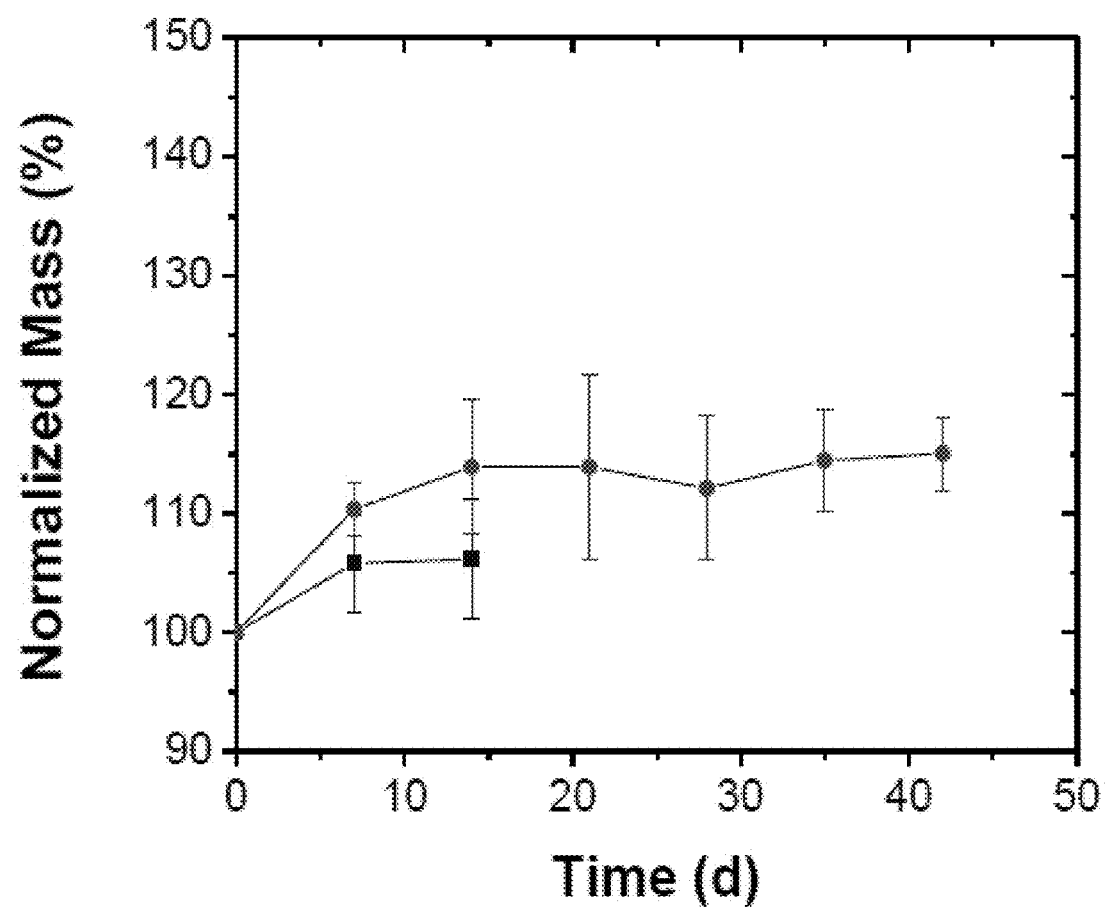
FIGS. 30A-30B: The mass of the Rhodamine B-loaded PAH/PPi (FIG. 30A) and PAH/TPP (FIG. 30B) adhesives at initial Rhodamine B concentrations of (■) 1 mg/ml and (●) 4 mg/ml, expressed as a percentage of their original mass and plotted as a function of time. The lines are guides to the eye. The error bars are standard deviations (n=3).
Figure 30B:
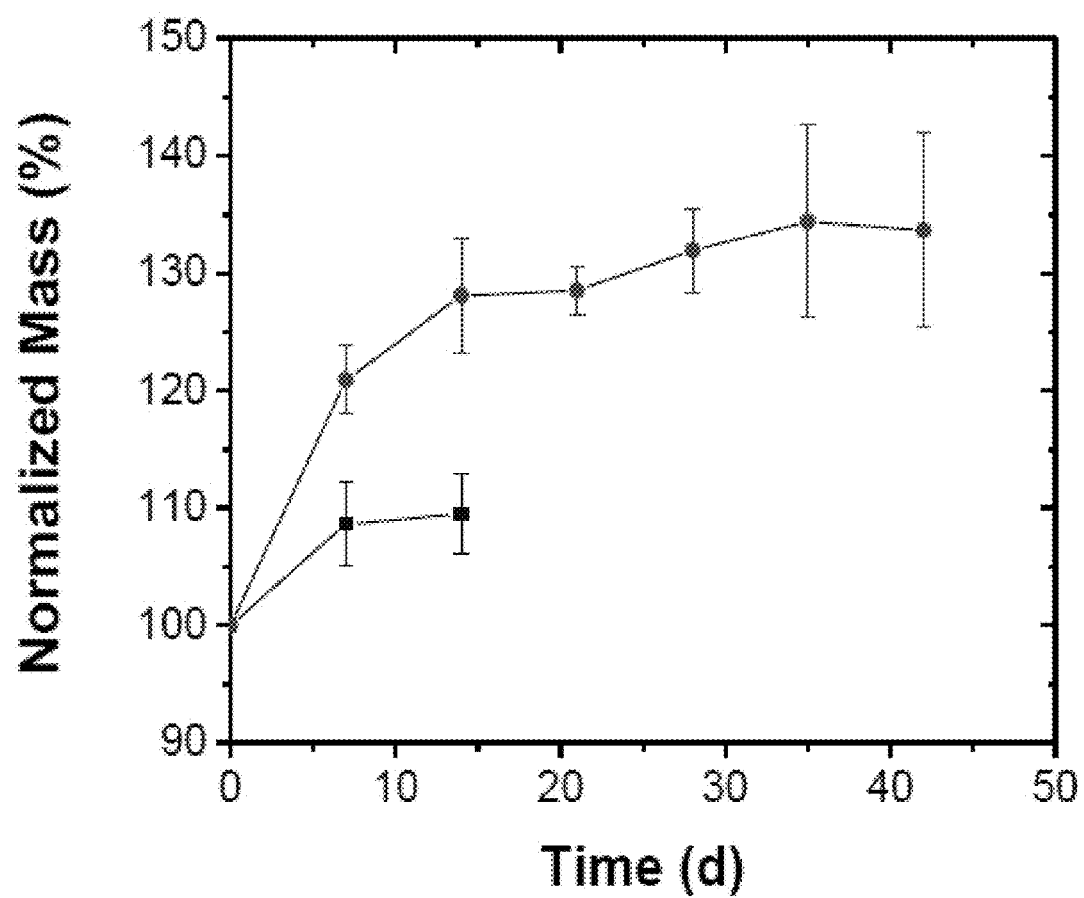
Figure 31A:
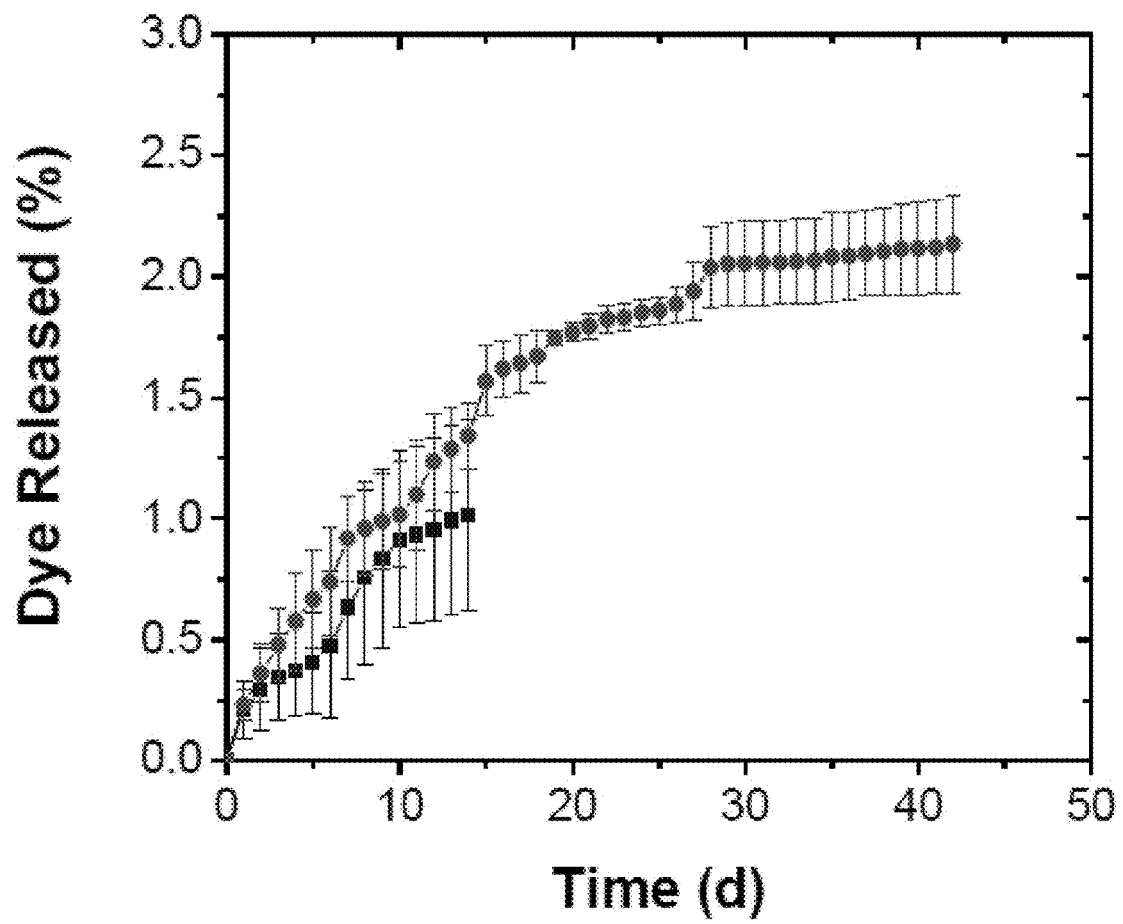
FIGS. 31A-31D: Release profiles obtained from PAH/PPi (FIGS. 31A, 31C) and PAH/TPP (FIGS. 31B, 31D) complexes loaded with (■) 1 mg/ml and (●) 4 mg/ml Rhodamine B dye plotted as percent of dye released (FIGS. 31A-31B) and total mass of releases dye (FIGS. 31C-31D). The lines are guides to the eye. The error bars are standard deviations (n=3).
Figure 31B:
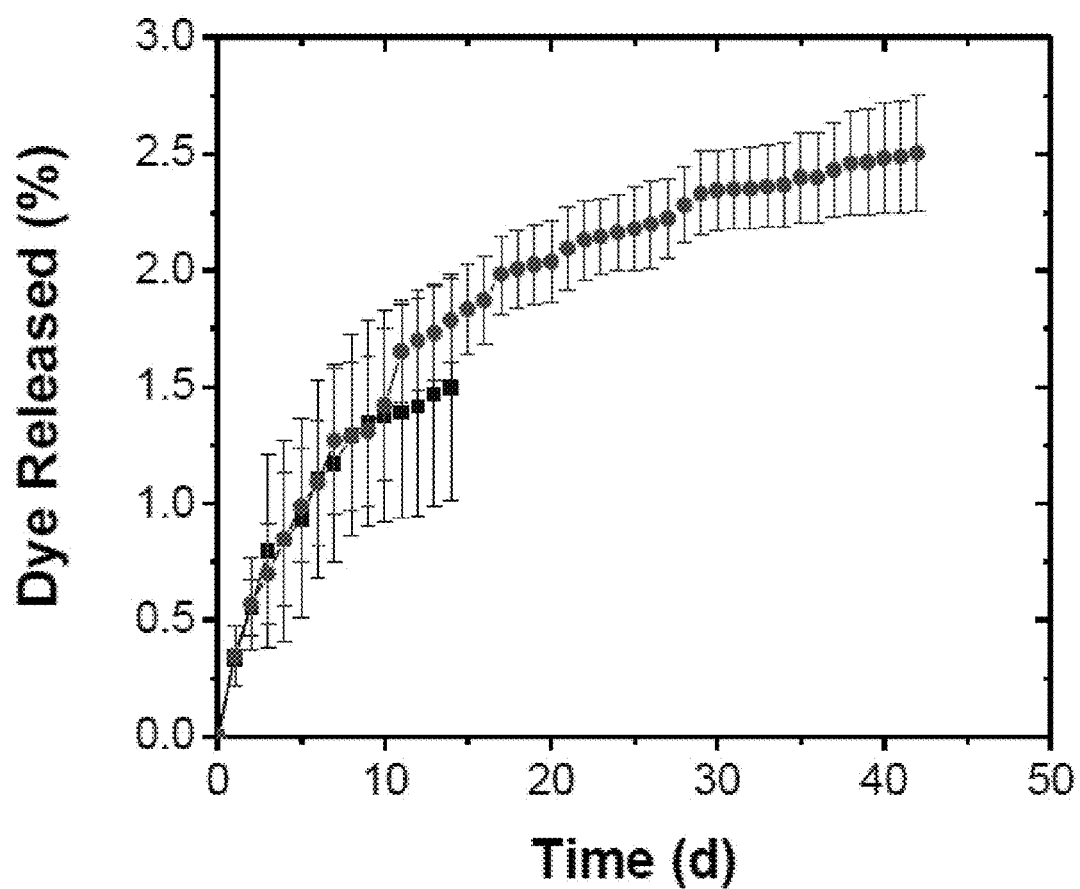
Figure 31C:
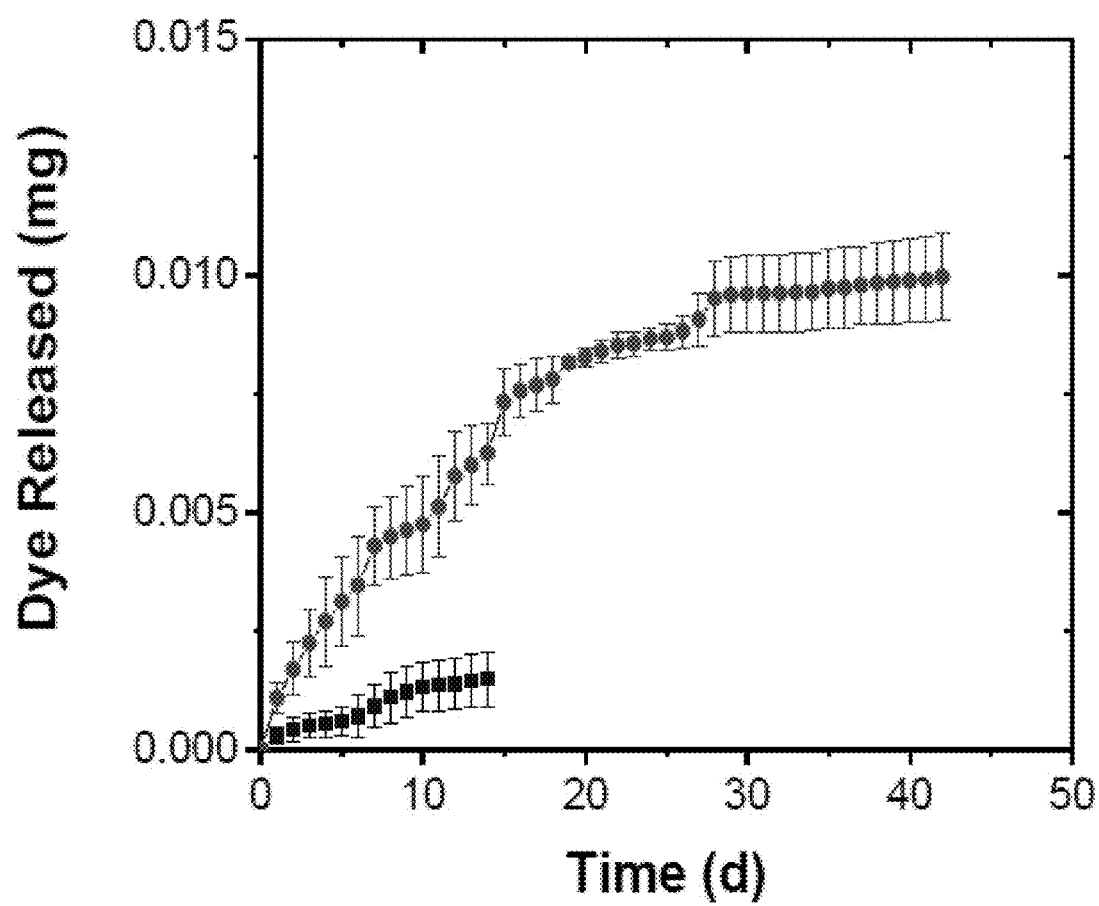
Figure 31D:
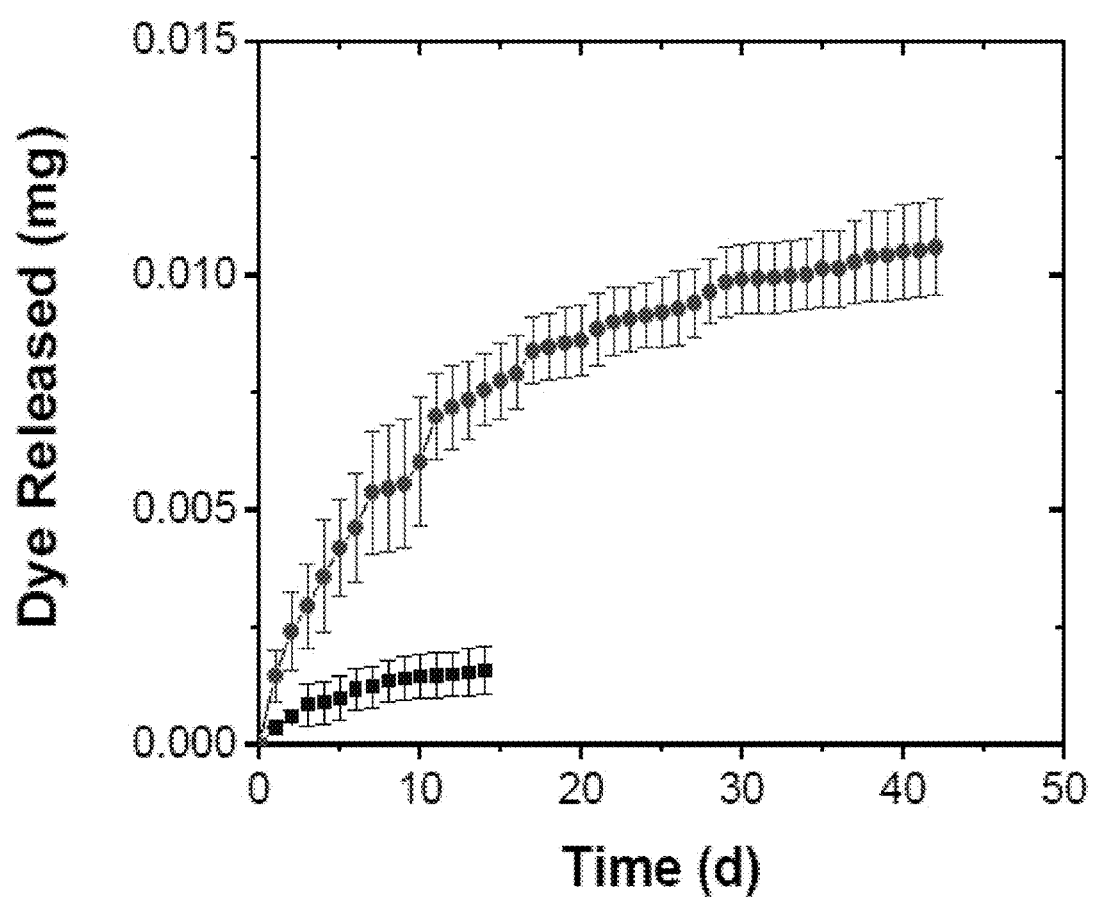
Figure 32A:
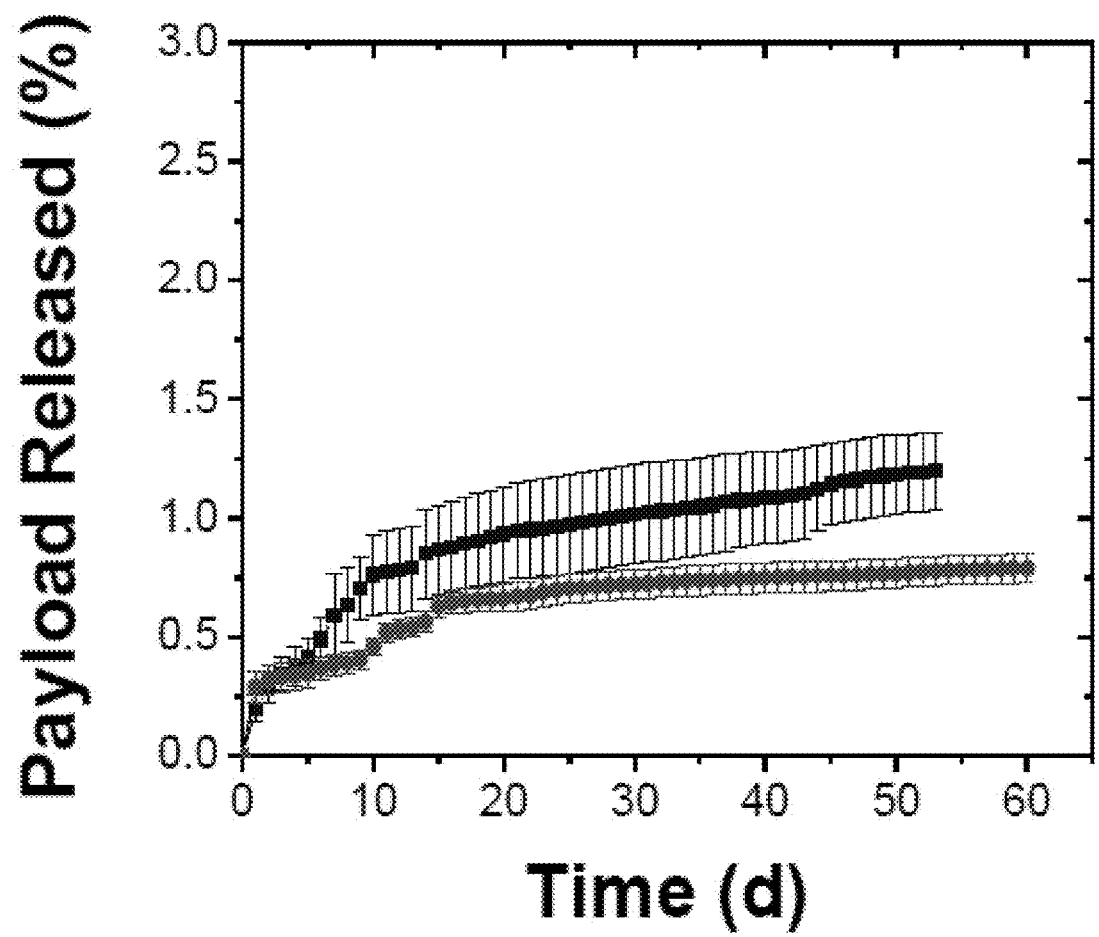
FIGS. 32A-32D: Release profiles obtained in tap water at room temperature from PAH/PPi (FIGS. 32A, 32C) and PAH/TPP (FIGS. 32B, 32D) complexes loaded with (■) 1 mg/ml and (●) 4 mg/ml Fast Green FCF dye plotted as percent of dye released (FIGS. 32A-32B) and total mass of released dye (FIGS. 32C-32D). The lines are guides to the eye. The error bars are standard deviations (n=3).
Figure 32B:
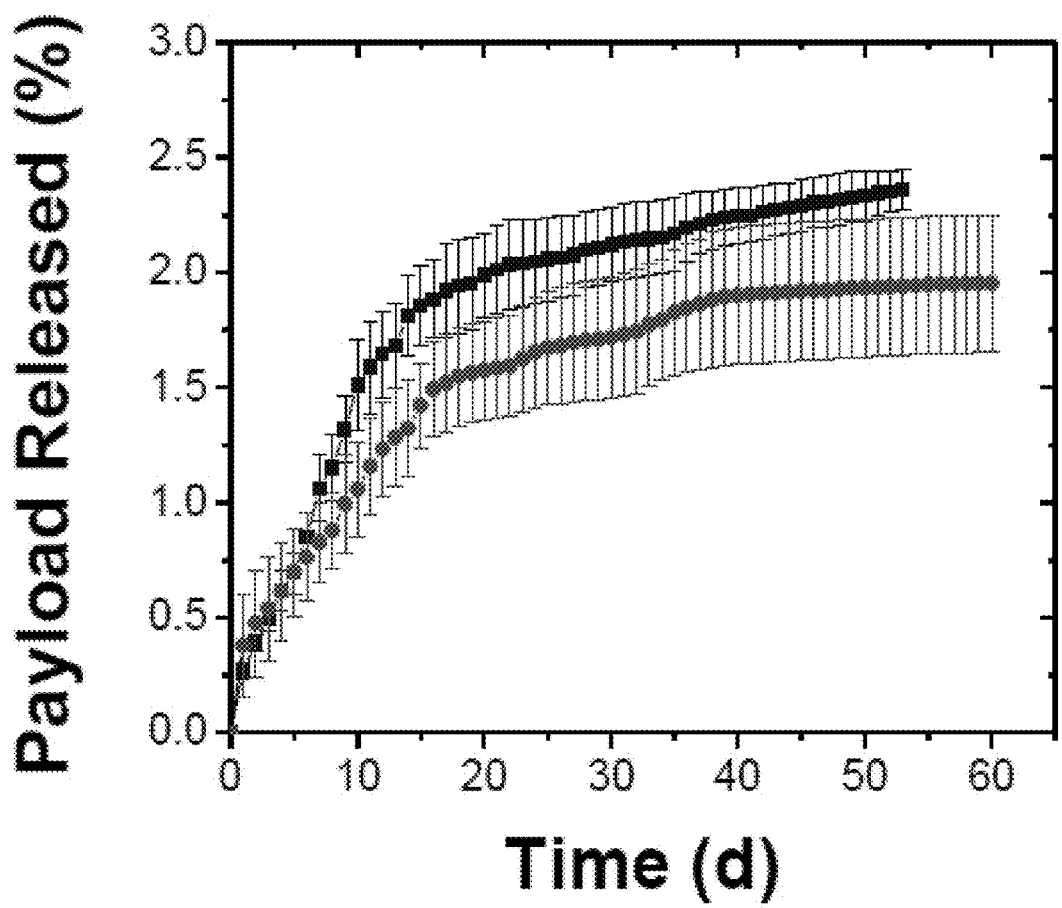
Figure 32C:
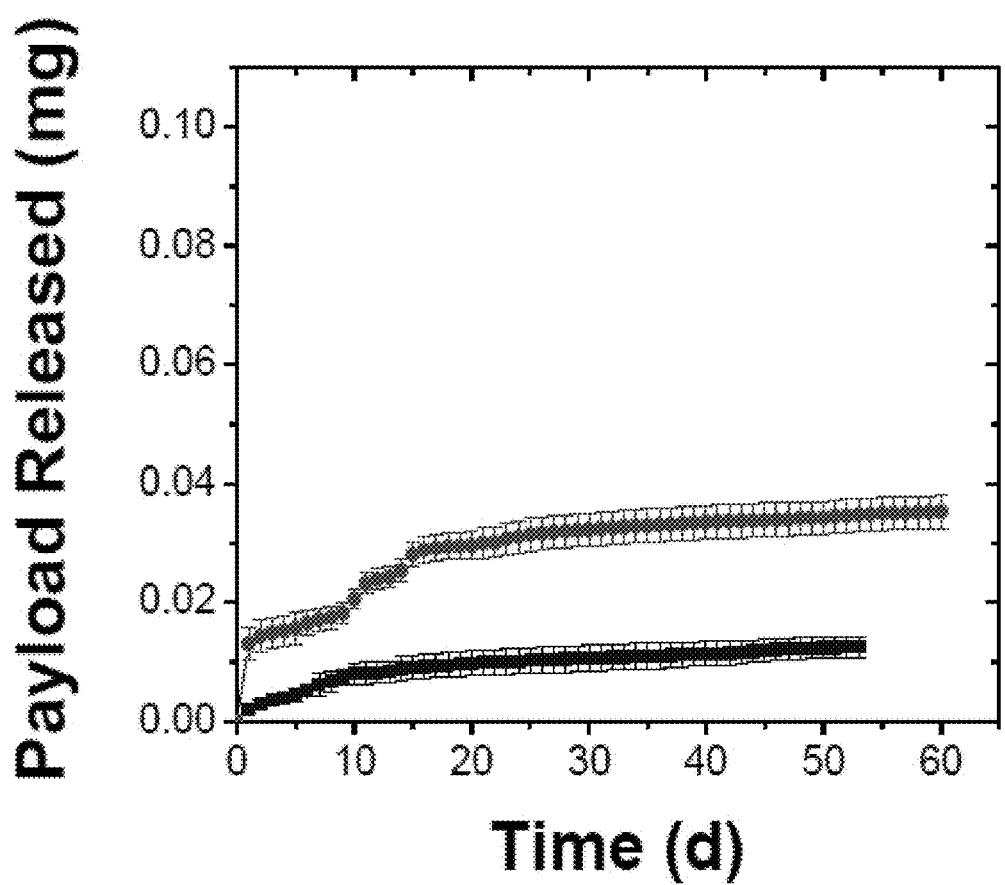
Figure 32D:
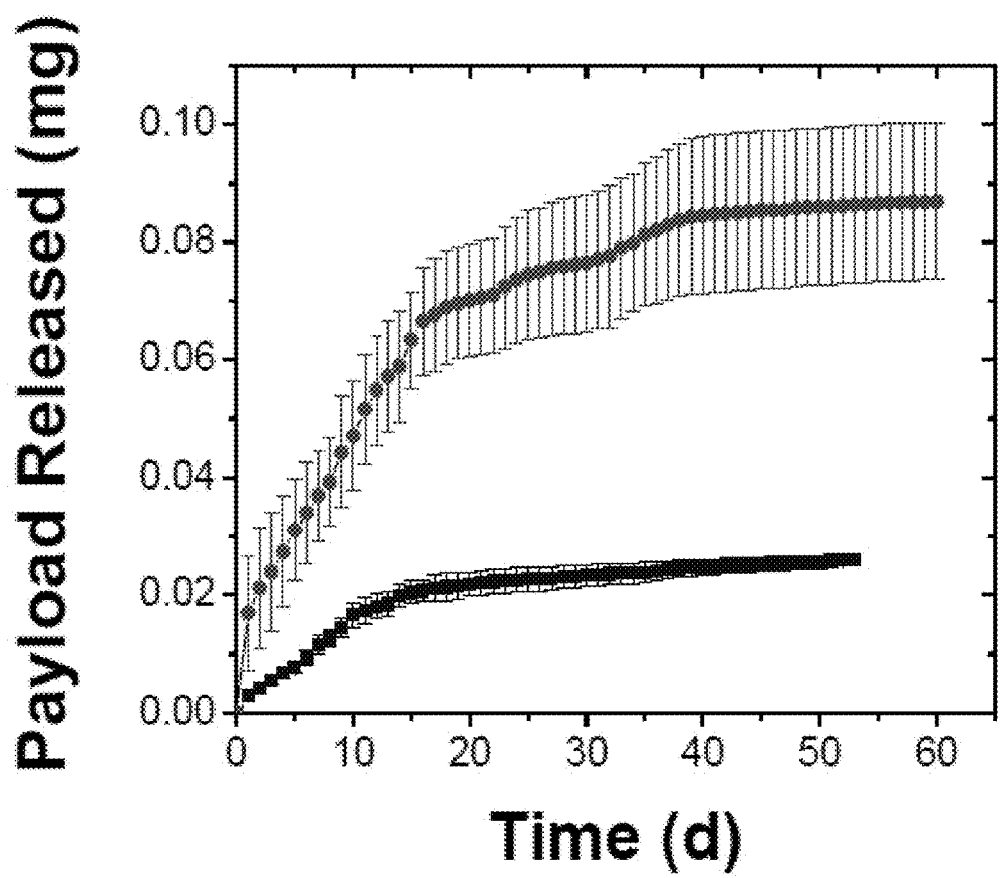
Figure 33A:
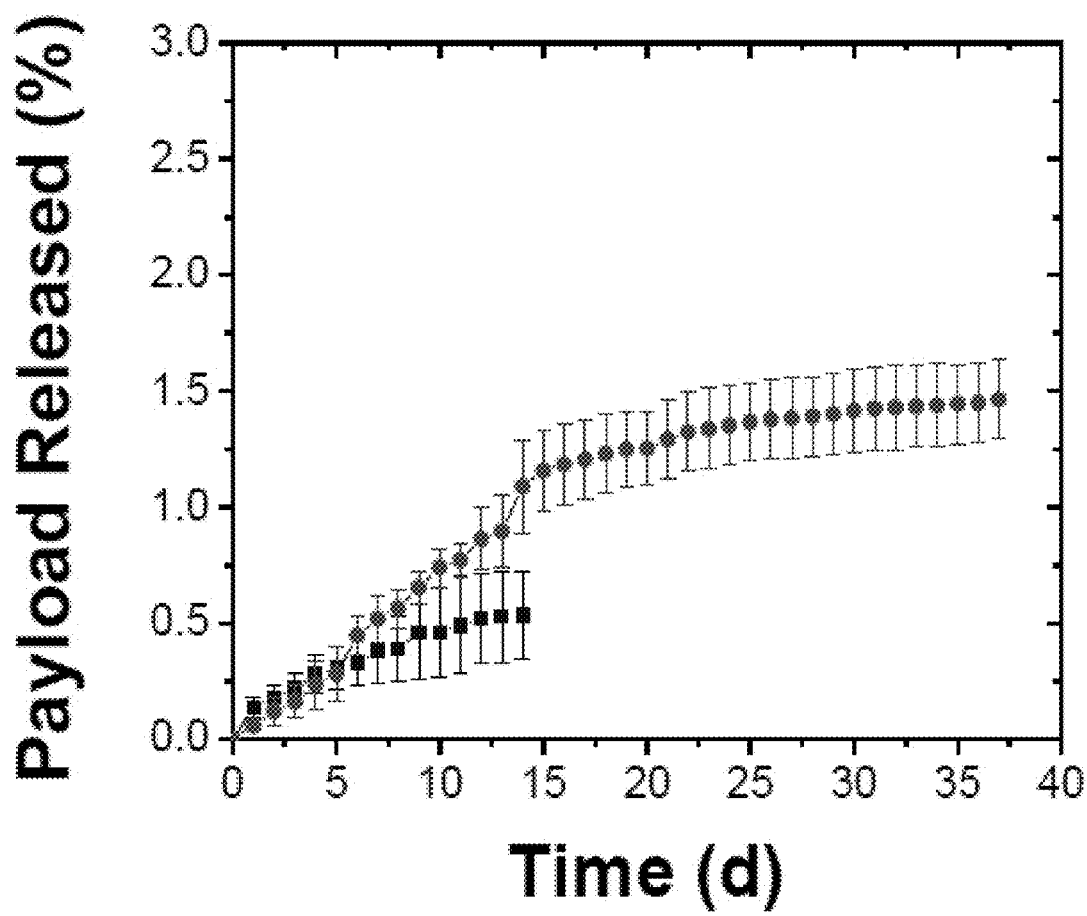
FIGS. 33A-33D: Release profiles obtained in tap water at room temperature from PAH/PPi (FIGS. 33A, 33C) and PAH/TPP complexes (FIGS. 33B, 33D) loaded with (■) 1 mg/ml and (●) 4 mg/ml Rhodamine B dye plotted as percent of dye released (FIGS. 33A-33B) and (c, d) total mass of released dye (FIGS. 33C-33D). The lines are guides to the eye. The error bars are standard deviations (n=3).
Figure 33B:
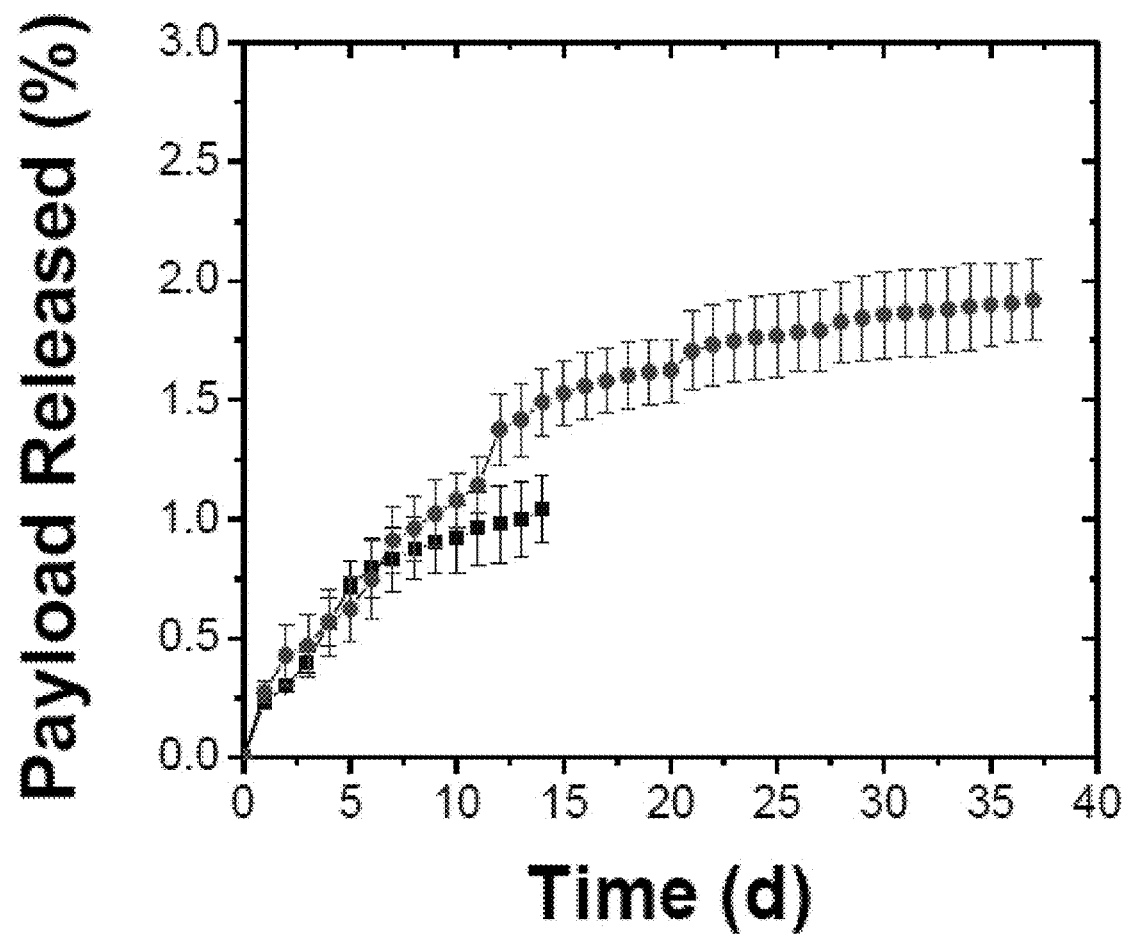
Figure 33C:
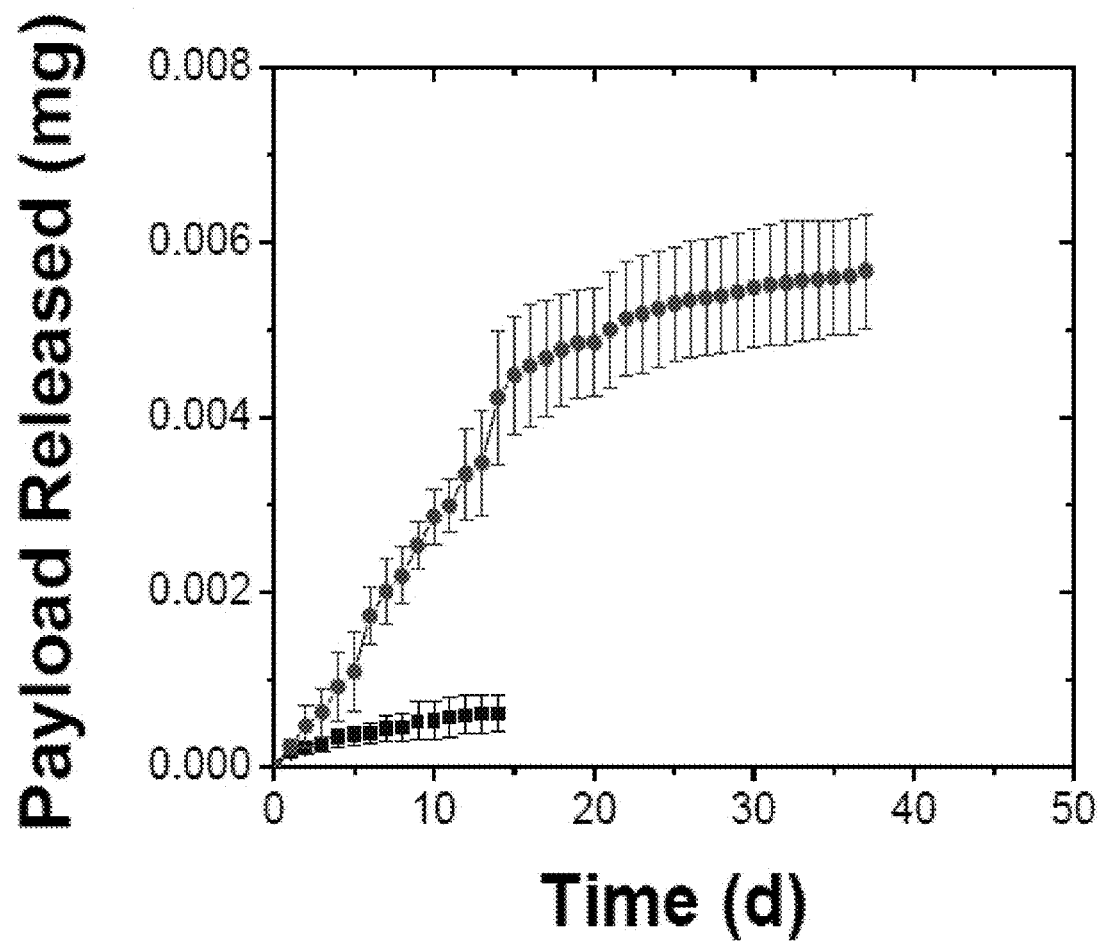
Figure 33D:
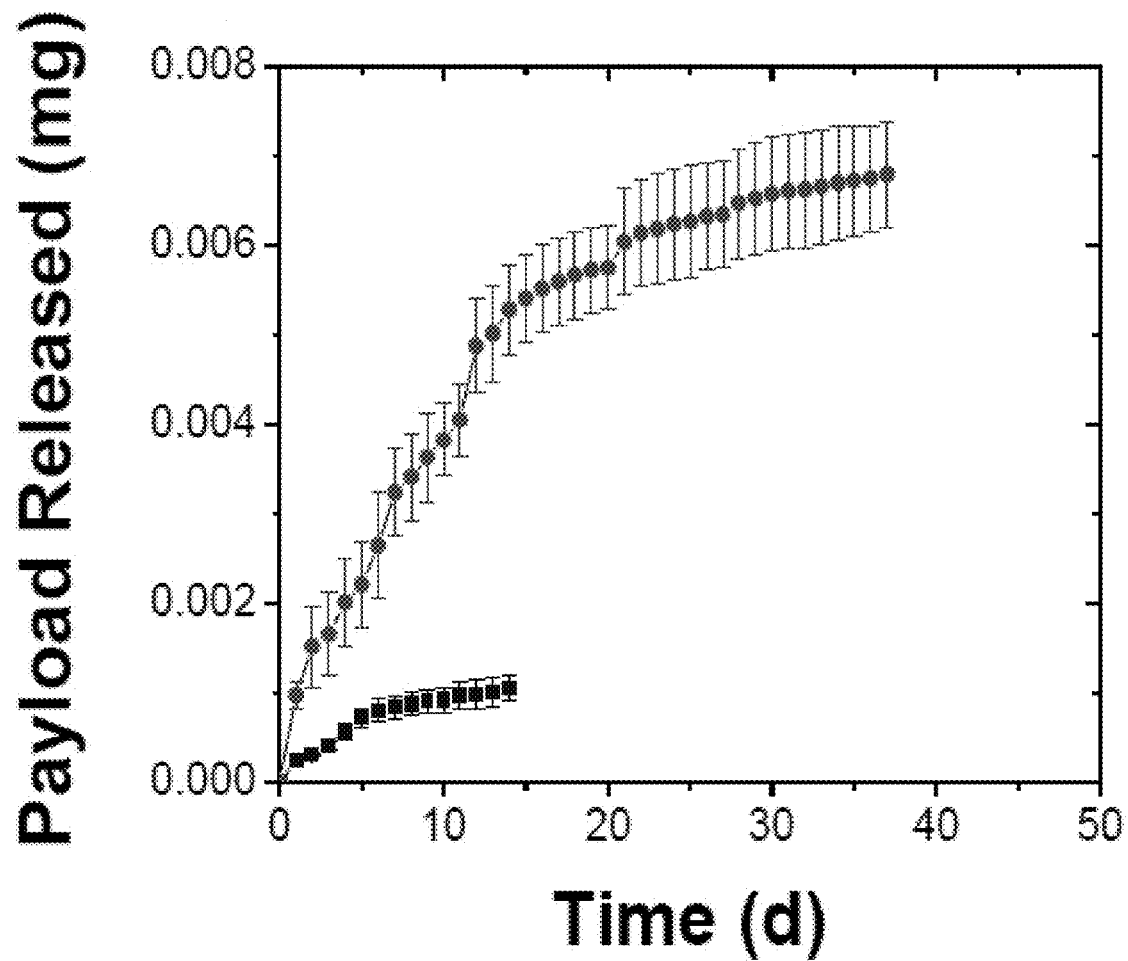

The stability of the Fast Green FCF-loaded PAH/PPi and PAH/TPP coacervates (the same coacervates used during the dye release experiments) was determined by tracking the mass of these coacervates during their release in 1×PBS at 37° C. (see FIGS. 29A-29B). Measurements were taken once a week throughout the entire release experiment. Noticeable swelling occurred within the first 1-2 weeks of release. After this initial swelling, the mass of PAH/PPi and PAH/TPP coacervates decreased only very slightly over the entire release experiment (up to 164 days), meaning that these Fast Green FCF-loaded coacervates degrade very slowly under physiological conditions. Similarly, the mass of the Rhodamine B-loaded PAH/PPi and PAH/TPP coacervates was also tracked during their release (see FIGS. 30A-30B). Again, after the initial swelling, the mass of the coacervates remained roughly constant over the entire release experiment (up to 42 days), indicating that these Rhodamine B-loaded coacervates are largely stable under physiological conditions.

The adhesives loaded with Rhodamine B were also capable of releasing a very small fraction of their payload over multiple week timescales (see FIGS. 31A-31D). Again, the time over which the experiments were performed were limited to the early portions of the release profiles, where a discernable UV-Vis peak could be obtained (even though further release still occurred). Because Rhodamine B had significantly lower LEs than Fast Green FCF (see Table 1), there was significantly less Rhodamine B loaded into the coacervates compared to the Fast Green FCF. Consequently, a lower total mass of Rhodamine B was released (see FIGS. 31A-31D), which made it difficult to obtain discernable UV-Vis peaks over long timescales. Furthermore, unlike the adhesives loaded with Fast Green FCF, the adhesives loaded with Rhodamine B dye released approximately the same percentage of dye over time regardless of the initial dye concentration (see FIGS. 31A-31B). This was because the binding of the Rhodamine B to the network was very weak. Therefore, the rate of release was likely largely determined by the crosslink density and the concentration gradient within the network. Under these conditions, the mass of dye released over time should scale linearly with the LC. This is why the coacervates loaded with Rhodamine B dye released approximately the same percentage of dye over time regardless of the initial dye concentration. Again, after tracking the mass of these dye-loaded coacervates (see FIGS. 30A-30B), it can be concluded that the Rhodamine B-loaded coacervates are quite stable under physiological conditions.

While the slow release of Fast Green FCF molecules may in part be attributed to their binding to the ionic networks, the slow release of non-binding Rhodamine B indicates the permeability of PAH/PPi and PAH/TPP networks as the reason for this slow release. Without wishing to be bound by theory, it is believed that this property stems from their high crosslink densities, and indicates that PAH/PPi and PAH/TPP complexes can be used for the multiple-month delivery of small molecules, even those small molecules that do not bind to the ionic network.

Furthermore, the long-term release of small molecules achieved with these complexes is not limited only to a PBS medium. Release experiments were also performed using tap water at room temperature as the release medium. These experiments yielded similar slow release rates. (See FIGS. 32-33.) A release study was run using the same procedure described above, however, the release medium was changed from 1×PBS to tap water at room temperature. The results for the Fast Green FCF and Rhodamine B loaded hydrogels are plotted in FIGS. 32A-32D and FIGS. 33A-33D, respectively.

Additionally, only a small percentage of the loaded dye was released even after multiple months (see FIGS. 28, 31). Qualitatively, the color of the PAH/PPi and PAH/TPP complexes (blue in the case of Fast Green FCF and pink in the case of Rhodamine B) faded much more near the surface than throughout the bulk of the gel-like plugs. This means that in the timescales studied in these experiments, diffusion of dye molecules was likely only occurring near the exposed surface of the adhesives.

Figure 34A:
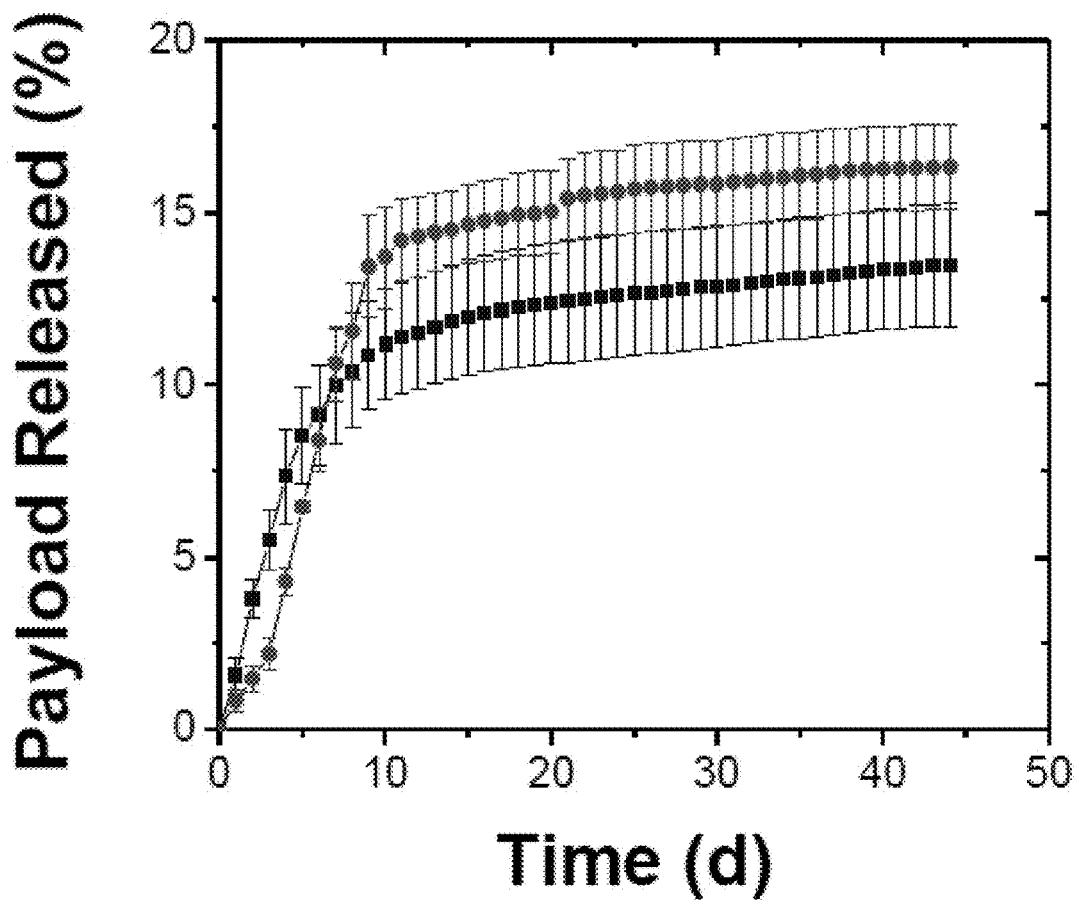
FIGS. 34A-34B: Release profiles obtained from 1-2 mm thick (■) PAH/PPi and (●) PAH/TPP gel-like plugs loaded with 4 mg/ml Fast Green FCF (FIG. 34A) or Rhodamine B (FIG. 34B) plotted as percent of dye released. The lines are guides to the eye. The error bars are standard deviations (n=3).
Figure 34B:
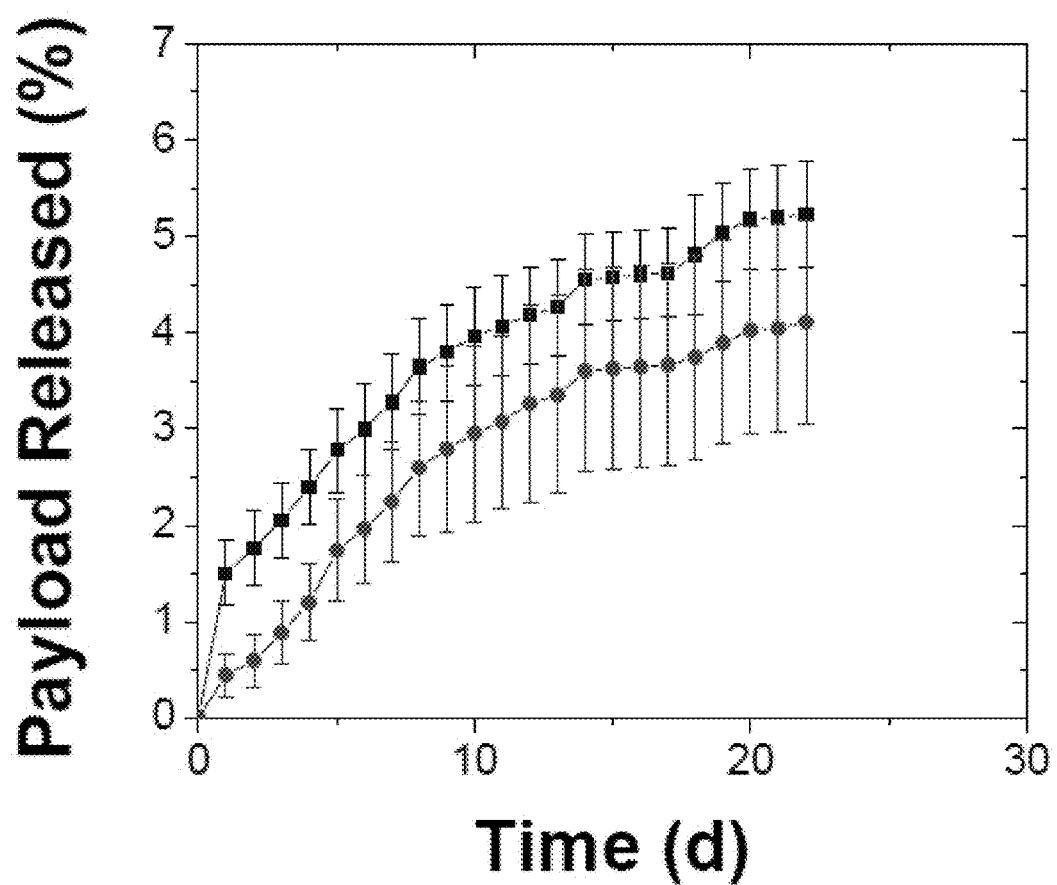

Release experiments were also run on dye loads adhesive samples with a thickness of only 1-2 mm (rather than 7-8 mm), and a much higher percent of the loaded dye was released (up to 15%). To determine the effect of PAH/PPi and PAH/TPP complex thickness on their release profiles, the coacervates were prepared using the procedure outlined above; however, only 0.047 ml of a 7.5 wt % PPi or 0.040 ml of a 7.5 wt % TPP were added to 0.038 ml of a 10.0 wt % PAH. All solutions contained 4.0 mg/ml of either Fast Green FCF or Rhodamine B. This procedure yielded 1-2 mm thick dye-loaded gel-like plugs at the bottoms of the microcentrifuge tubes. The release profiles were then obtained using the procedure outlined above. (See FIGS. 34A-34B.) These thinner gel-like plugs released a much higher percentage of the dye (~5-15%) than the thicker plugs described above.

Because the release rates of the dyes from the network is at least partially determined by the crosslink density of the networks, increasing the pH of the parent solutions used to form the adhesive coacervates increases release rates. Therefore, altering the pH at which the complexes are formed can be utilized as a mechanism for triggering payload release.

Example II

Effect of pH on PAH/PPi and PAH/TPP Complex Formation

Figure 14A:
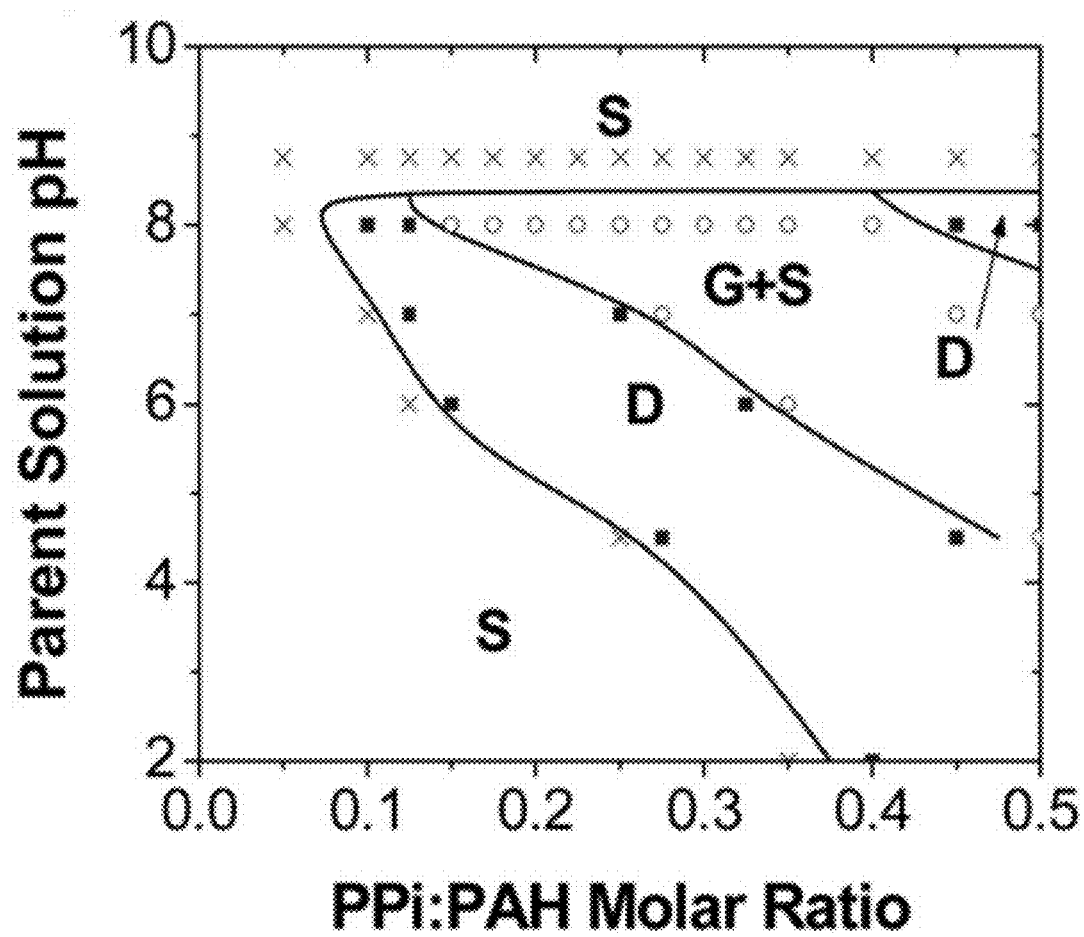
FIGS. 14A-14D: State diagrams for PAH/PPi (FIG. 14A) and PAH/TPP (FIG. 14B) mixtures plotted in terms of the parent PAH, PPi, and TPP solution pH, and state diagrams for PAH/PPi (FIG. 14C) and PAH/TPP (FIG. 14D) mixtures plotted in terms in terms of the pH after mixing. The lines indicate the boundaries between the (S) solution, (D) dispersion, and (G) gel-like aggregation states recorded after 1 month of equilibration.
Figure 14B:
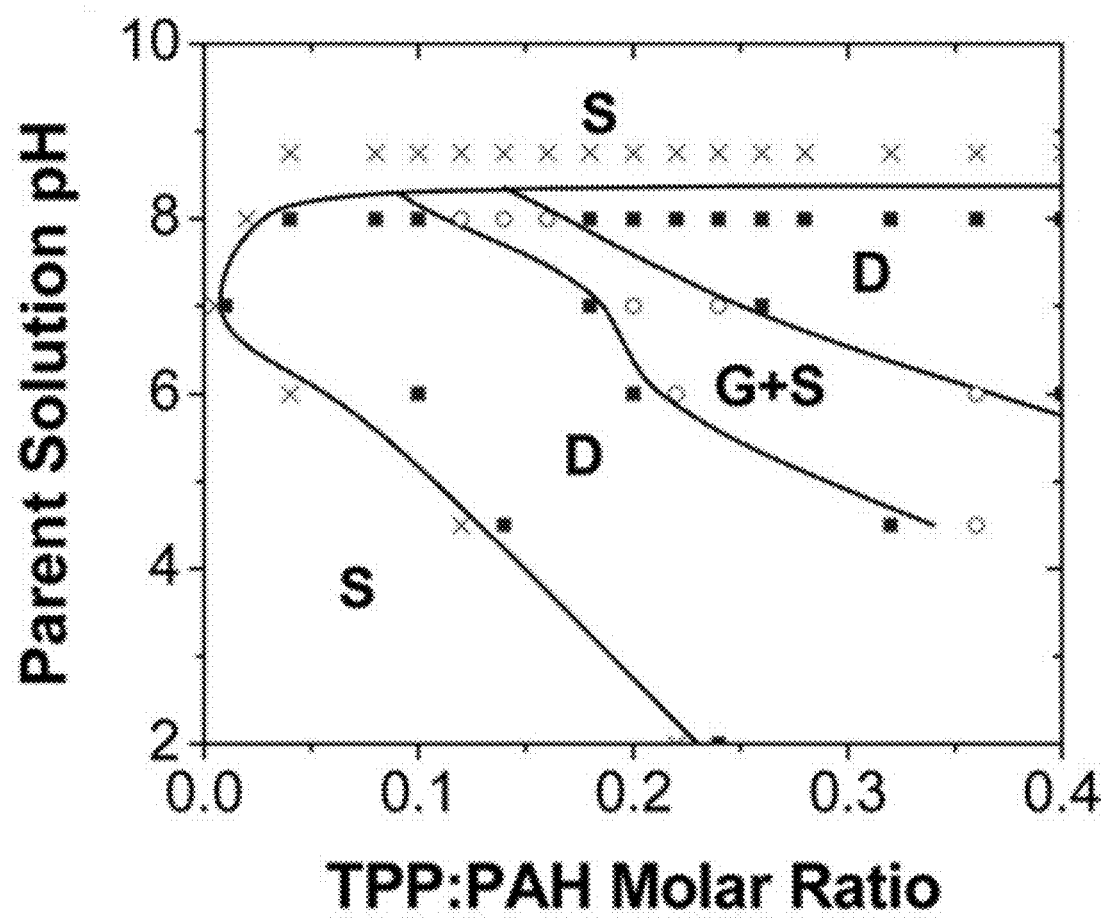

The compositions for adhesive formation were determined by mixing 0.04 wt % PAH solutions with different volumes of either 0.37 wt % PPi or 0.40 wt % on the ion:PAH monomer ratios where the dispersions coagulated to form the gel-like macroscopic adhesives ("G+S" regions in FIGS. 14A-14B). When the parent solutions were at pH-levels ranging between 2.0 and 8.0, colloidal dispersions formed at lower ion:PAH monomer ratios as the pH of their parent solutions were increased (see "S" to "D" region transitions in FIGS. 14A-14B). The parent solution pH had a similar impact on the ion:PAH monomer ratios where the dispersions coagulated to form the gel-like macroscopic adhesives ("G+S" regions in FIGS. 14A-14B). The same downward shift also occurred for the ion:PAH monomer ratios where the PPi and TPP-rich complexes ceased to undergo macroscopic phase separation (see "G+S" to "D" transitions at high ion:monomer ratios; FIGS. 14A-14B). As the pH of the parent solutions was raised to 8.8, however, the colloidal and macroscopic complexes ceased to form (FIGS. 14A-14B).

The pH dependence of each of these transitions reflected the acid-base equilibria of PAH, PPi, and TPP. The ionization of PPi and TPP increased at higher pH-levels, thereby reducing the ionic cross-linker requirements for the formation of colloidal and macroscopic complexes. Without wishing to be bound by theory, it is believed that this reduction in PPi and TPP requirement for each of the state transitions stemmed from: (1) the increased ionic cross-linker:PAH charge ratios and (2) a possible amplification in the polymer/crosslinker binding strength (where both occur due to an increase in PPi and TPP valence). As the pH of the parent solutions was raised above the effective $pK_a$ of PAH, however (i.e., above pH 8.5), the linear charge density of PAH became much lower and the complexes ceased to form. This inability to form colloidal and macroscopic complexes at higher pH-levels indicates that the high linear charge density of PAH is important for its ionic cross-linking.

Furthermore, PAH/PPi and PAH/TPP complexation can cause significant changes in the mixture pH. This stems from shifts in the acid-base equilibria of PAH, PPi and TPP, and is highlighted in the state diagrams in FIG. 14C and FIG. 14D, where the ordinates now indicate the final pH after mixing (recorded after 1 day of equilibration) instead of the parent solution pH. When the PAH was initially not fully protonated (e.g., at a parent solution pH of 7.0 or 8.0), the complexation of its ionized amine groups with PPi or TPP favored its further protonation. This led to a depletion of protons and increased the pH. Conversely, when PPi and TPP were initially not fully deprotonated (which was the case for every pH level examined), their association with PAH drove their further deprotonation, which lowered the ambient pH.

Figure 14C:
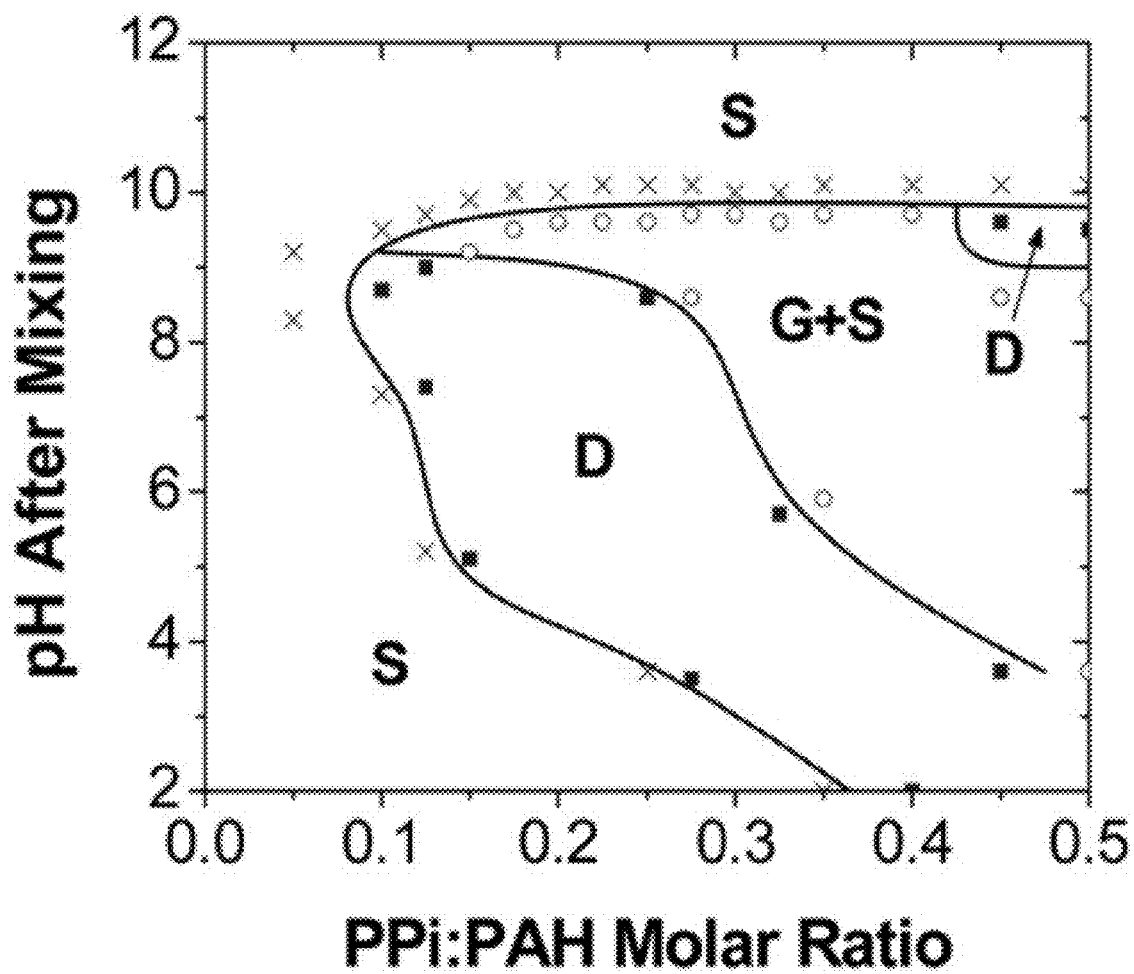
Figure 14D:
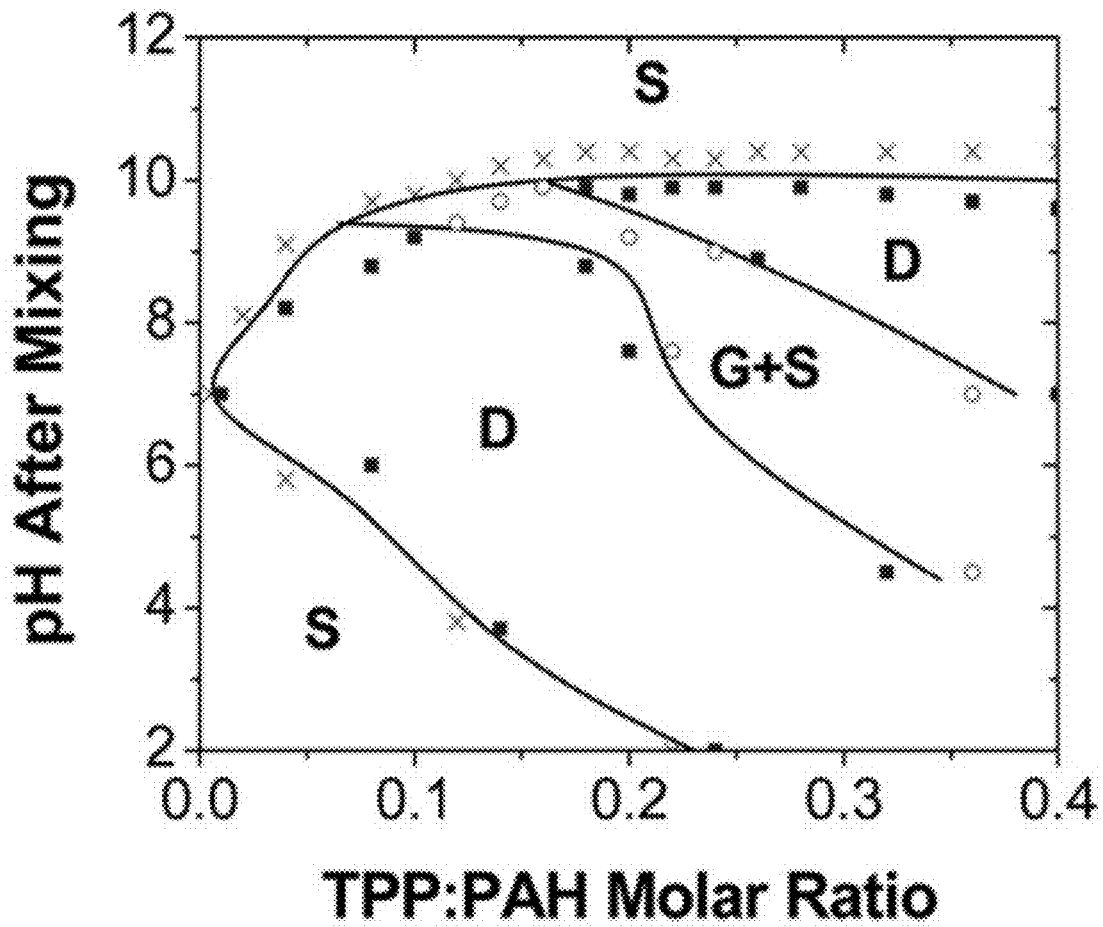

The respective magnitudes of these competing effects on pH depended on the initial PAH, PPi and TPP protonation states. At pH-levels above 7.0, there were significant numbers of uncharged PAH amine groups, while the PPi and TPP were mostly ionized. Thus, the proton uptake by the PAH outweighed their release by the PPi and TPP, and the pH upon PAH/PPi and PAH/TPP mixing increased by up to two full units (FIG. 14C and FIG. 14D). Notably, FIGS. 14C-14D show that upon mixing, the complexes can form at a pH of up to about 10. When the parent solution pH was lower, however, an opposite pH drift sometimes occurred. This was most evident when the parent solution pH was 4.5, where nearly all PAH amine groups were protonated, but the PPi and TPP ions each bore two protons that could be released upon their binding to PAH. Accordingly, ionic cross-linking under these conditions led to a reduction in pH (cf. FIGS. 14A-14D).

The resulting pH drifts occurred regardless of whether insoluble complexes formed (as seen from the vertical shift of many of the data points in the "S" regions; cf. FIGS. 14A, 14C and FIGS. 14B, 14D). This confirmed that PPi and TPP bound to the PAH even in the absence of ionotropic gelation. Once all of the PAH was ionically cross-linked, however, the pH remained nearly constant, irrespective of whether the complexes remained dispersed or were coagulated into macroscopic, gel-like adhesives. This constant pH reflected the fact that little further PPi and TPP binding to PAH occurred under these conditions. The binding-induced pH changes in FIGS. 14A-14D were also consistent with those occurring upon the complexation between weak polyelectrolytes (including PAH), where similar changes in the effective $pK_a$ values and solution pH occur.

Figure 15A:
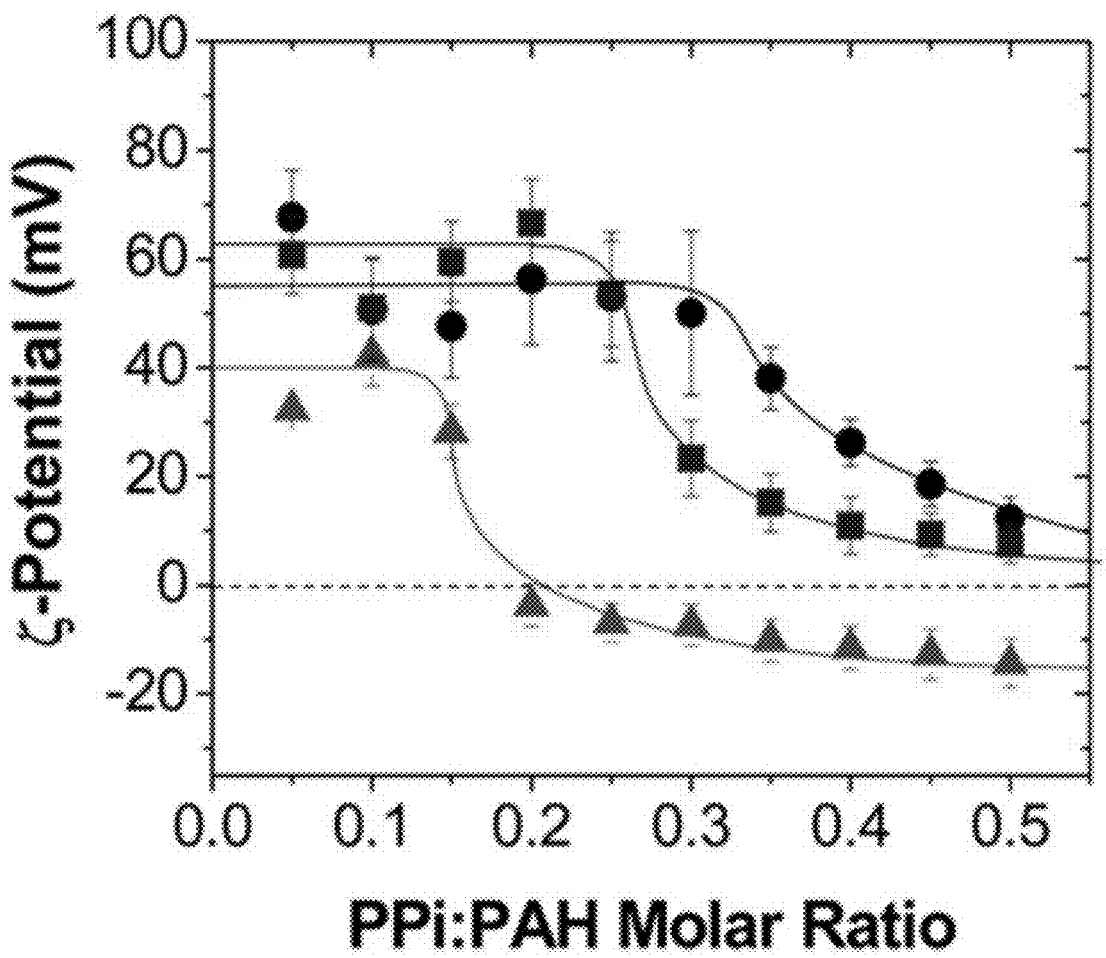
FIGS. 15A-15B: ζ-potentials of colloidal complexes plotted as a function of the ion:monomer molar ratio for the PAH/PPi (FIG. 15A) and PAH/TPP (FIG. 15B) mixtures prepared from PAH, PPi, and TPP solutions at initial pH levels of (black circles) 6.0, (blue squares) 7.0, and (red triangles) 8.0. The lines are guides to the eye.
Figure 15B:
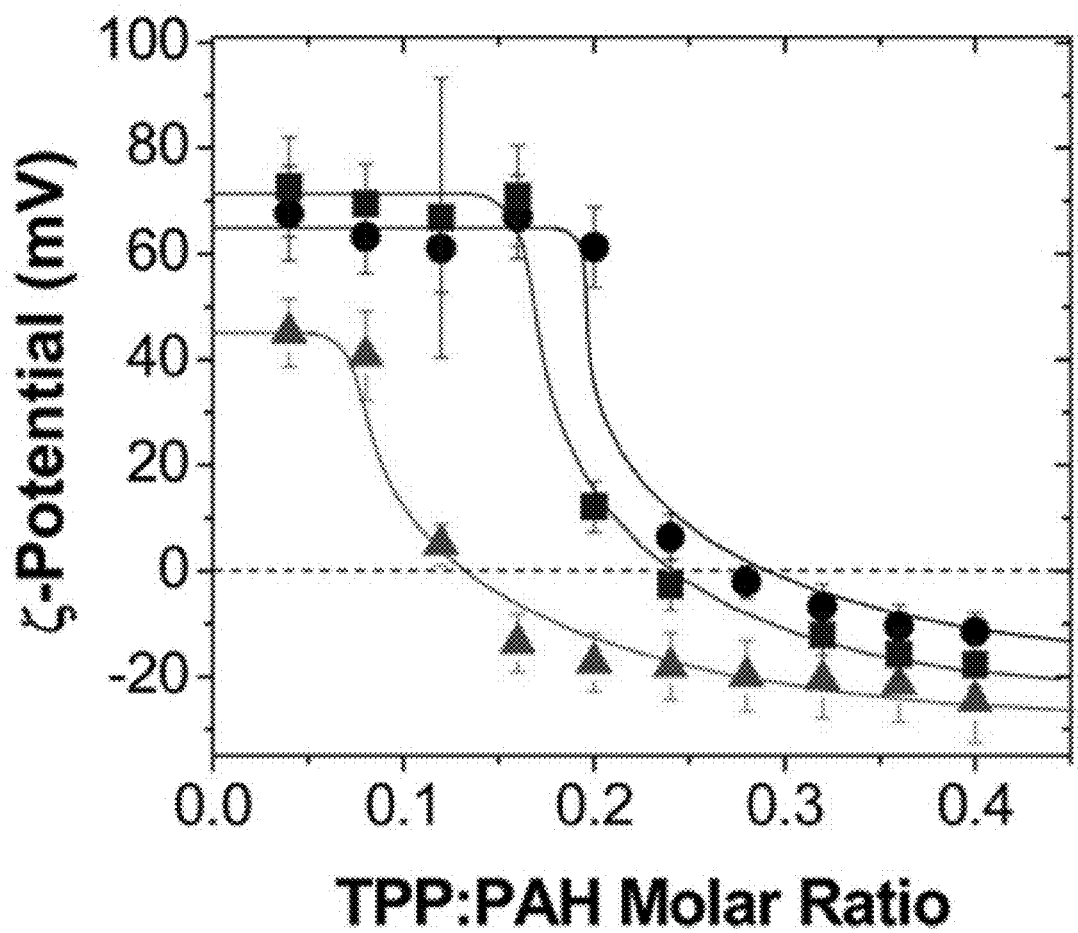

Further insight into the pH effects on the PAH/counterion aggregation states was gained by probing the evolutions in their ζ-potentials upon the titration of PPi and TPP into PAH, using parent solutions at pH 6.0, 7.0, and 8.0 (see FIGS. 15A-15B). Here, colloidal complexes formed from the very first PPi and TPP additions but dissolved upon equilibration if the ion:PAH monomer ratios were below the "S/D" phase boundaries in FIGS. 14A-14B. At each pH, the ζ-potentials stayed roughly constant (at values ranging between +40 and +70 mV) at lower ion:PAH monomer ratios but diminished sharply (to values below +30 mV) once a critical ion:PAH monomer ratio was reached. This drop in ζ-potential corresponded to the point where nearly all of the PAH molecules were ionically crosslinked, and instead of forming new colloidal complexes, the PPi and TPP began to bind to the surfaces of existing ones. Moreover, this sudden drop in ζ-potential corresponded to the point where the colloidal complexes began coagulating into macroscopic adhesives, likely because of: (1) the reduction in electrostatic repulsion between the dispersed colloids and (2) bridging flocculation mediated by the surface-bound PPi or TPP.

As the pH increased, the multivalent ion:PAH monomer ratios at which the ζ-potential reduction occurred decreased, again reflecting the increased ionization of PPi and TPP, and decreased ionization of PAH. Interestingly, this effect was most pronounced when the parent solution pH was raised to 8.0 (i.e., approached the effective $pK_a$ of PAH). This was likely because the charge of PAH near its effective $pK_a$ was much more sensitive to pH than that of PPi and TPP which—due to their widely spaced, multiple $pK_a$ values—exhibited a much slower fractional change in charge as the pH was varied. As the multivalent ion:PAH monomer ratio was increased further, the ζ-potential continued to diminish and, in some cases (i.e., in all PAH/TPP mixtures and in PAH/PPi mixtures that started at pH 8.0), became negative. When the ζ-potential became sufficiently negative (between −10 and −20 mV; see FIGS. 15A-15B), the colloidal dispersions that formed at high multivalent ion:PAH monomer ratios persisted throughout the month-long experiment (cf. FIGS. 14A-14B). While the aggregation states and ζ-potential trends for the PAH/TPP system were all qualitatively consistent with those reported previously for mixtures prepared from parent solutions at pH 7.0, the stable anionic dispersions that formed in PPi-rich PAH/PPi mixtures from parent solutions at pH 8.0 were not seen at lower pH levels. This likely reflected the higher valence of PPi (and therefore its stronger surface adsorption) at the higher pH values.

As the multivalent ion:PAH monomer ratio was increased further, the ζ-potential continued to diminish and, in some cases (i.e., in all PAH/TPP mixtures and in PAH/PPi mixtures that started at pH 8.0), became negative. When the ζ-potential became sufficiently negative (between −10 and −20 mV; see FIGS. 15A-15B), the colloidal dispersions that formed at high multivalent ion:PAH monomer ratios persisted throughout the month-long experiment (cf. FIGS. 14A-14B). While the aggregation states and ζ-potential trends for the PAH/TPP system were all qualitatively consistent with those reported previously for mixtures prepared from parent solutions at pH 7.0, the stable anionic dispersions that formed in PPi-rich PAH/PPi mixtures from parent solutions at pH 8.0 were not seen at lower pH levels. Without wishing to be bound by theory, it is believed this is reflected the higher valence of PPi (and therefore its stronger surface adsorption) at the higher pH values.

Effects of pH on Water Content

In addition to affecting the compositions at which the gel-like adhesives formed, the pH also affected their physicochemical properties. The first property examined was their water content. This was achieved by measuring their mass change upon drying as described above. All adhesive complexes were solute-rich (containing less than 40 wt % water), which reflected their high ionic cross-link densities, and had properties that were insensitive to the multivalent ion:PAH monomer ratios used in their preparation. Yet, the adhesives prepared from solutions at the acidic pH of 6.0 had the lowest water contents, while those prepared from solutions at pH 8.0 had the highest water contents (see Table 3). The amplified water content of adhesives prepared at pH 8.0 (where the final pH-values for PAH/PPi and PAH/TPP mixtures were 10.1 and 10.3, respectively) likely reflected the partial deprotonation of PAH amine groups, which diminished the cross-link density within the ionic networks and increased their swelling. Moreover, the water content might also reflect variations in the multivalent ion:PAH binding stoichiometry, where at lower pH-values more ions are needed to neutralize the PAH amine groups (i.e., because the PPi and TPP valence decreases and PAH ionization increases). The PPi and TPP content within these complexes is therefore likely higher at lower pH values. This explains the reduction in water content at a parent solution pH of 6.0 (where the final PAH/PPi and PAH/TPP mixture pH values were 6.6-6.7) and is consistent with the state diagrams, where more PPi and TPP was needed to form the cross-linked complexes as the pH was diminished.

TABLE 3

Final pH Values and Average Water Contents of Adhesive PAH/PPi and PAH/TPP Complexes Prepared using PAH, PPi, and TPP Solutions at pH 6.0, 7.0, and 8.0 (±Standard Deviation)$^a$.

| initial pH | final pH | | water content (wt %) | |
|---|---|---|---|---|
| | PAH/PPi | PAH/TPP | PAH/PPi | PAH/TPP |
| 6.0 | 6.6 ± 0.1 | 6.7 ± 0.1 | 24.5 ± 0.4 | 25.0 ± 1.1 |
| 7.0 | 8.4 ± 0.1 | 9.1 ± 0.2 | 30.2 ± 0.1 | 26.0 ± 0.1 |
| 8.0 | 10.1 ± 0.2 | 10.3 ± 0.2 | 37.7 ± 0.4 | 37.3 ± 0.8 |

$^a$The final pH values are the readings obtained from the supernatant phases.

Effects of pH on Rheology

Figure 16A:
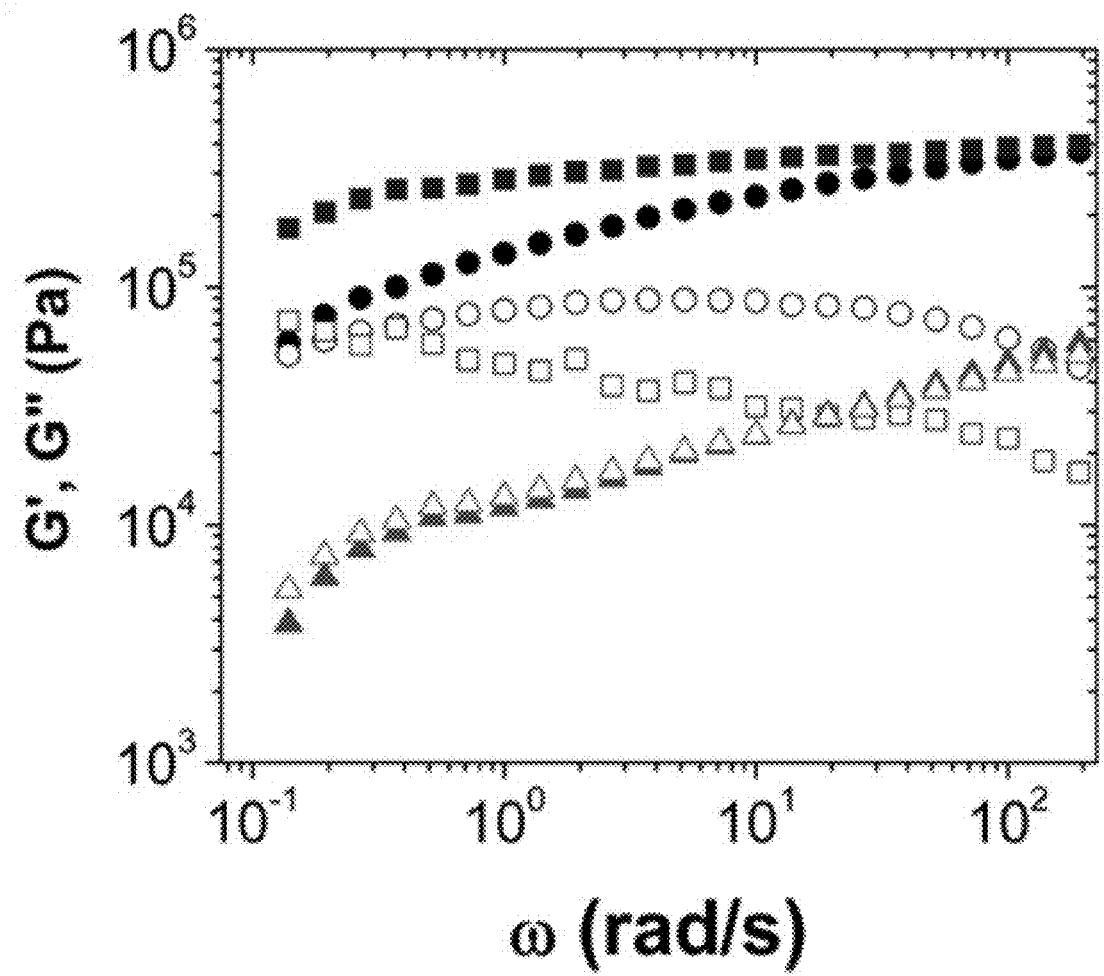
FIGS. 16A-16B: G' (closed symbols) and G" (open symbols) for PAH/PPi (FIG. 16A) and PAH/TPP (FIG. 16B) adhesives prepared at initial pH-levels of (black circles) 6.0, (blue squares) 7.0, and (red triangles) 8.0 and final pH-levels summarized in Table 3.

The pH also had a strong impact on the rheology of PAH/PPi and PAH/TPP adhesives (which was probed as described above). When prepared from solutions at pH 7.0, both materials had storage moduli (G') that exceeded the loss moduli (G") for the entire frequency range tested (thus indicating gel-like properties) and remarkably high $G_\infty$'-values of $4 \times 10^5$ Pa (see FIGS. 16A-16B). Yet, as the preparation pH was decreased to 6.0, there was a reduction in the G'-values at lower frequencies for both adhesive types. Indeed, the PAH/PPi complex exhibited crossover in its G'/G" spectra at $\omega c \sim 0.1$ rad/s, signifying the adhesive complexes to be more fluid-like (FIG. 16A). This decrease in G' likely resulted from the more significant protonation of PPi and TPP ions, which reduced the PAH/PPi and PAH/TPP binding strength and led to faster network relaxation. Moreover, as the preparation pH was increased to 8.0 (i.e., to near the effective $pK_a$ of PAH), there was a drastic decrease in the G'-value with a G'/G" crossover occurring near 10 rad/s for the PAH/PPi complex and near 0.3 rad/s for the PAH/TPP complex. Indeed, in contrast to the complexes prepared at pH 6.0 and 7.0, the $G_\infty$' was not reached for complexes prepared at pH 8.0 over the entire frequency spectrum tested, reflecting their much faster relaxation times. These faster relaxation dynamics likely reflect the deprotonation of PAH amine groups (which weakens the ionic crosslinking) and again indicates that a high polymer linear charge density is essential to preparing gel-like PPi and TPP-crosslinked adhesives.

Figure 16B:
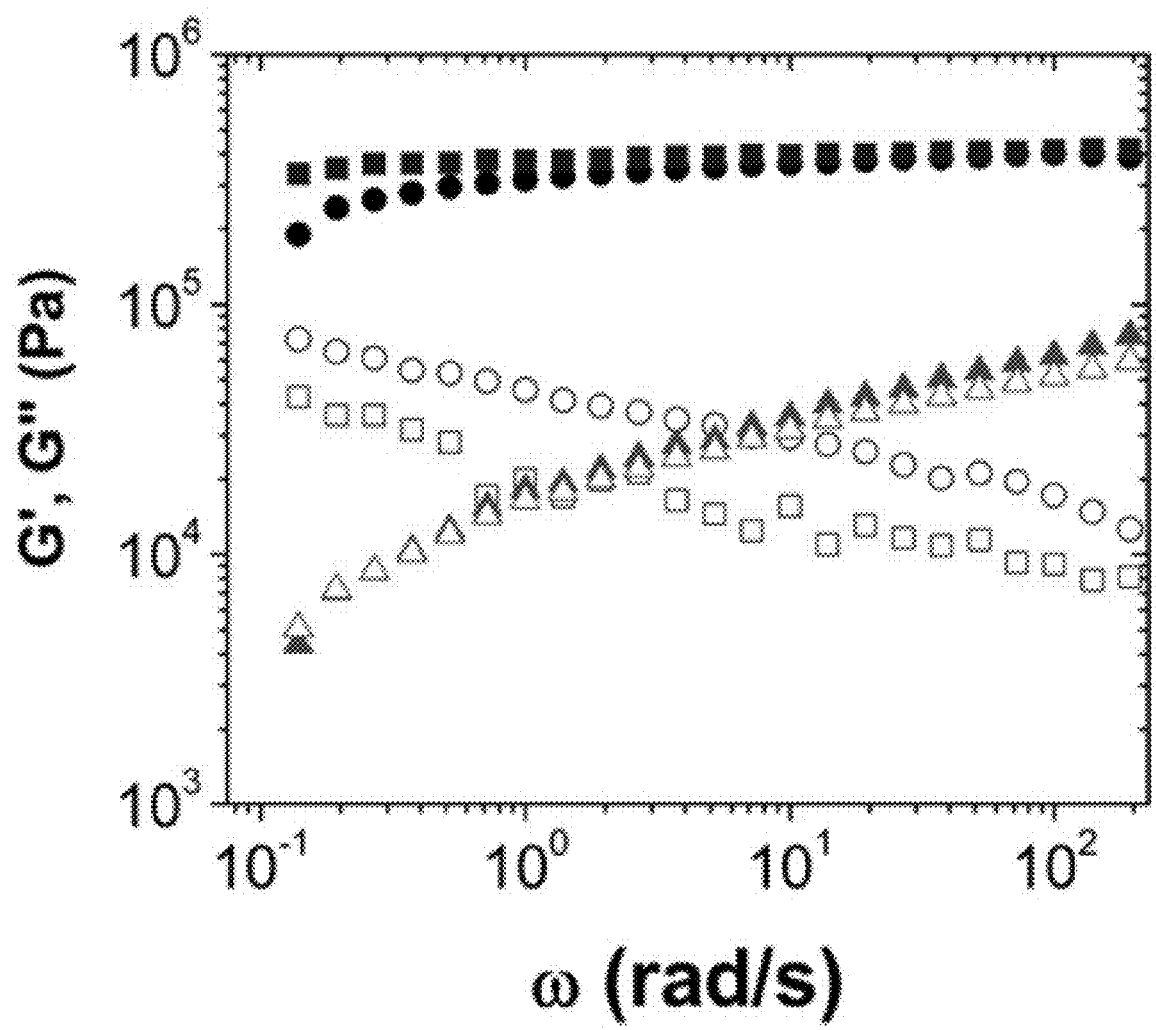

While FIGS. 16A-16B clearly show that PAH/PPi and PAH/TPP complex rheology is acutely sensitive to the pH of the parent PAH, PPi, and TPP solutions, the high moduli of these adhesive coacervates (once they are formed under optimized solutions) appear to persist over a significant range of pH-values. This was revealed by the drastically different final pH-values of the adhesives prepared from parent solutions at pH 7.0 and those prepared from solutions at pH 6.0, where the G' values were not much smaller (despite the dissimilar final pH; see Table 3). Similarly, for the adhesives prepared from solutions at pH 8.0 (where the G' value was drastically diminished), the final supernatant pH exceeded 10 (Table 3). This high variability in final pH-values indicates that, despite their sensitivity to their preparation pH, these adhesive coacervates are robust enough to withstand minor pH fluctuations in their environment. This was confirmed by placing the adhesives prepared from parent solutions at pH 7.0 (whose final pH was 8.4 for the PAH/PPi complexes and 9.1 for PAH/TPP complexes) into water at pH 6.5 and equilibrating them at that pH for 3 days. Although the pH to which the adhesives were exposed was lowered by 1.9-2.6 units, the rheological properties of the adhesives remained essentially unchanged. Interestingly, the relaxation times in these samples were longer than in those that were prepared from parent solutions at pH 6.0 (whose final pH was 6.6-6.7; see Table 3). This difference in relaxation indicates that protonation in PAH/PPi and PAH/TPP complexes might be more sensitive to small changes in their preparation pH than to minor pH fluctuations after they form. When the pH of the same complexes was raised significantly to 10.2 (to match the final pH of complexes prepared at pH 8.0), however, the PAH amine groups were deprotonated, and the rheology of the adhesive complexes became nearly identical to that of those prepared from PAH, PPi, and TPP solutions at pH 8. Similarly, the adhesives became more fluid-like when equilibrated at pH 5.0 and 6.0. This indicates that preformed PAH/PPi and PAH/TPP adhesives can withstand small fluctuations in pH but become more fluid-like (and ultimately dissolve) when exposed to high- and low-pH environments.

Effects of pH on Adhesion Strength

Figure 17A:
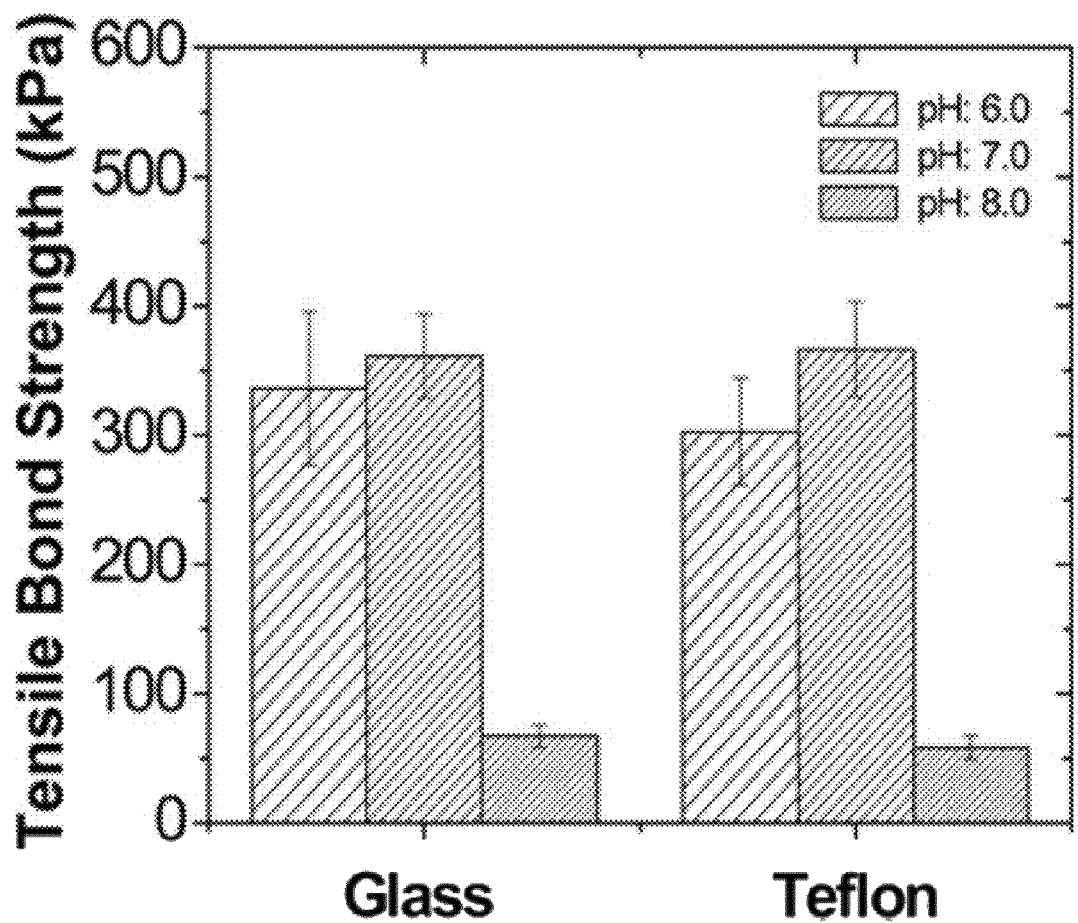
FIGS. 17A-17B: Average tensile bond strengths of PAH/PPi (FIG. 17A) and PAH/TPP (FIG. 17B) complexes prepared from PAH, PPi, and TPP solutions at different pH levels and bonded to glass and Teflon adhesion substrates. The error bars are standard deviations.
Figure 17B:
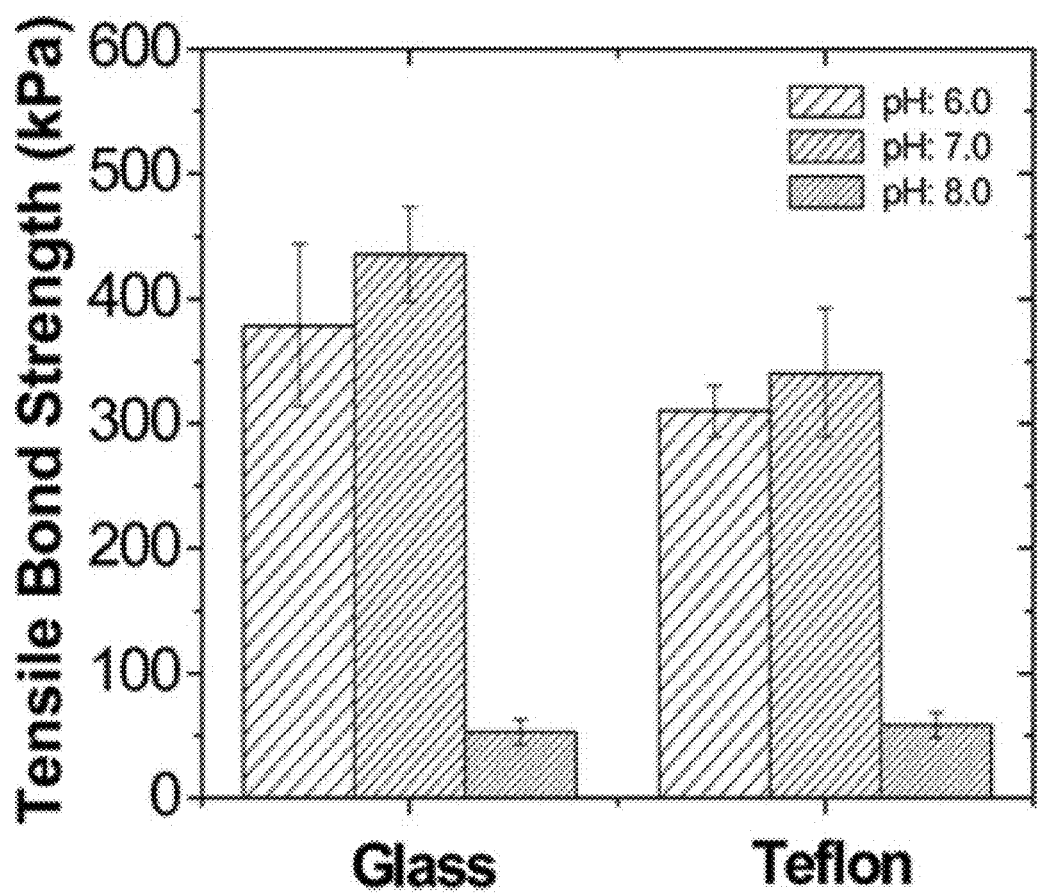

The pH effects on the rheology of PAH/PPi and PAH/TPP complexes also had a strong impact on their underwater adhesion properties. These were probed via tensile adhesion strength measurements, which were performed using glass and Teflon as model hydrophilic and hydrophobic substrates. The short-term tensile adhesion strength was measured by separating two bonded glass or Teflon plates at a rate of 0.85 mm/s. The PAH/PPi and PAH/TPP complexes prepared from solutions at pH 7.0 had the highest average bond strength (see FIGS. 17A-17B). When adhered to glass, the average adhesion strength was 361 kPa for the PAH/PPi complex and 435 kPa for the PAH/TPP complex, while when adhered to Teflon the average adhesion strength was 366 kPa for the PAH/PPi complex and 341 kPa for the PAH/TPP complex. When the parent solution pH was reduced to 6.0, there was a slight (10-20%) reduction in average adhesion strength. Conversely, when the parent solution pH was raised to 8.0, a drastic (over 80%) reduction in adhesion strength occurred, where all tensile bond strengths diminished to around 60 kPa (FIGS. 17A-17B).

While for the glass substrate the adhesion failure was always cohesive, the failure mode for the adhesion to Teflon was pH-dependent. The bonds failed adhesively (at the adhesive-substrate interfaces) when the adhesives were prepared at pH 6.0 and 7.0, but underwent cohesive failure when the adhesives were prepared at pH 8.0. These trends in short-term adhesion strength (and shift from adhesive to cohesive failure in the Teflon-bonded complexes) indicate that the pH sensitivity of the adhesion achieved using the PAH/PPi and PAH/TPP complexes primarily stems from changes in their cohesive strength. They also confirm that, in addition to triggering their dissolution (e.g., by raising the ambient solution pH to 12), changes in pH can strongly affect their underwater adhesion strength.

Figure 18:
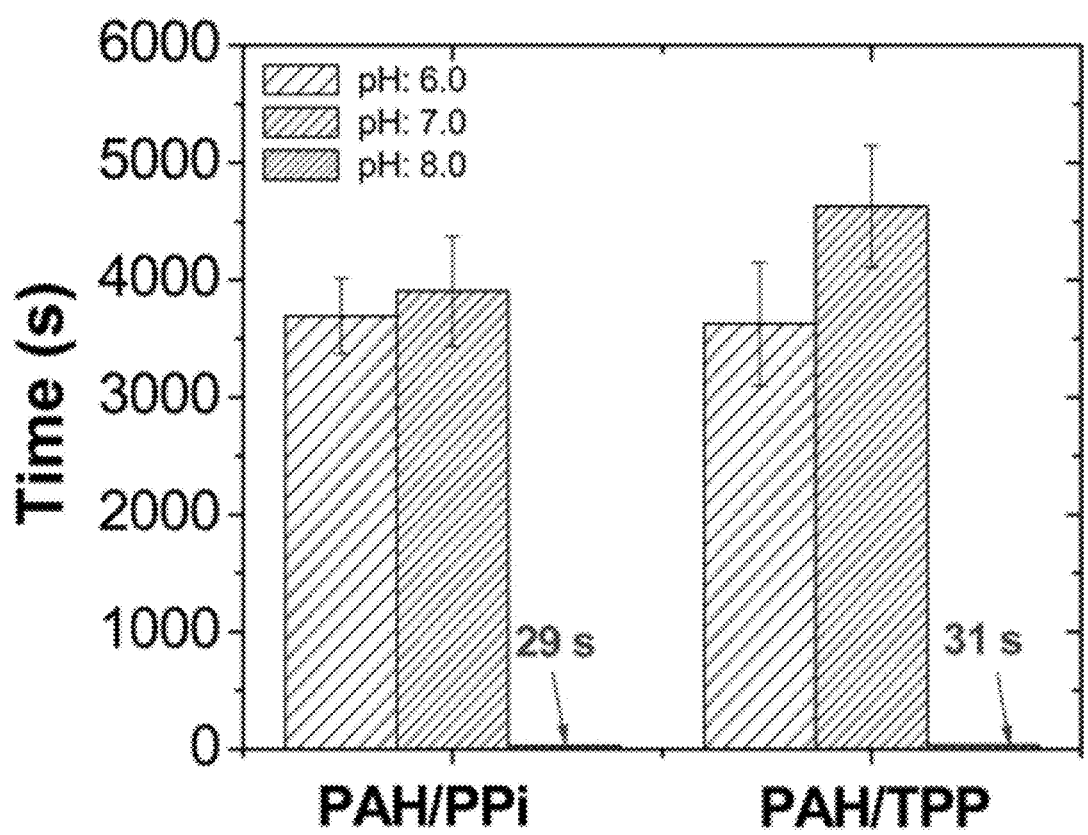
FIG. 18: Average bond longevity achieved by the PAH/PPi and PAH/TPP adhesives prepared using PAH, PPi, and TPP solutions at various pH levels under a 17.8-kPa tensile stress when adhered to glass. The error bars are standard deviations (n=3).

Furthermore, while the PAH/PPi and PAH/TPP adhesives exhibited significant adhesion strengths over short times, the reversibility of their ionic cross-links made them susceptible to plastic deformation (and ultimate failure) when subjected to sustained stress. To quantify this phenomenon, the bonds that these adhesive complexes formed between two glass plates were subjected to a sustained 17.8-kPa tensile stress, whereupon the times required for each bond to fail were recorded. Consistent with the short-term adhesion tests, the bond longevity was highly sensitive to the pH of the parent PAH, PPi and TPP solutions (see FIG. 18). The PAH/PPi and PAH/TPP samples prepared from solutions at pH 7.0 supported the stress the longest, followed closely by those prepared at pH 6.0, where each bond on average lasted over an hour. Conversely, bonds formed by the complexes prepared at pH 8.0 lasted for only around 30 s. This indicates that these underwater adhesives yield the most durable bonds when prepared from solutions at near-neutral pH (where both PAH and cross-linking ions are highly ionized), again reflecting the variations in their cohesive strength.

Effects of Ionic Strength on Complex Formation

Because their various potential uses may subject these underwater adhesives to different ionic strengths, the effect of NaCl concentration on PAH/PPi and PAH/TPP complexes was also investigated. Here, the aggregation states of PAH/PPi and PAH/TPP mixtures prepared from parent PAH, PPi and TPP solutions at pH 7.0 were monitored at various ion:monomer molar ratios and NaCl concentrations. When no NaCl was added, colloidal dispersions formed above a PPi:PAH molar ratio of 0.11:1 and a TPP:PAH molar ratio of 0.01:1 and coagulated above a PPi:PAH molar ratio of 0.26:1 and a TPP:PAH molar ratio of 0.19:1 (see FIGS. 19A-19B). Above a TPP:PAH molar ratio of 0.25:1, however, the coagulation was slowed to the point that the complexes remained dispersed throughout the month-long experiment, while the PAH/PPi mixtures continued to coagulate even at a 0.50:1 PPi:PAH ratio. The multivalent ion:PAH monomer ratio at which PAH/PPi colloidal dispersions began forming was completely insensitive to the NaCl concentration (see "S/D" phase boundary in FIG. 19A). Similarly, the onset of dispersion formation in PAH/TPP mixtures shifted from 0.01:1 to 0.09:1 when 5 mM NaCl was added but remained fixed at 0.09:1 as the NaCl concentration was raised from 5 to 500 mM (FIG. 19B). The 0.09:1 TPP:PAH molar ratio was also the molar ratio at which colloidal complexes formed under NaCl-free conditions when higher PAH concentrations (>6±2 mM) were used, which indicates that the previously reported sensitivity of the "S/D" phase transition to the PAH concentration was an ionic strength effect. The insensitivity of the phase boundary to further NaCl addition, however, indicates that PAH/PPi and PAH/TPP complex formation is (aside from PAH/TPP mixtures at very low ionic strengths) insensitive to monovalent salt.

Figure 19A:
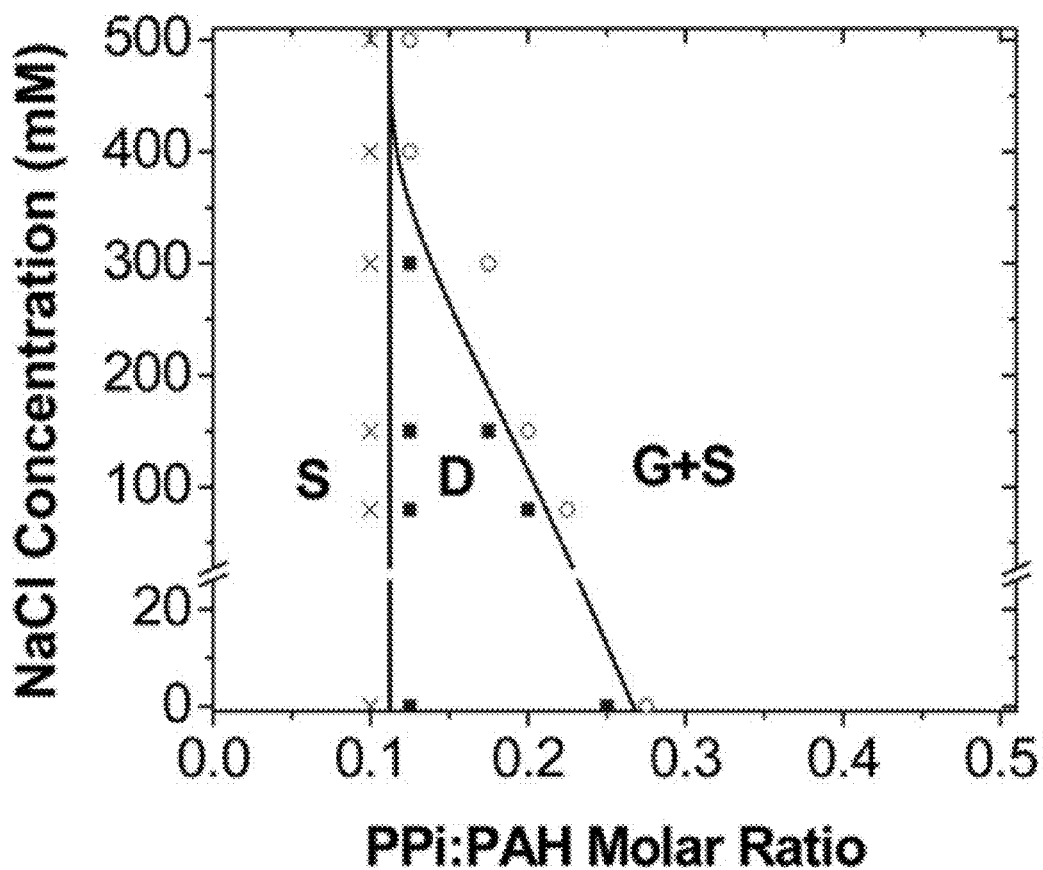
FIGS. 19A-19B: State diagrams for PAH/PPi (FIG. 19A) and PAH/TPP (FIG. 19B) mixtures at NaCl concentrations between 0 and 500 mM after 1 month of equilibration. The data points show the compositions of the samples tested, while the lines indicate the boundaries between the solution (S), dispersion (D), and gel-like aggregation states (G).
Figure 19B:
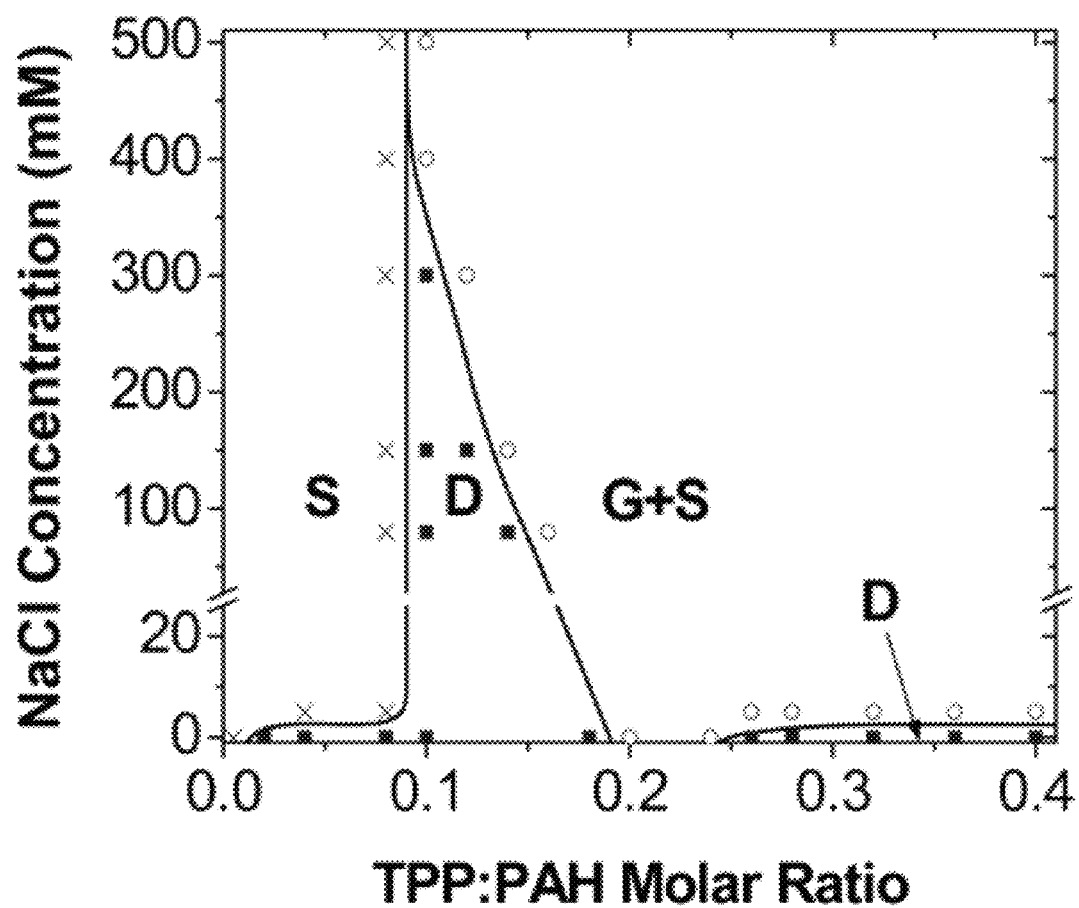

Despite the insensitivity of PAH/PPi and PAH/TPP complexation to the ionic strength, NaCl had a significant impact on the PPi:PAH and TPP:PAH molar ratios where these complexes coagulated into macroscopic adhesives, which decreased as the NaCl concentration increased (see "D" to "G+S" transitions in FIGS. 19A-19B). Indeed, at NaCl concentrations above 400 mM, the mixtures changed directly from solutions to macroscopic adhesives as the multivalent ion:PAH monomer ratios were increased, with no stable dispersions forming in between. The NaCl effect on the coagulation of PAH/TPP dispersions that formed at higher TPP:PAH molar ratios was even more drastic, with colloidally stable dispersions ceasing to form even at 5 mM NaCl (FIG. 19B).

Figure 20A:
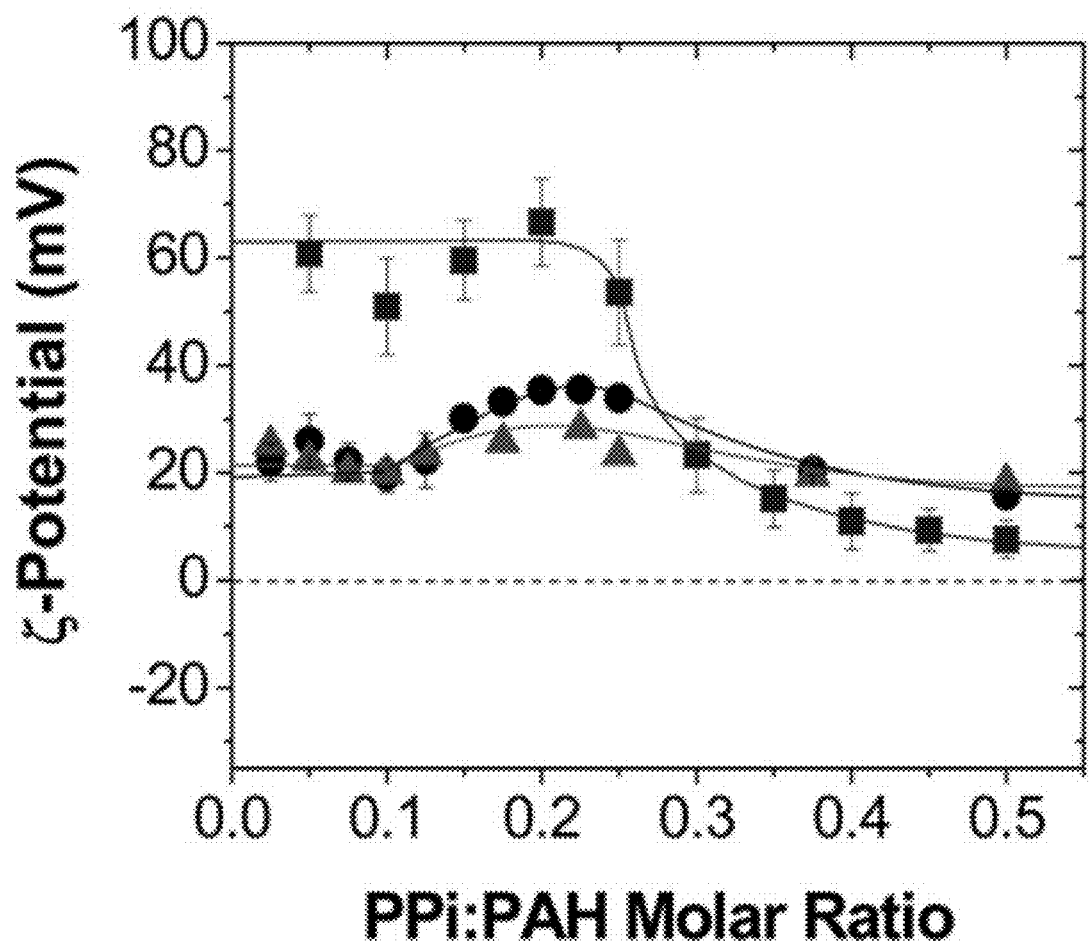
FIGS. 20A-20B: ζ-potentials of colloidal complexes plotted as a function of the ion:PAH monomer molar ratio for the PAH/PPi (FIG. 20A) and PAH/TPP (FIG. 20B) mixtures at (blue squares) 0, (black circles) 150, and (red triangles) 500 mM NaCl concentrations. The lines are guides to the eye.
Figure 20B:
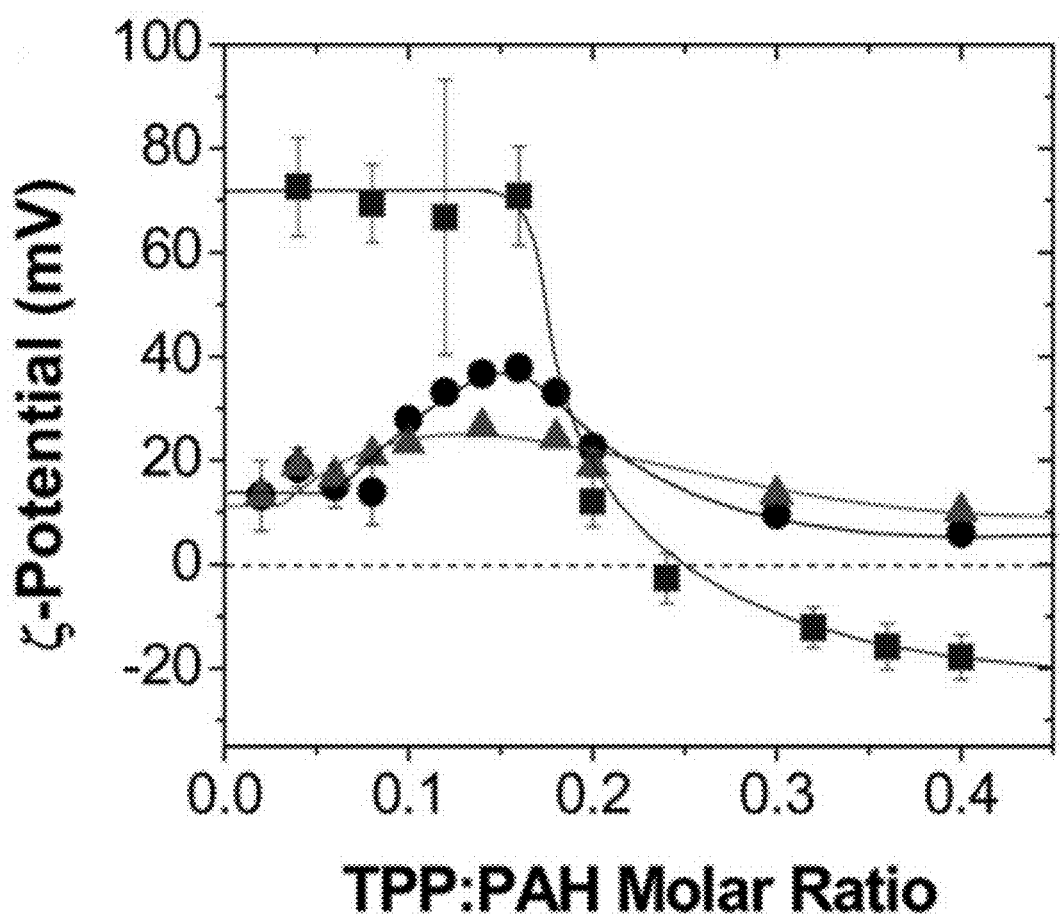

To further analyze the NaCl effects on the aggregation states, $\zeta$-potential measurements were performed. Unlike the $\zeta$-potential curves at varying pH-levels, which kept their general shapes but shifted in the ion:monomer molar ratios where the precipitous $\zeta$-potential drop occurred (cf. FIGS. 15A-15B), NaCl addition drastically changed the shape of the $\zeta$-potential curves (see FIGS. 20A-20B). Without added NaCl, the colloidal complexes that formed at PPi:PAH molar ratios below 0.26:1 and TPP:PAH molar ratios below 0.19:1 had consistently-high $\zeta$-potentials (+50 to +70 mV) and were very stable. At the 150 and 500 mM NaCl concentrations, however, the apparent $\zeta$-potentials were much lower and (especially in 150 mM NaCl) increased at the ion:monomer ratios where the complexes began to form (see FIGS. 19A-19B). For PAH/PPi mixtures, this difference in curve shape was attributed to variations in the ionic cross-linking kinetics (which become much slower at higher NaCl concentrations). Without added NaCl, the colloidal complexes initially formed even when the overall sample compositions were in the "S" regions in the state diagrams (due to the elevated local PPi concentrations during their titration into the PAH solution). Thus, $\zeta$-potentials reflective of colloidal complexes were detected from the beginning of the titrations (although the unstable complexes at low PPi:PAH monomer ratios dissolved after 1 day). Conversely, when NaCl was added to the mixtures, the colloid formation was much slower. Thus, the PPi was uniformly mixed into the PAH solution before the colloidal complexes could assemble, and no colloidal complexes formed during the titrations until the compositions reached the "D" region in FIG. 19A (where the peaks in the $\zeta$-potential curves were detected; see FIG. 20A). While the same kinetic arguments apply to the PAH/TPP mixtures, the compositions tested in the $\zeta$-potential titrations under the NaCl-free condition were all in the "D" region in FIG. 19B (cf. FIG. 19B and FIG. 20B). Thus, the altered shape of the PAH/TPP $\zeta$-potential curves also reflected a salt-triggered-shift in the "S/D" phase boundary. Furthermore, because the $\zeta$-potentials and the electrostatic repulsion between the complexes were lower at higher salt concentrations, the PAH/PPi and PAH/TPP complexes were more prone to coagulation at lower multivalent ion:PAH monomer ratios. This was especially true in 500 mM NaCl, where the $\zeta$-potentials never rose above +30 mV (FIGS. 20A-20B), and due to their weakened electrostatic repulsion, the colloidal PAH/PPi and PAH/TPP complexes rapidly coagulated within 1 h of their formation.

At higher ion:PAH monomer ratios, where the $\zeta$-potentials began to decrease with the ionic cross-linker concentration, the $\zeta$-potential reduction became less drastic at higher ionic strengths. Indeed, at high ion:monomer ratios the $\zeta$-potentials increased with NaCl concentration (and no charge inversion occurred in the PAH/TPP system in the presence of added NaCl). This was consistent with previous work on chitosan/TPP mixtures (where NaCl made the $\zeta$-potentials of chitosan/TPP microgels less sensitive to further TPP addition) and on multivalent ion adsorption to polyelectrolyte brushes, and likely reflected the competitive binding of monovalent ions to cross-link-forming ionic groups. Interestingly, when charge inversion occurred, the colloidal complexes remained dispersed for one month even though the $\zeta$-potentials (which ranged between −10 and −20 mV) were quite low. This indicates that the coagulation rates in PAH/PPi and PAH/TPP mixtures depend on both the colloidal collision frequency-which increases with NaCl concentration due to reduced electrostatic repulsion—and the probability of ionic bridging (which likely diminishes upon charge inversion due to a lack of free amine groups).

Effects of Ionic Strength on Water Content

As indicated by the ζ-potential measurements, the strength of PAH/PPi and PAH/TPP binding decreased with the NaCl concentration. Because of this impact on ionic cross-linking strength, the salt effect on the ionic network swelling was opposite to that in covalently cross-linked polyelectrolyte networks. Instead of collapsing upon the addition of NaCl, PAH/PPi and PAH/TPP networks increased their water content (albeit modestly) with increasing NaCl concentration (see Table 4). This effect indicated a reduction in crosslink density caused by the weaker PPi and TPP binding and was more significant for the PAH/PPi adhesives than PAH/TPP adhesives (presumably because TPP forms stronger cross-links than PPi).

TABLE 4

Final pH Values and Average Water Contents of Adhesive PAH/PPi and PAH/TPP Complexes Prepared at Different NaCl Concentrations and a Parent PAH, PPi, and TPP Solution pH of 7.0 (±Standard Deviation)$^a$.

| [NaCl] (mM) | final pH | | water content (wt %) | |
|---|---|---|---|---|
| | PAH/PPi | PAH/TPP | PAH/PPi | PAH/TPP |
| 0 | 8.4 ± 0.2 | 9.1 ± 0.2 | 30.2 ± 0.1 | 26.0 ± 0.1 |
| 150 | 6.7 ± 0.1 | 6.4 ± 0.1 | 31.3 ± 0.6 | 28.0 ± 0.6 |
| 300 | 6.7 ± 0.1 | 6.4 ± 0.1 | 36.9 ± 0.6 | 28.9 ± 0.1 |

$^a$The final pH values are the readings obtained from the supernatants.

Notably, the ionic strength also affected the pH drift during PAH/PPi and PAH/TPP complexation (Table 4). Although the parent solution pH was 7.0 in each case, complexation at 0 mM NaCl increased the pH to 8.4-9.1, while complexation in 150 and 300 mM NaCl decreased the pH to 6.4-6.7. This difference reflected the ionic strength effects on the polyelectrolyte $pK_a$, where higher ionic strengths favored higher solution-phase PAH ionization and therefore diminished the PAH effect on the pH drift. Despite these variations in pH, however, the increase in water content caused by the added salt was opposite to that expected with a pH reduction (cf. Table 3) and confirmed that the swelling was a salt (rather than a pH) effect.

Effects of Ionic Strength on Rheology

Figure 21A:
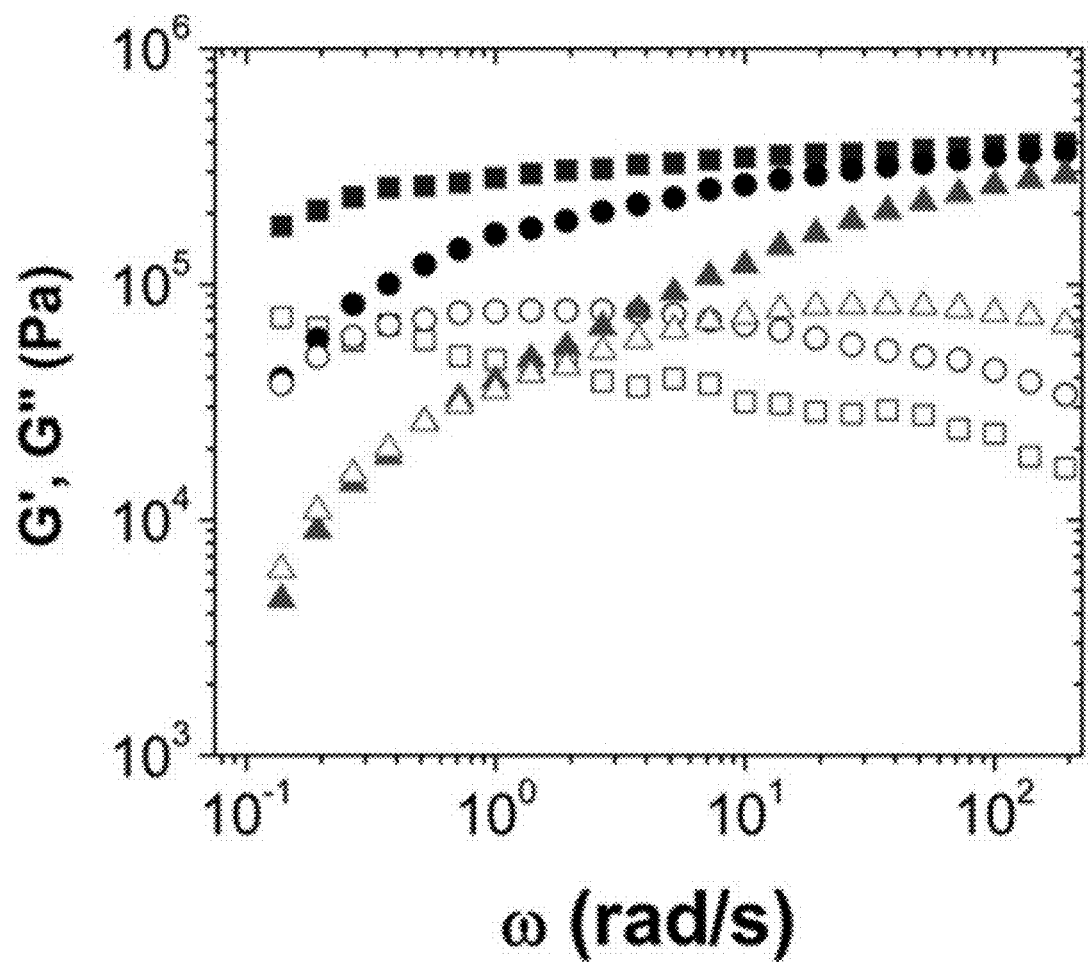
FIGS. 21A-21B: G' (closed symbols) and G" (open symbols) for PAH/PPi (FIG. 21A) and PAH/TPP (FIG. 21B) adhesives prepared in (blue squares) 0 mM NaCl, (black circles) 150 mM NaCl, and (red triangles) 300 mM NaCl.
Figure 21B:
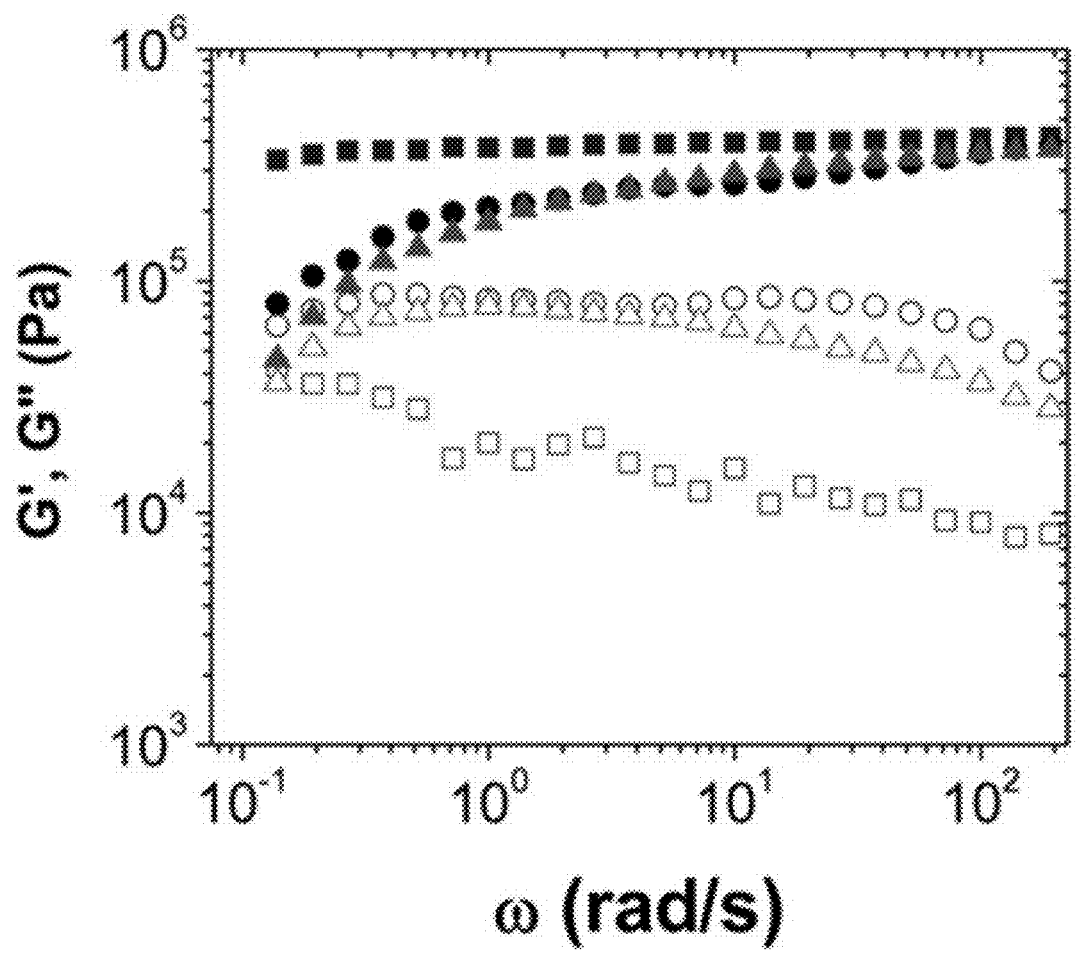

The weaker ionic cross-linking at higher NaCl concentrations also affected the rheology of PAH/PPi and PAH/TPP complexes. Despite the modest salt-induced changes in the water contents of these adhesives, their $G_\infty'$-values (and therefore their network densities) appeared to be insensitive to salt (see FIGS. 21A-21B). Yet, as the NaCl concentration was increased from 0 to 150 mM, there was a decrease in the G'-values at lower frequencies for both adhesive types, with G'/G" crossover occurring at ωc~0.1 rad/s and corresponding to a roughly 10 s relaxation time. This decrease in relaxation time indicated that both adhesives became more fluid-like and was qualitatively consistent with the salt effects reported for polyelectrolyte complexes (i.e., complexes between oppositely charged polymer species).

As the NaCl concentration was increased further (to 300 mM), there was an additional decrease in the G'-values at lower frequencies for the PAH/PPi complex (with the crossover occurring at an even higher frequency; ωc~0.5 rad/s). Conversely, the rheology of the PAH/TPP complex exhibited little change as the NaCl concentration was raised from 150 to 300 mM, thus indicating the rheological properties of PAH/PPi adhesives to be more sensitive to NaCl concentration than those of PAH/TPP adhesives. This was consistent with the weaker impact of NaCl on the PAH/TPP water content and again likely reflected the stronger PAH/TPP binding. These salt-induced changes in relaxation dynamics were roughly the same regardless of whether the NaCl was added before or after the complexes formed. Interestingly, adhesive gels stored in a supernatant at 150 mM NaCl concentration after originally prepared with no added NaCl had very similar rheology to those originally prepared in 150 mM NaCl.

Effects of Ionic Strength on Adhesion Strength

Figure 22A:
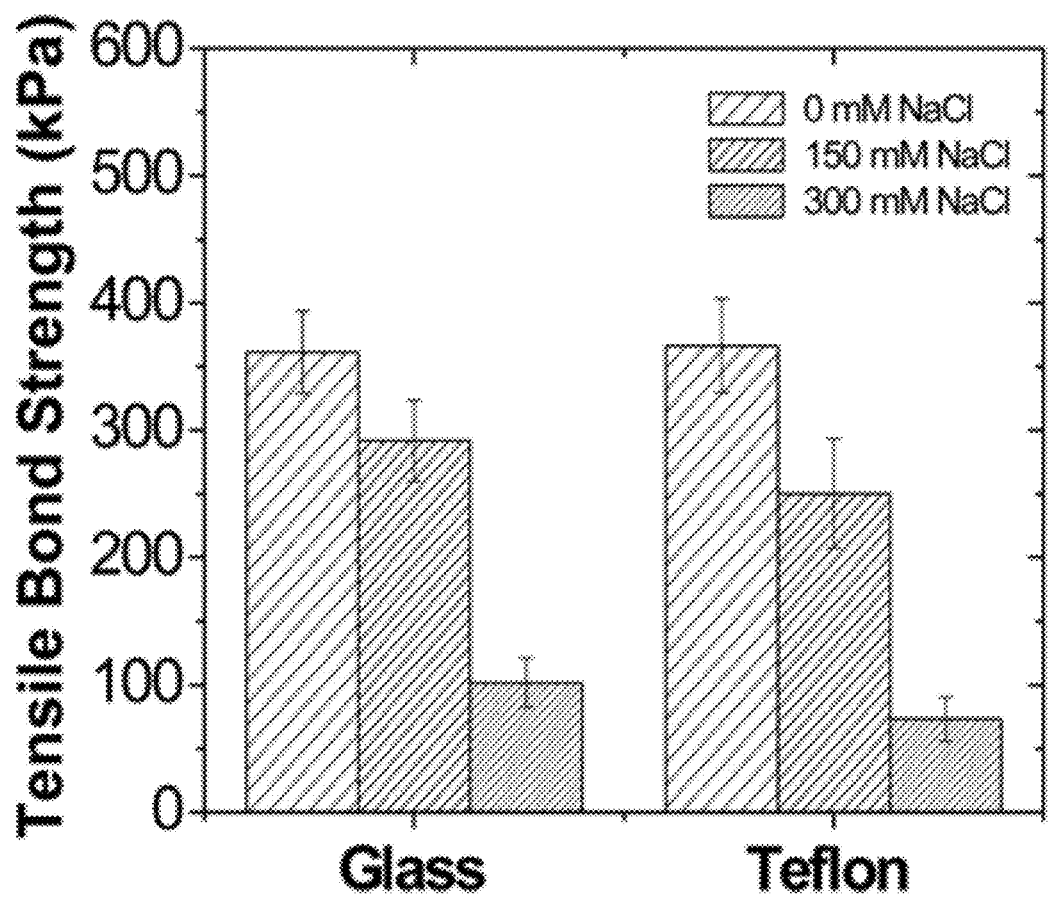
FIGS. 22A-22B: Average tensile bond strengths of the PAH/PPI (FIG. 22A) and the PAH/TPP (FIG. 22B) complexes prepared at different NaCl concentrations bonded to glass and Teflon adhesion substrates. The error bars are standard deviations (n=6).
Figure 22B:
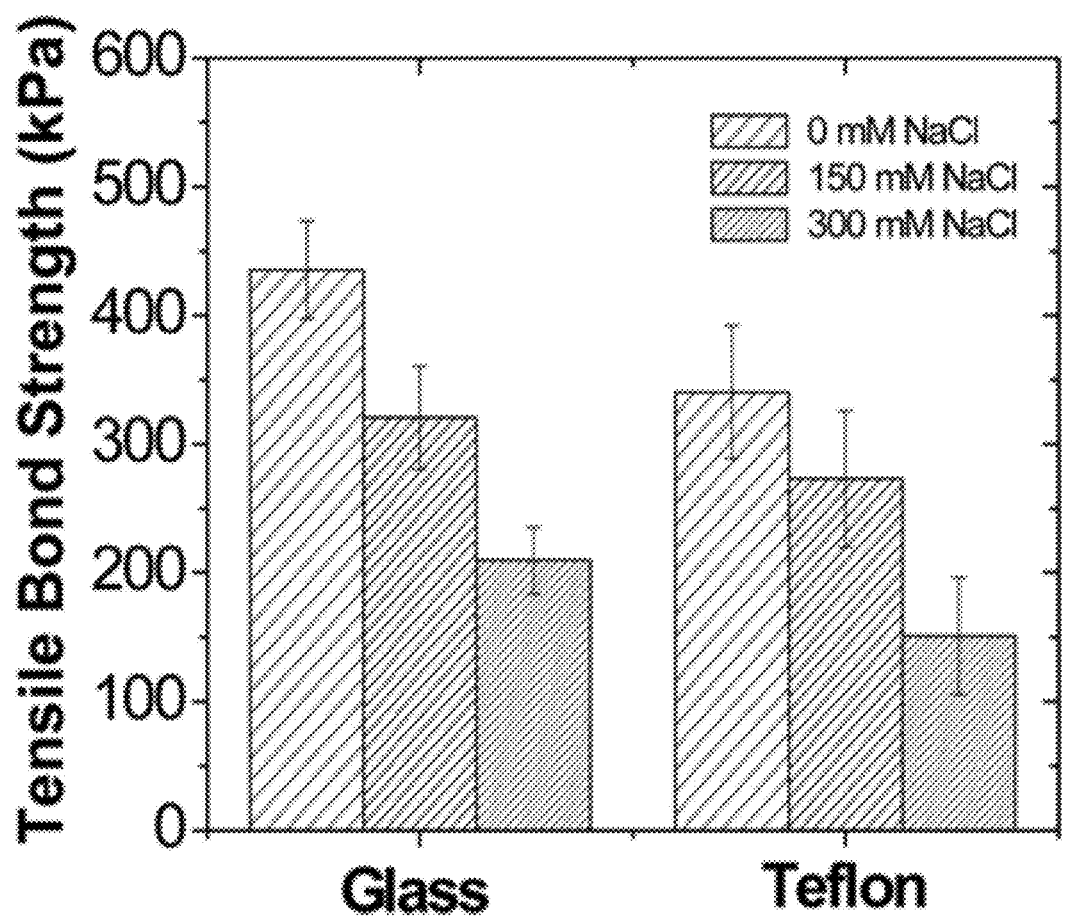

The ionic strength also affected the underwater adhesion strength mediated by the PAH/PPi and PAH/TPP complexes. The adhesive complexes prepared without added NaCl yielded the highest tensile bond strengths, which became weaker at higher ionic strengths (see FIGS. 22A-22B). As indicated by the rheology data, this salt effect was stronger for the PAH/PPi complexes than for the PAH/TPP complexes (especially in 300 mM NaCl, where the adhesion strength of the PAH/TPP complex was twice that of the PAH/PPi complex). Moreover, while the reduction in adhesion strength in 300 mM NaCl was 2-4-fold, the reduction in average adhesion strength in 150 mM NaCl (which roughly corresponds to near-physiological ionic strength) was only modest (roughly 20-30%; with short term bond strengths still ranging between 250 and 321 kPa). At each salt concentration the mode of bond failure was cohesive for the glass substrate and adhesive for the Teflon substrate. This indicates that elevated ionic strengths diminish both the cohesive strength of the ionic networks and the strengths of their interfacial interactions.

Figure 23:
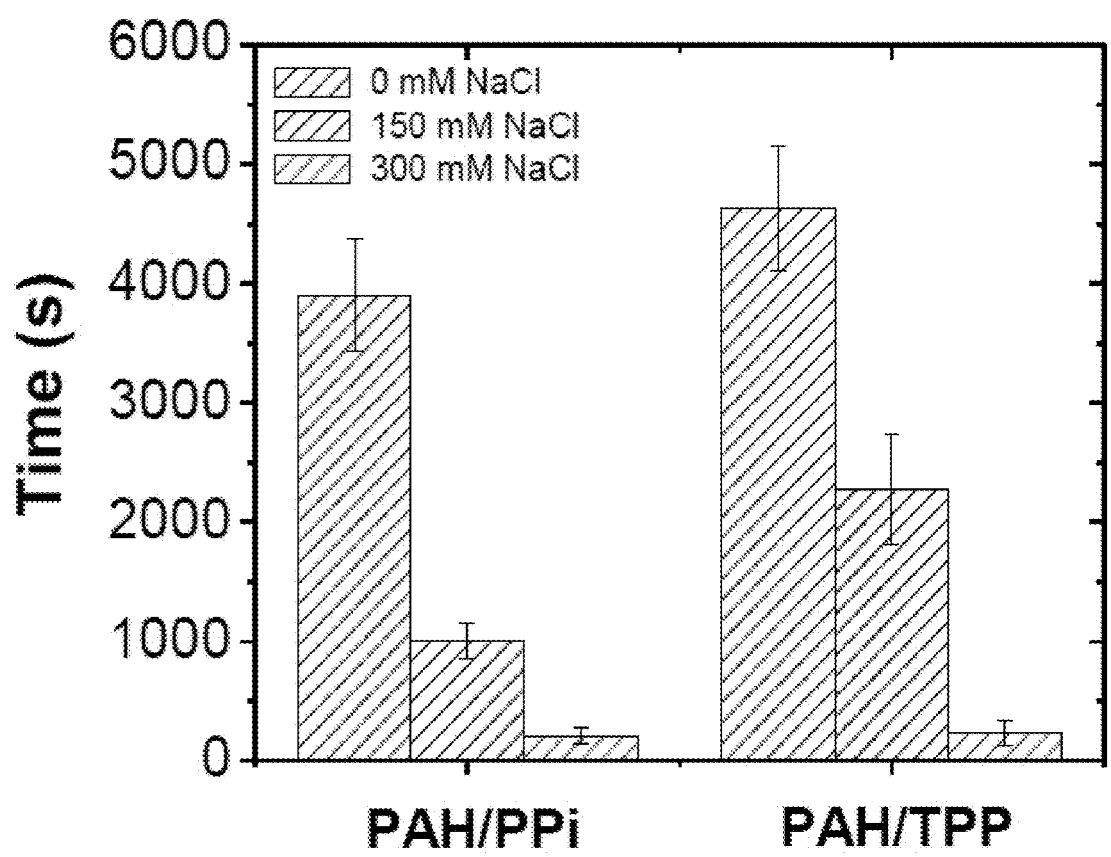
FIG. 23: The average bond longevity achieved by the PAH/PPi and the PAH/TPP adhesives prepared at different NaCl concentrations under a 17.8 kPa tensile stress when adhered to glass. The error bars are standard deviations (n=3).

The addition of NaCl had an even stronger effect on adhesion longevity. When the adhesives were prepared in 150 mM NaCl, the average duration of their adhesion to glass (under a sustained 17.8-kPa tensile stress) diminished greatly, from roughly 3900 to 1000 s for the PAH/PPi complexes and from roughly 4600 to 2300 s for the PAH/TPP complexes. This reduction in bond longevity was even more drastic when the adhesives were formed in 300 mM NaCl, where the bonds created by the PAH/PPi and PAH/TPP complexes lasted only 202 and 230 s, respectively. This 5-10-fold further reduction in bond longevity was surprising in the case of the PAH/TPP complexes, whose rheology in 150 and 300 mM NaCl was quite similar (see FIG. 23), and may have reflected rheological differences at low ω-values outside the experimental frequency range. In summary, the reduction in PAH/PPi and PAH/TPP adhesion longevity at higher salt concentrations is even more drastic than that of their short-term adhesion strength and indicates that these complexes form their strongest and most durable bonds at lower ionic strengths.

Injectability

Figure 9A:
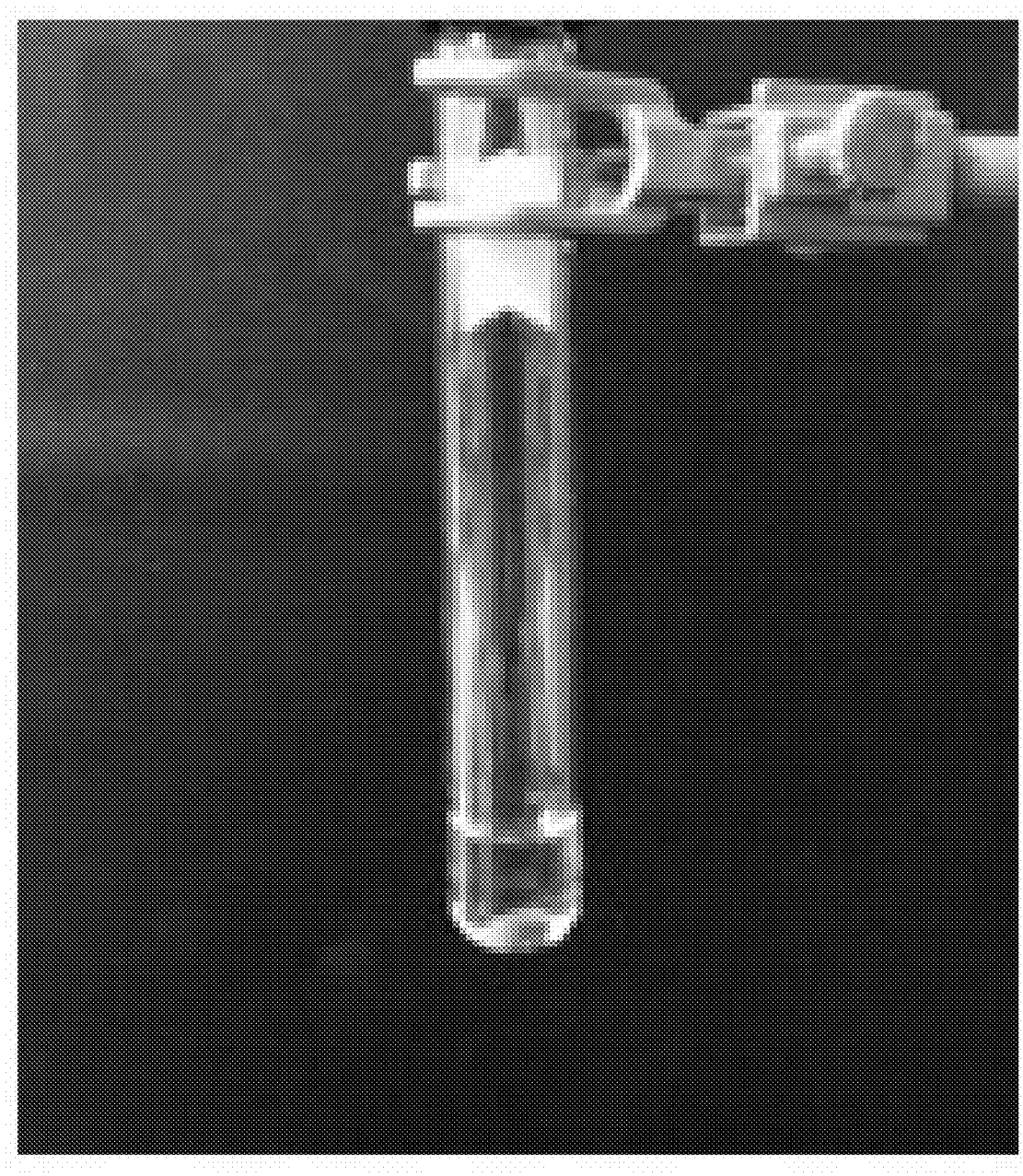
FIGS. 9A-9D: Photographs showing a 1×PBS and (blue) magnetic stir bar in a test tube prior to injection of the dispersion (FIG. 9A), the dispersion being injected into the 1×PBS (FIG. 9B), the dispersion/PBS mixture immediately after injection (FIG. 9C), and the test tube inverted 5 minutes after the injection with the magnetic stir bar adhered to the glass with a thin layer of gel (FIG. 9D).
Figure 9B:
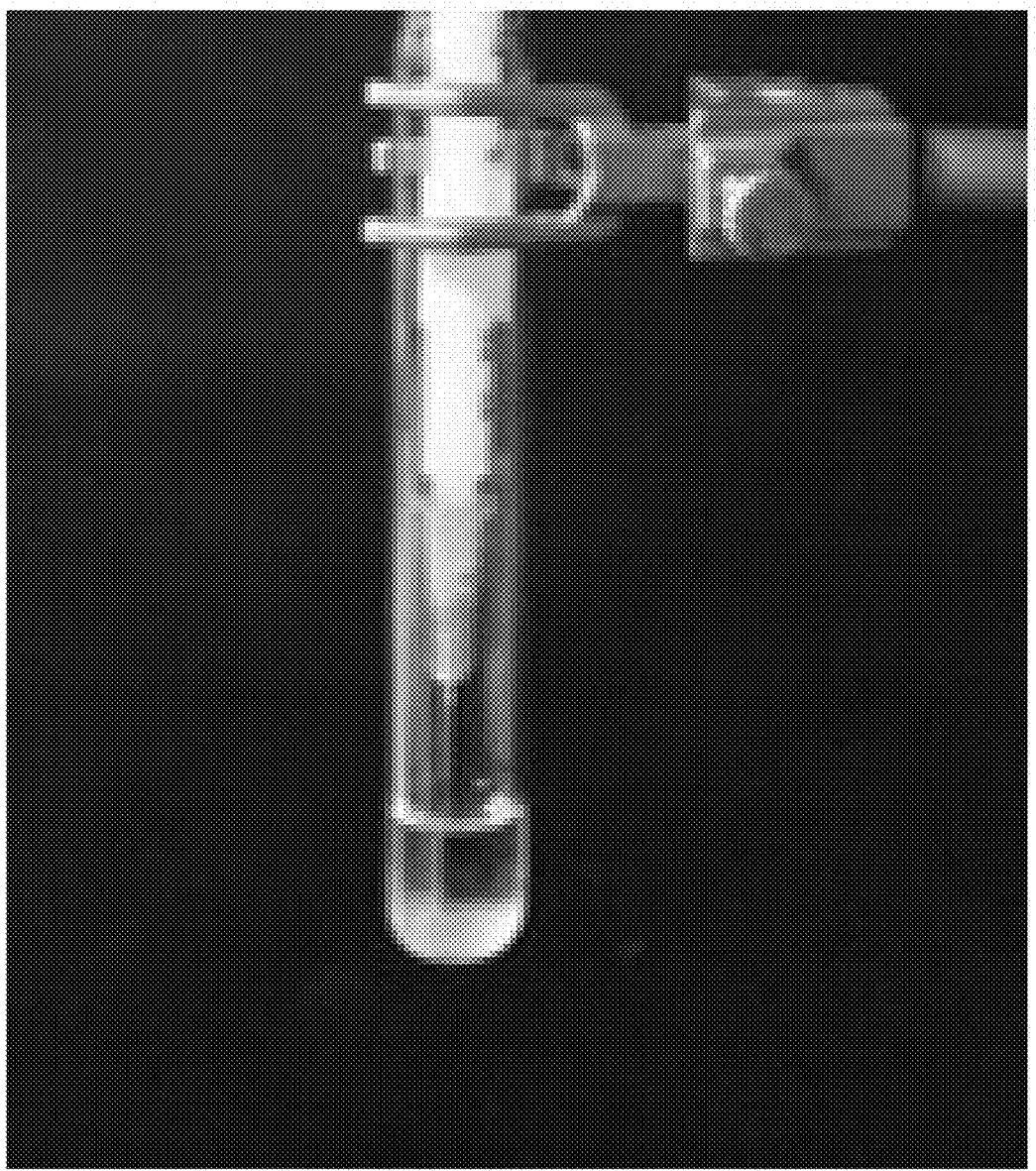
Figure 9C:
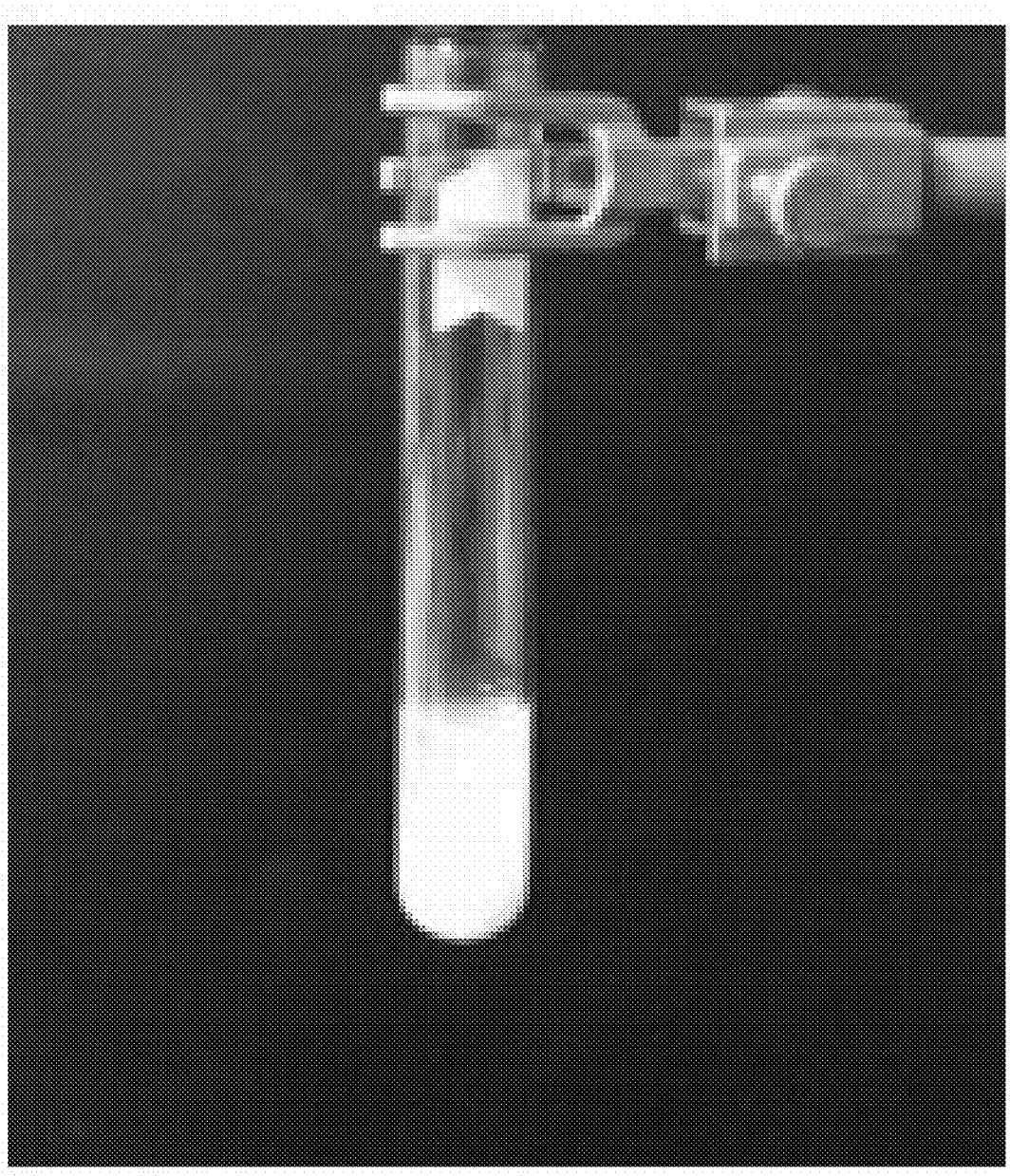
Figure 9D:
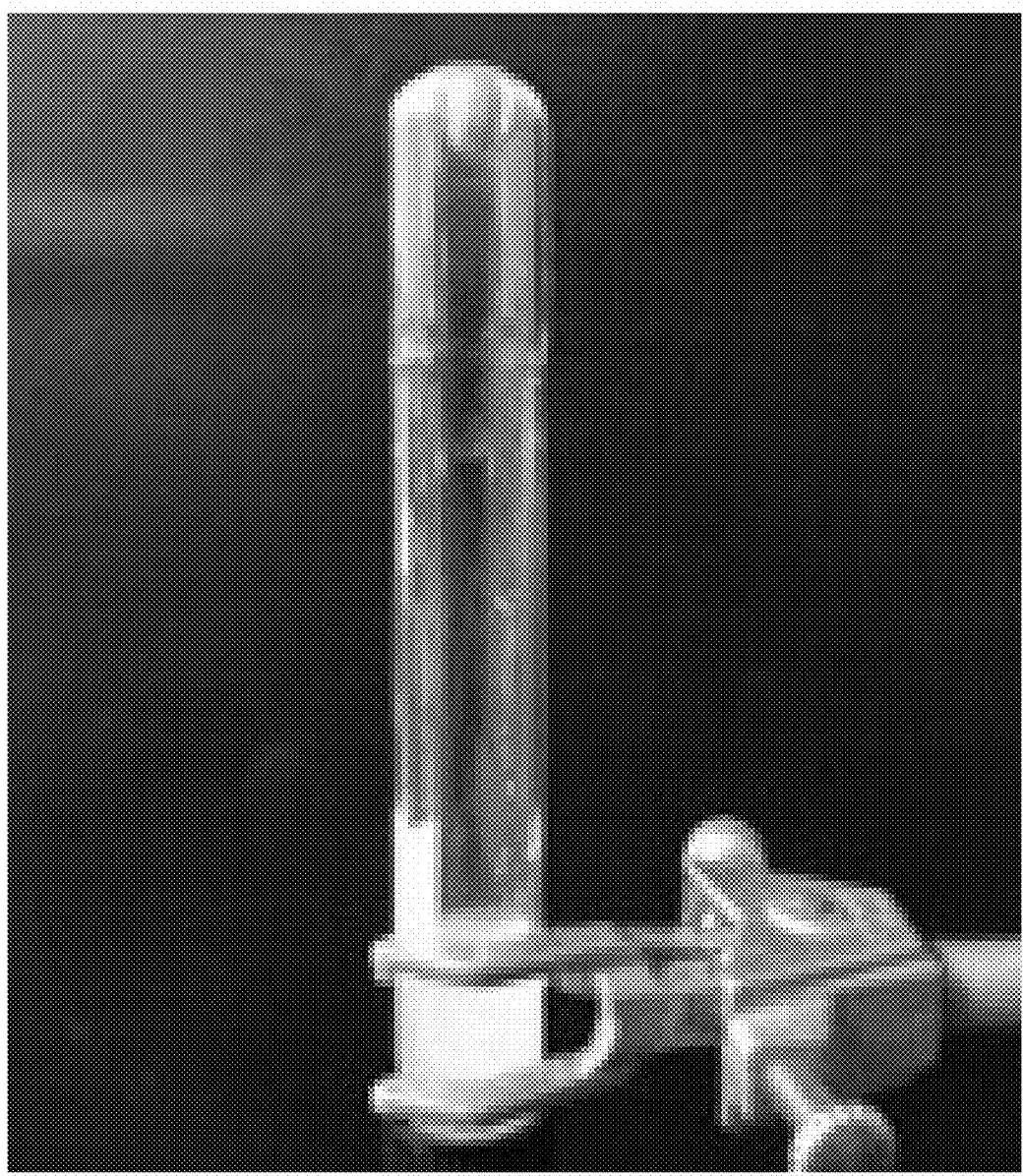

The sensitivity of PAH/PPi and PAH/TPP complexes to pH and ionic strength weakens their adhesion when they are prepared at (or exposed to) high/low pH and elevated salt concentrations. While their pH sensitivity can be partially addressed by using PAH analogues with higher effective $pK_a$-values (to maintain their high charge in alkaline solutions), their salt sensitivity indicates that the adhesive properties of these ionotropic complexes is especially useful at relatively low (roughly 0-150 mM) ionic strengths. This ionic strength range is sufficient for using these underwater adhesives in biomedical and pharmaceutical applications. The sensitivity of PAH/PPi and PAH/TPP mixtures to pH and ionic strength can also be exploited to expand their functionality. For instance, these adhesive complexes can be dissolved on demand by changing the pH. Another attractive feature of this salt and pH sensitivity is that it can be leveraged to develop injectable adhesives (for minimally invasive application) composed of low-viscosity dispersions that coagulate into gel-like macroscopic adhesives upon injection into their target sites. This effect has previously been achieved with biomimetic polymers and can be achieved with the readily available PAH/PPi and PAH/TPP mixtures. To demonstrate this, a TPP/PAH mixture was prepared at a TPP:PAH molar ratio of 0.40:1, where low-viscosity colloidal dispersions form in the absence of added salt (see FIG. 19B). The dispersion was then injected through a 21-gauge needle into 1× phosphate buffered saline (PBS) solution, which contained a Teflon-coated magnetic stir bar (see FIGS. 9A-9C). Upon its injection into PBS (where the ionic strength was near 150 mM), the dispersion spontaneously coagulated into a gel-like layer. Time-series photographs of this process are shown in FIGS. 9A-9D. As seen in FIG. 9D, the magnetic stir bar adhered to the test tube glass with a thin layer of gel 5 minutes after injection. This gel-like layer formed within 5 min of injection and adhered the Teflon-coated stir bar (5 mm×3 mm) to the bottom of the glass test tube (as shown by the tube inversion test in FIG. 9D). Thus, the salt sensitivity of PAH/PPi and PAH/TPP complexes (and likely also their pH sensitivity) can be harnessed to design injectable underwater adhesive formulations.

The short-term tensile bond strengths of PAH/PPi and PAH/TPP adhesives prepared at near-optimal conditions (i.e., of around 400 kPa; see FIGS. 17, 22) are similar to those reported for the natural underwater adhesives produced by barnacles and sandcastle worms. The reversibility and pH/salt sensitivity of their ionic cross-links, however, makes the bonds formed by PAH/PPi and PAH/TPP adhesives less permanent and robust than those achieved using covalent/biomimetic (e.g., catechol-based) chemistries. Despite this, their stimulus sensitivity and lack of potentially harmful covalent cross-linking render PAH/PPi and PAH/TPP adhesives especially useful in situations where: (1) temporary or reversible adhesion is desired and (2) harmful side reactions must be avoided. Furthermore, their simple, scalable and inexpensive preparation from readily-available ingredients make these underwater adhesives advantageous for larger-scale use, where the application of highly specialized biological (or biomimetic) polymers might not be feasible.

Materials and Methods

All experiments were conducted using Millipore Direct-Q 3 deionized water (18.2 MΩ·m). PAH (nominal molecular weight≈120-200 kDa) was obtained from Polysciences, Inc. (Warrington, Pa.) and Alpha Aesar (Ward Hill, Mass.). PPi and TPP (both sodium salts) were purchased from Sigma-Aldrich (St. Louis, Mo.). HCl and NaCl were obtained from Fisher Scientific (Fair Lawn, N.J.) and VWR (West Chester, Pa.), respectively. PBS was purchased in powder form from Fisher Scientific (Fair Lawn, N.J.). The glass and Teflon plates used for the adhesion tests were cut from Fisherfinest premium microscope slides (Fisher Scientific) and 0.25-in.-thick sheets of polytetrafluoroethylene (PTFE), respectively. All materials were used as received.

To construct the pH dependent state diagrams, 0.04 wt % (4.4 mM) PAH stock solutions were mixed with either 0.37 wt % (13.5 mM) PPi or 0.40 wt % (11.1 mM) TPP stock solutions at matching pH levels (which were varied between 2.0 and 12.0 using HCl and NaOH). Specifically, 2.5 mL aliquots of the PAH solution were injected with different volumes (40-400 µL) of either PPi or TPP solution. The cuvettes were then shaken by hand and allowed to equilibrate for 1 month. During equilibration, the formation and coagulation of colloidal dispersions was detected by dynamic light scattering (DLS), using a Zetasizer Nano ZS dynamic and electrophoretic light scattering instrument (Malvern, UK) as described previously. Here, a sudden increase in the light scattering intensity indicated the formation of colloidal dispersions, while a drastic increase in hydrodynamic diameter and polydispersity index (PDI), along with visible macroscopic precipitation, revealed the coagulation of colloidal complexes into gel-like adhesives. The ionic strength-dependent state diagrams were then constructed using the same procedure; however, the PAH, PPi, and TPP stock solutions were now prepared at variable NaCl concentrations (ranging between 0 and 500 mM) and a constant pH of 7.0.

The changes in the apparent ζ-potentials upon the addition of PPi and TPP to PAH were characterized by electrophoretic light scattering, again using the Zetasizer Nano ZS instrument (where the ζ-potentials were estimated from electrophoretic mobility measurements via the Smoluchowski equation). Here, 160 µL aliquots of either 0.37 wt % PPi or 0.40 wt % TPP at pH 6.0, 7.0, or 8.0 were sequentially added to 10 mL of 0.04 wt % PAH solution at a matching pH, while stirring the mixtures at 800 rpm with cylindrical magnetic stir bars (10 mm×5 mm). The ζ-potentials were then measured after each addition (following 10 min of equilibration). The evolutions in the apparent ζ-potentials with the addition of PPi and TPP to PAH mixtures at different NaCl concentrations were measured using the same procedure; however, the PPi, TPP and PAH solutions were now prepared at a fixed pH (of 7.0) and at variable NaCl concentrations (i.e., 0, 150 or 500 mM). Each measurement was performed using three replicate samples.

To quantify the pH and ionic strength effects on the water content within the adhesives, their samples were prepared at various pH and ionic strength levels, whereupon their wet and dry weights were measured. The samples at variable pH-levels were prepared by slowly adding either 3.9 wt % PPi solution or 5.7 wt % TPP solution at pH 6.0, 7.0 or 8.0 to 1000 mL of 0.1 wt % PAH at a matching pH. Since the amount of PPi and TPP required for macroscopic phase separation was pH-dependent, the volume of PPi and TPP solution added to the PAH solution varied with the pH. At pH 6.0 either 30 mL of PPi or 17 mL of TPP solution was added, at pH 7.0 either 26 mL of PPi or 14 mL of TPP solution was added, and at pH 8.0 either 22 mL of PPi or 11 mL of TPP solution was added. Furthermore, to ensure that the water content within the adhesive complexes was insensitive to the PPi, TPP and PAH compositions, additional complexes were prepared by adding either 30 mL of PPi solution or 17 mL of TPP solution to the PAH solution at pH 7.0 (which revealed no change in water content). Samples at variable NaCl concentrations were prepared in a similar fashion, by slowly adding 26 mL of 3.9 wt % PPi solution or 14 mL of 5.7 wt % TPP solution at pH 7.0 and 0, 150 or 300 mM NaCl to 1000 mL of 0.1 wt % PAH at a matching pH and NaCl concentration. During the PPi and TPP additions, the receiving PAH solutions were stirred at 300 rpm with cylindrical magnetic stir bars (5 cm×1 cm). The ionically cross-linked complexes were allowed to coagulate for 3 days, whereupon they were scraped from the bottoms of the beakers. The wet weight of each adhesive sample (0.175-0.190 g) was then recorded after carefully removing all excess supernatant from the sample surface with a KimWipe. The samples were dried for 72 h in an oven at 37°

C., whereupon the dry mass of the adhesive was recorded. All measurements were performed in triplicate.

The dynamic rheology of the adhesives was characterized at room temperature using a Rheometric Scientific RDA III (Piscataway, N.J.) strain-controlled rheometer equipped with 25-mm parallel plates. The samples were prepared using the procedure described above. The gel-like complexes were then loaded into the rheometer, compressed to a 0.5-mm gap thickness and allowed to relax between the plates until the normal force was below 100 g. The excess sample was then removed using a spatula, and water was applied to its exposed outer edges to prevent drying. After performing strain amplitude sweeps to determine the linear viscoelasticity region, frequency sweeps were performed at 0.1-500 rad/s angular velocities and a 1.0% strain amplitude for all of the samples except for those prepared from parent solutions at pH 8.0. When prepared at this higher pH, the adhesives were much softer and required a 10.0% strain amplitude (which for these samples was still within the linear viscoelasticity region) to achieve sufficient torque. Three replicate samples were analyzed under each condition.

The adhesive complexes were prepared at variable pH-levels by slowly adding 4.2 wt % (158 mM) PPi or 5.6 wt % (152 mM) TPP solution at pH 6.0, 7.0, or 8.0 to 1000 mL of 0.3 wt % (32 mM) PAH at the same pH. The volume of PPi and TPP solution added to the PAH again depended on the pH used (with either 76 mL of PPi or 50 mL of TPP solution added at pH 6.0, either 66 mL of PPi or 42 mL of TPP solution added at pH 7.0, and either 56 mL of PPi or 33 mL of TPP solution added at pH 8.0). This variance in PPi and TPP solution volume was again necessary to ensure that adhesive formation occurred and had no discernible impact on adhesive properties (as confirmed by probing the rheology and adhesion strengths of complexes prepared from solutions at pH 7.0 and PPi:PAH or TPP:PAH molar ratios ranging between 0.33-0.38:1 and 0.20-0.24:1, respectively; data not shown). The adhesive samples were similarly prepared at variable NaCl concentrations by slowly adding 66 mL of 4.2 wt % PPi solution or 42 mL of 5.6 wt % TPP solution at pH 7.0 and 0, 150 or 300 mM NaCl to 1000 mL of 0.3 wt % PAH solution at a matching pH and NaCl concentration. Each receiving PAH solution was stirred at 300 rpm as indicated above.

The gel-like complexes were then equilibrated for 3 days before being collected from the bottoms of the beakers and being used to adhere two 2.5 cm×2.5 cm substrate surfaces (either glass or Teflon). Each substrate was superglued onto custom-made Plexiglas brackets (using Loctite Glass Glue for the glass and Gorilla Super Glue for the Teflon), which enabled its placement into the stress-strain analyzer. To adhere the two plates, 0.5-1.0 g of the adhesive complex (a more precise application was complicated by its adhesion to the spatula) was pressed between the plates to a final thickness of 0.33-0.43 mm. For the samples prepared at pH 6.0 and 7.0 and NaCl concentrations of 0 and 150 mM, this was achieved by pressing the two plates together for 3 h under deionized water and 24 kPa of pressure. Conversely, for the samples prepared at pH 8.0 and 300 mM NaCl, this was achieved by hand pressing the two plates together under deionized water to the specified (0.33-0.43 mm) thickness. This alternative procedure was used because these adhesive complexes were much softer and applying 24 kPa of pressure for 3 h caused most of the adhesive to be squeezed out from between the two plates (resulting in much thinner adhesive layers). After removing the excess adhesive from the sides of the plates, the adhered plates remained submerged in deionized water (for 15-30 mM) until the tensile bond strength test was performed using an Instron 4400R Universal Testing Machine (UTM; Norwood, Mass.). The adhered plates were then clamped into the grips of the UTM and immediately separated at a crosshead speed of 0.85 mm/s while measuring both the force and displacement. Each measurement was repeated six times.

The samples for the adhesion longevity tests were prepared and compressed between two glass plates using the procedure described above. One plate was then held stationary while a 1.1-kg weight was suspended from the second plate (thereby applying a 17.8-kPa tensile stress to the bond). The time required for the adhesion to fail at each pH-value and NaCl concentration was then measured while reapplying deionized water to the exposed edges of the adhesives every 5 min to prevent them from drying. To ensure reproducibility, each measurement was replicated thrice.

To demonstrating preparation of stimulus-responsive injectable adhesives, 1.40 mL of 5.7 wt % TPP solution was added to 10.0 mL of 0.5 wt % PAH solution (both at pH 7.0 and 0 mM NaCl), so that the TPP:PAH molar ratio was 0.40:1. One mL of the dispersion was then injected through a 21-gauge syringe needle into 1 mL of 1×PBS containing a Teflon-coated magnetic stir bar (5 mm×3 mm). After the dispersion was added to the PBS solution, the mixture remained undisturbed (without stirring) for 5 mM, whereupon the test tube was inverted to determine whether the Teflon-coated stir bar was adhered to the glass test tube.

Certain embodiments of the compositions and methods disclosed herein are defined in the above examples. It should be understood that these examples, while indicating particular embodiments of the invention, are given by way of illustration only. From the above discussion and these examples one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A composition comprising:
   a non-polysaccharide polymer having two or more amine groups; and
   a multivalent phosphate crosslinker;
   the composition comprising an ionically crosslinked network that forms a gel-like coacervate at a pH in the range of from about 4 to about 10;
   wherein the non-polysaccharide polymer having two or more amine groups is poly(allylamine hydrochloride) (PAH) and the multivalent phosphate crosslinker is selected from the group consisting of pyrophosphate (PPi) and tripolyphosphate (TPP).

2. The composition of claim 1, wherein the PAH has a nominal molecular weight ranging from about 1 kDa to about 2,500 kDa.

3. The composition of claim 1, wherein the non-polysaccharide polymer having two or more amine groups consists of PAH, and the multivalent crosslinker consists of PPi.

4. The composition of claim 3, wherein the composition has a crosslinker:polymer molar ratio above about 0.12:1.

5. The composition of claim 1, wherein the non-polysaccharide polymer having two or more amine groups consists of PAH, and the multivalent crosslinker consists of TPP.

6. The composition of claim 5, wherein the composition has a crosslinker:polymer molar ratio ranging from about 0.10:1 to about 0.25:1.

7. The composition of claim 1, wherein the polymer is present at a concentration ranging from about 0.1 wt % to about 40 wt %.

8. The composition of claim 1, wherein the composition contains water at a concentration ranging from about 20 wt % to about 50 wt %.

9. The composition of claim 1, wherein the composition has a storage modulus of greater than $10^5$ Pa.

10. The composition of claim 1, wherein the composition exhibits a self-healing capability when torn.

11. The composition of claim 1, wherein the composition has a tensile adhesion strength of greater than about 350 kPa.

12. The composition of claim 1, wherein the composition is capable of adhering to hydrophobic and hydrophilic surfaces under water.

13. The composition of claim 1, wherein the composition is capable of adhering to human skin.

14. The composition of claim 1, further comprising an active payload for long-term release.

15. The composition of claim 14, wherein the active payload comprises a fragrance.

\* \* \* \* \*

UNITED STATES PATENT AND TRADEMARK OFFICE
CERTIFICATE OF CORRECTION

PATENT NO. : 9,814,778 B2
APPLICATION NO. : 14/639759
DATED : November 14, 2017
INVENTOR(S) : Yakov Lapitsky et al.

It is certified that error appears in the above-identified patent and that said Letters Patent is hereby corrected as shown below:

On the Title Page

Please correct (54) the title from:
"IONICALLY CROSSLINKED POLYELECTROLYTES AS UNDERWATER ADHESIVES AS CONTROLLED RELEASE VEHICLES"
To:
-- IONICALLY CROSSLINKED POLYELECTROLYTES AS UNDERWATER ADHESIVES AND CONTROLLED RELEASE VEHICLES --.

Signed and Sealed this
Twenty-sixth Day of December, 2017

Joseph Matal
*Performing the Functions and Duties of the
Under Secretary of Commerce for Intellectual Property and
Director of the United States Patent and Trademark Office*